US010010605B2

(12) United States Patent
Audonnet et al.

(10) Patent No.: US 10,010,605 B2
(45) Date of Patent: Jul. 3, 2018

(54) FMDV RECOMBINANT VACCINES AND USES THEREOF

(71) Applicant: MERIAL, INC., Duluth, GA (US)

(72) Inventors: Jean-Christophe Audonnet, Lyons (FR); Zahia Hannas-Djebbara, Francheville (FR); Teshome Mebatsion, Watkinsville, GA (US); Yu-Wei Chiang, Athens, GA (US); Justin Widener, Athens, GA (US); Frédéric Reynard, St Bonnet-de-Mure (FR)

(73) Assignee: Merial, Inc., Duluth, GA (US)

( * ) Notice: Subject to any disclaimer, the term of this patent is extended or adjusted under 35 U.S.C. 154(b) by 55 days.

(21) Appl. No.: 14/863,181

(22) Filed: Sep. 23, 2015

(65) Prior Publication Data

US 2016/0220659 A1 Aug. 4, 2016

Related U.S. Application Data

(60) Provisional application No. 62/054,073, filed on Sep. 23, 2014.

(51) Int. Cl.

| | |
|---|---|
| ***A61K 39/135*** | (2006.01) |
| ***A61K 39/12*** | (2006.01) |
| ***C07K 14/005*** | (2006.01) |
| ***C12N 7/00*** | (2006.01) |
| *A61K 39/00* | (2006.01) |

(52) U.S. Cl.

CPC ............ *A61K 39/135* (2013.01); *A61K 39/12* (2013.01); *C07K 14/005* (2013.01); *C12N 7/00* (2013.01); *A61K 2039/5258* (2013.01); *A61K 2039/545* (2013.01); *A61K 2039/55577* (2013.01); *C12N 2710/10043* (2013.01); *C12N 2710/14043* (2013.01); *C12N 2770/32123* (2013.01); *C12N 2770/32134* (2013.01)

(58) Field of Classification Search

None

See application file for complete search history.

(56) References Cited

U.S. PATENT DOCUMENTS

| | | | |
|---|---|---|---|
| 7,531,182 | B2 | 5/2009 | King |
| 8,323,663 | B2 | 12/2012 | Brough |
| 2009/0253185 | A1 | 10/2009 | Nordgren et al. |
| 2011/0236416 | A1 | 9/2011 | Audonnet |

FOREIGN PATENT DOCUMENTS

| | | |
|---|---|---|
| CA | 2047585 | 1/1992 |

OTHER PUBLICATIONS

Kumar et al., Indian J. Virol., Oct.-Dec. 2012, 23(3):326-332.*
Animal and Plant Health Inspection Service (APHIS), USDA, Factsheet, Mar. 2007, two pages, accessed on May 22, 2017: www.cdfa.ca.gov/ahfss/Animal_Health/pdfs/fmd_vaccine_07_USDA-fs.pdf).*
Segundo et al., J. Virol., Feb. 2016, 90(3):1298-1310.*
Xiao et al., BMC Biotechnology, 2016, 16:56, nine pages.*
PharMingen, Baculovirus Expression Vector System Manual, Instruction Manual, 6th edition, May 1999, 118 pages, available from https://www.bdbiosciences.com/documents/Baculovirus_vector_system_manual.pdf.*
Belsham G. J., 1993, "Distinctive features of foot-and-mouth disease virus, a member of the picornavirus family; aspects of virus protein synthesis, protein processing and structure", Progress in Biophysics and Molecular Biology, 60, 241-261.
Cooper et al., 1978, "Picornaviridae" second report, Intervirology, 10, 165-180.
Graves, 1963, "Transfer of neutralizing antibody by colostrum to calves born of foot-and-mouth disease vaccinated dams", Journal of Immunology 91:251-256.
Grubman et al.,1993, "Protection of swine against foot-and-mouth disease with viral capsid proteins expressed in heterologous systems", Vaccine, 11, 825-829.
King, A.M.Q. et al., 1981, "Biochemical identification of viruses causing the 1981 outbreaks of foot and mouth disease in the UK", Nature 293: 479-480.
Kleid et al. 1981, "Cloned viral protein vaccine for foot-and-mouth disease: responese in cattle and swine", Science, 214, 1125-1129.
Lewis et al., J. Virol., 1991, "Expression, processing, and assembly of foot-and-mouth disease virus capsid structures in heterologous systems: induction of a neutralizing antibody response in guinea pigs", 65, 6572-6580.
Rowlands et al., J., 1975, "A comparative chemical and serological study of the full and empty particles of foot-and-mouth disease virus", Gen. Virol., 26, 227-238.
Rweyemamu et al.,1979, "Stability and immunogenicity of empty particles of foot-and-mouth disease virus", Archives of Virology, 59, 69-79.
Claudine Porta et al., 2013, J. of Virological Methods, vol. 187, No. 2, p. 406-412, "Efficient production of foot-and-mouth disease virus emplty capsids in insect cells following down regulation of 3C protease activity".
B. Mohana Subramanian et al., 2012, Antiviral Research, vol. 96, No. 3, p. 288-295, "Development of foot-and-mouth disease virus (FMDV) serotype O virus-like-particles (VLPs) vaccine and evaluation of its potency".
Diana M. Alejo et al., 2013, Vaccine vol. 31 No. 18, p. 2302-2309, "An adenovirus vectored musocal adjuvant augments protection of mice immunized intranasally with an adenovirus-vectored foot-and-mouth disease virus subunit vaccine".
Guohui Zhou et al., 2013, Research in Veterinary Science, vol. 94, No. 3, p. 796-802, "Recombinant adenovirus expressing type Asial foot-and-mouth disease virus capsid proteins induces protective immunity against homologous virus challenge in mice".

* cited by examiner

*Primary Examiner* — Stacy B Chen

(74) *Attorney, Agent, or Firm* — Judy Jarecki-Black; Suzanne Shope

(57) ABSTRACT

The present invention encompasses FMDV vaccines or compositions. The vaccine or composition may be a vaccine or composition containing FMDV antigens. The invention also encompasses recombinant vectors encoding and expressing FMDV antigens, epitopes or immunogens which can be used to protect animals, in particular ovines, bovines, caprines, or swines, against FMDV.

12 Claims, 43 Drawing Sheets

Figure 1

| SEQ ID NO: | type | Gene Description |
|---|---|---|
| 1 | protein | Wild-type polyprotein of FMDV A24 Cruzeiro Strain (GenBank AAT01711) |
| 2 | protein | Modified polyprotein of A24 Cruzeiro Strain in VP2 (H93C) or P1 (H179C) (in pMEB097) |
| 3 | DNA | Polynucleotide encoding modified polyprotein of FMDV A24 (in pMEB097) |
| 4 | protein | Unmodified Polyprotein of A24 Cruzeiro Strain (in pMEB084) |
| 5 | protein | Wild-type polyprotein of FMDV O1 manisa strain (GenBank AAT01766) (in pMEB095) |
| 6 | protein | Modified polyprotein of FMDV O1 manisa strain in VP2 (S93C) or P1 (S179C) (in pMEB099) |
| 7 | DNA | Polynucleotide encoding modified polyprotein of FMDV O1 manisa strain (in pMEB099) |
| 8 | protein | Modified polyprotein of FMDV Iraq strain (in pMEB106) |
| 9 | DNA | Polynucleotide encoding modified polyprotein of FMDV Iraq strain (in pMEB106) |
| 10 | protein | Modified polyprotein of FMDV Asia strain (in pMEB104) |
| 11 | DNA | Polynucleotide encoding modified polyprotein of FMDV Asia strain (in pMEB104) |
| 12 | protein | Wild-type polyprotein of FMDV Iraq strain (in pMEB105) |
| 13 | protein | Wild-type polyprotein of FMDV Asia strain (in pMEB102) |
| 14 | DNA | Polynucleotide encoding wild-type polyprotein of FMDV Iraq strain (in pMEB105) |
| 15 | DNA | Polynucleotide encoding wild-type polyprotein of FMDV Asia strain (in pMEB102) |
| 16 | protein | FMDV capsid precursor (VP1, VP2 (with H93C site mutation), VP3, VP4, 2A, and Full 2B codon optimized) and a non-optimized partial 3B and full length 3C protease with C142T site mutation (in vAD3027) |
| 17 | DNA | Codon-optimized polynucleotide encoding FMDV capsid precursor (in vAD3027) |
| 18 | DNA | CMV promoter |
| 19 | DNA | Synthetic enhancer |
| 20 | DNA | CMV promoter –synthetic enhancer- codon optimized FMDV capsid gene – SV40 PolyA in vAD3027 |

Figure 4
Result of electronic microscopy of BacMEB097
| Recombinant Baculovirus Construction | **A**<br>W/O treatment | **B**<br>1h at 56°C | **C**<br>Acidification: pH=5 |
|---|---|---|---|
| "classical A24" =**BacMEB084** Samples [] 4X | 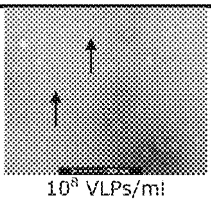<br>$10^8$ VLPs/ml | 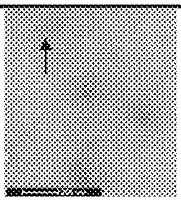<br>Only very few particles detected | No VLPs |
| "stabilized A24" =**BacMEB097** Samples [] 3,3X | 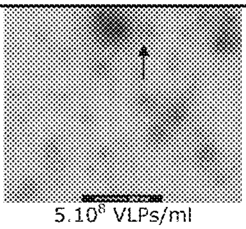<br>5.$10^8$ VLPs/ml | 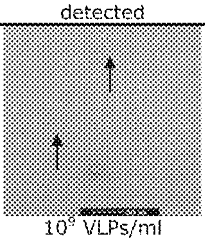<br>$10^9$ VLPs/ml | 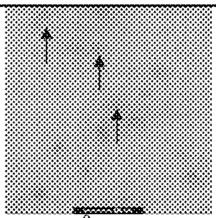<br>2.$10^9$ VLPs/ml |

Detection by western blot of capsid protein of FMDV (A24 serotype)

A: no treatment (pH=6.1)
B: 1hr at 56°C
C: 4.7 < pH < 5
D: pH adjusted at 6.5
PA: inactivated FMDV A24

Figure 6
Electronic microscopy and specific ELISA of BacMEB099
Fig. 6A
| | | | Harvest at day 4 | | |
|---|---|---|---|---|---|
| Construct | Clone | MOI | Num | Viability | [] |
| **BacMEB099** | **4** | 0,45 | 2,80E+05 | 16,9% | 12x |
Fig. 6B
| No treatment | | 1 hour at 56°C | |
|---|---|---|---|
| ELISA* | EM | ELISA* | EM |
| 2,29 | 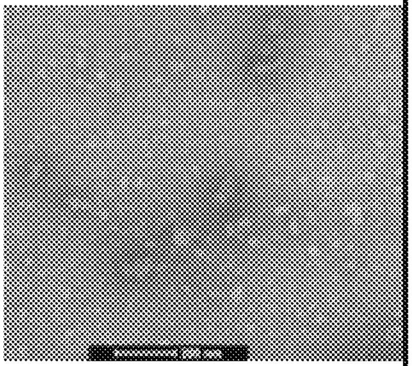 $10^9$ VLP/ml | 2,11 | 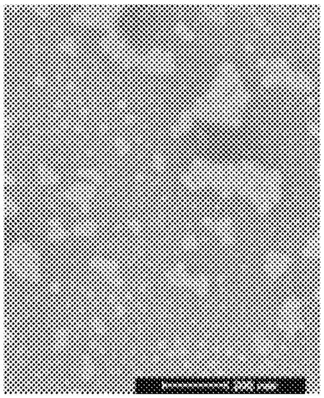 $10^9$ VLP/ml |

Figure 7A
1 50
SEQ ID NO:1 (AAT01711) (1) MNTTDCFIALVHAIREIRAFFLPRATGRMEFTLHNGERKVFYSRPNNHDN
SEQ ID NO:2 (pMEB097) (1)
SEQ ID NO:4 (pMEB084) (1)
51 100
SEQ ID NO:1 (AAT01711) (51) CWLNTILQLFRYVGEPFFDWVYDSPENLTLEAIEQLEELTGLELHEGGPP
SEQ ID NO:2 (pMEB097) (1)
SEQ ID NO:4 (pMEB084) (1)
101 150
SEQ ID NO:1 (AAT01711) (101) ALVIWNIKHLLHTGIGTASRPSEVCMVDGTNMCLADFHAGIFLKGQEHAV
SEQ ID NO:2 (pMEB097) (1)
SEQ ID NO:4 (pMEB084) (1)
151 200
SEQ ID NO:1 (AAT01711) (151) FACVTSNGWYAIDDEDFYPWIPDPSDVLVFVPYDQEPLNGEWKIKVQQKL
SEQ ID NO:2 (pMEB097) (1)
SEQ ID NO:4 (pMEB084) (1)
201 250
SEQ ID NO:1 (AAT01711) (201)
SEQ ID NO:2 (pMEB097) (1)
SEQ ID NO:4 (pMEB084) (1)
251 300
SEQ ID NO:1 (AAT01711) (251)
SEQ ID NO:2 (pMEB097) (51)
SEQ ID NO:4 (pMEB084) (51)
301 350
SEQ ID NO:1 (AAT01711) (301)
SEQ ID NO:2 (pMEB097) (101)
SEQ ID NO:4 (pMEB084) (101)
351 400
SEQ ID NO:1 (AAT01711) (351)
SEQ ID NO:2 (pMEB097) (151)
SEQ ID NO:4 (pMEB084) (151)
401 450
SEQ ID NO:1 (AAT01711) (401)
SEQ ID NO:2 (pMEB097) (201)
SEQ ID NO:4 (pMEB084) (201)
451 500
SEQ ID NO:1 (AAT01711) (451)
SEQ ID NO:2 (pMEB097) (251)
SEQ ID NO:4 (pMEB084) (251)
501 550
SEQ ID NO:1 (AAT01711) (501)
SEQ ID NO:2 (pMEB097) (301)
SEQ ID NO:4 (pMEB084) (301)
551 600
SEQ ID NO:1 (AAT01711) (551)
SEQ ID NO:2 (pMEB097) (351)
SEQ ID NO:4 (pMEB084) (351)

Alignment of the amino acid sequences of the recombinant polyprotein in pMEB097 and and reference sequence (FMDV serotype A / Genbank (AAT01711) using the vector NTI program Figure 7A (continued)

```
                                        601                                              650
SEQ ID NO:1 (AAT01711)  (601)  YYTQYSGTINLHEMFTGSTDSKARYMVAYIPPGVETPPDTPEEAAHCIHA
SEQ ID NO:2 (pMEB097)   (401)  YYTQYSGTINLHEMFTGSTDSKARYMVAYIPPGVETPPDTPEEAAHCIHA
SEQ ID NO:4 (pMEB084)   (401)  YYTQYSGTINLHEMFTGSTDSKARYMVAYIPPGVETPPDTPEEAAHCIHA

                                        651                                              700
SEQ ID NO:1 (AAT01711)  (651)  EWDTGLNSKFYFSIPYVSAADYAYTASDTAETINVQGWVCIYQITHGKAE
SEQ ID NO:2 (pMEB097)   (451)  EWDTGLNSKFYFSIPYVSAADYAYTASDTAETINVQGWVCIYQITHGKAE
SEQ ID NO:4 (pMEB084)   (451)  EWDTGLNSKFYFSIPYVSAADYAYTASDTAETINVQGWVCIYQITHGKAE

                                        701                                              750
SEQ ID NO:1 (AAT01711)  (701)  NDTLVVSVSAGKDFELRLPIDPRQQTTATHESADFVTTTVENYCGKTQIQ
SEQ ID NO:2 (pMEB097)   (501)  NDTLVVSVSAGKDFELRLPIDPRQQTTATHESADFVTTTVENYCGKTQIQ
SEQ ID NO:4 (pMEB084)   (501)  NDTLVVSVSAGKDFELRLPIDPRQQTTATHESADFVTTTVENYCGKTQIQ

                                        751                                              800
SEQ ID NO:1 (AAT01711)  (751)  RRHHTDISFIMGSFVRIQSLSPTHVIDLMQTHQHGLVGALLRAATYYFSD
SEQ ID NO:2 (pMEB097)   (551)  RRHHTDISFIMGSFVRIQSLSPTHVIDLMQ[illegible]HQHGLVGALLRAATYYFSD
SEQ ID NO:4 (pMEB084)   (551)  RRHHTDISFIMGSFVRIQSLSPTHVIDLMQ[illegible]HQHGLVGALLRAATYYFSD

                                        801                                              850
SEQ ID NO:1 (AAT01711)  (801)  LRIVVHHDSNLTWVPNGAPESALLNTSNPTAYNKAPFTPLALSYTAPHRV
SEQ ID NO:2 (pMEB097)   (601)  LRIVVHHDSNLTWVPNGAPESALLNTSNPTAYNKAPFTPLALSYTAPHRV
SEQ ID NO:4 (pMEB084)   (601)  LRIVVHHDSNLTWVPNGAPESALLNTSNPTAYNKAPFTPLALSYTAPHRV

                                        851                                              900
SEQ ID NO:1 (AAT01711)  (851)  LATVYHGTSKYAVGGSGRRGIHGSLAARVVHQLEASFHDGAIKADAIHEL
SEQ ID NO:2 (pMEB097)   (651)  LATVYHGTSKYAVGGSGRRGIHGSLAARVVHQLEASFHDGAIKADAIHEL
SEQ ID NO:4 (pMEB084)   (651)  LATVYHGTSKYAVGGSGRRGIHGSLAARVVHQLEASFHDGAIKADAIHEL

                                        901                                              950
SEQ ID NO:1 (AAT01711)  (901)  LVRMKRAELYCPRPLLATEVSSQDRHKQKIIAPAKQLLNFDLLKLAGDVE
SEQ ID NO:2 (pMEB097)   (701)  LVRMKRAELYCPRPLLATEVSSQDRHKQKIIAPAKQLLNFDLLKLAGDVE
SEQ ID NO:4 (pMEB084)   (701)  LVRMKRAELYCPRPLLATEVSSQDRHKQKIIAPAKQLLNFDLLKLAGDVE

                                        951                                             1000
SEQ ID NO:1 (AAT01711)  (951)  SNPGPFFT[illegible]DVRSNFSFLVDTIHQMQEDMSIEHGPDFNRLVSAFEELATG
SEQ ID NO:2 (pMEB097)   (751)  SNPGPFFT[illegible]DVRSNFSFLVDTIHQMQEDMSIEHGPDFNRLVSAFEELATG
SEQ ID NO:4 (pMEB084)   (751)  SNPGPFFT[illegible]DVRSNFSFLVDTIHQMQEDMSIEHGPDFNRLVSAFEELATG

                                        1001                                            1050
SEQ ID NO:1 (AAT01711) (1001)  VKAIRKGLDEAKPWYKLIKLLSRLSCMAAYAAFSKDPVLAVAINLADI[illegible]
SEQ ID NO:2 (pMEB097)   (801)  VKAIRKGLDEAKPWYKLIKLLSRLSCMAAYAAFSKDPVLAVAINLADI---
SEQ ID NO:4 (pMEB084)   (801)  VKAIRKGLDEAKPWYKLIKLLSRLSCMAAYAAFSKDPVLAVAINLADI[illegible]

                                        1051                                            1100
SEQ ID NO:1 (AAT01711) (1051)  ILDSTFVVKKISDSLSSLFHVPAPVFSFGAPILLAGLVKVASSFFRSTPE
SEQ ID NO:2 (pMEB097)   (848)  --------------------------------------------------
SEQ ID NO:4 (pMEB084)   (851)  --------------------------------------------------

                                        1101                                            1150
SEQ ID NO:1 (AAT01711) (1101)  DLERAEKQLKARDINDIFAILKNGEWLVKLILAIRDWIKAWIASEEKFVT
SEQ ID NO:2 (pMEB097)   (848)  --------------------------------------------------
SEQ ID NO:4 (pMEB084)   (851)  --------------------------------------------------

                                        1151                                            1200
SEQ ID NO:1 (AAT01711) (1151)  TTDLVPGILEKQRDLNDPSKYKEAKEWLDNARQACLKSGNVHIANLCKVV
SEQ ID NO:2 (pMEB097)   (848)  --------------------------------------------------
SEQ ID NO:4 (pMEB084)   (851)  --------------------------------------------------

                                        1201                                            1250
SEQ ID NO:1 (AAT01711) (1201)  APAPSRSRPEPVVVCLRGKSGQGKSFLANVLAQAISTHFTGRTDSVWYCP
SEQ ID NO:2 (pMEB097)   (848)  --------------------------------------------------
SEQ ID NO:4 (pMEB084)   (851)  --------------------------------------------------
```

Figure 7A (continued)

```
                                  1251                                              1300
SEQ ID NO:1 (AAT01711) (1251) PDPDHFDGYNQQTVVVMDDLGQNPDGKDFKYFAQMVSTTGFIPPMASLED
SEQ ID NO:2 (pMEB097)   (848) --------------------------------------------------
SEQ ID NO:4 (pMEB084)   (851) --------------------------------------------------

                                  1301                                              1350
SEQ ID NO:1 (AAT01711) (1301) KGKPFNSKVIIATTNLYSGFTPRTMVCPDALNRRFHFDIDVSAKDGYKIN
SEQ ID NO:2 (pMEB097)   (848) --------------------------------------------------
SEQ ID NO:4 (pMEB084)   (851) --------------------------------------------------

                                  1351                                              1400
SEQ ID NO:1 (AAT01711) (1351) NKLDIIKALEDTHTNPVAMFQYDCALLNGMAVEMKRMQQDMFKPQPPLQN
SEQ ID NO:2 (pMEB097)   (848) --------------------------------------------------
SEQ ID NO:4 (pMEB084)   (851) --------------------------------------------------

                                  1401                                              1450
SEQ ID NO:1 (AAT01711) (1401) VYQLVQEVIERVELHEKVSSHPIFKQISIPSQKSVLYFLTEKGQHEAAIE
SEQ ID NO:2 (pMEB097)   (848) --------------------------------------------------
SEQ ID NO:4 (pMEB084)   (851) --------------------------------------------------

                                  1451                                              1500
SEQ ID NO:1 (AAT01711) (1451) FFEGMVHDSKKEERRPLIQQTSFVKRAFKRLKENFEIVALCLTLLANIVI
SEQ ID NO:2 (pMEB097)   (848) --------G---EEQR----------------------------------
SEQ ID NO:4 (pMEB084)   (851) ------------RQRPE---------------------------------

                                  1501                                              1550
SEQ ID NO:1 (AAT01711) (1501) MIRETRKRQKMVDDAVSEYIERANITTDDKTLDEAEKNPLETSGASTVGF
SEQ ID NO:2 (pMEB097)   (854) --------------------------------------------------
SEQ ID NO:4 (pMEB084)   (856) --------------------------------------------------

                                  1551                                              1600
SEQ ID NO:1 (AAT01711) (1551) KEEPLPGQKARNDENSEPAQPAEEQPQAEGPYAGPLERQKKVFRKLPQ
SEQ ID NO:2 (pMEB097)   (854) ------------------------------------------KFVRAKLPQ
SEQ ID NO:4 (pMEB084)   (856) ------------------------------------------FVRAKLPQ

                                  1601                                              1650
SEQ ID NO:1 (AAT01711) (1601) QEGPYACPEERQPTLKVKAKAPVVKEGPYEGPVKKPVALKVFAKNLIVTE
SEQ ID NO:2 (pMEB097)   (864) QEGPYACPEERQPPLKVKAKAPVVKEGPYEGPVKKPVALKVFAKNLIVTE
SEQ ID NO:4 (pMEB084)   (864) QEGPYACPEERQPPLKVKAKAPVVKEGPYEGPVKKPVALKVFAKNLIVTE

                                  1651                                              1700
SEQ ID NO:1 (AAT01711) (1651) NSAPPTGLQKVMGNTKPVELILLDGKTVAIDCATGVFCTAKLVPRKLPAE
SEQ ID NO:2 (pMEB097)   (914) NSAPPTGLQKVMGNTKPVELILLDGKTVAIDCATGVFCTAKLVPRKLPAE
SEQ ID NO:4 (pMEB084)   (914) NSAPPTGLQKVMGNTKPVELILLDGKTVAIDCATGVFCTAKLVPRKLPAE

                                  1701                                              1750
SEQ ID NO:1 (AAT01711) (1701) KYDKIMLDGRAMTDSDYPVYEPEIKVEDQDMLSDAALMVLRRGNRVRDIT
SEQ ID NO:2 (pMEB097)   (964) KYDKIMLDGRAMTDSDYPVYEPEIKVEDQDMLSDAALMVLRRGNRVRDIT
SEQ ID NO:4 (pMEB084)   (964) KYDKIMLDGRAMTDSDYPVYEPEIKVEDQDMLSDAALMVLRRGNEVRDIT

                                  1751                                              1800
SEQ ID NO:1 (AAT01711) (1751) KKFKLTARMKKGTPVVGVANNAIVGHLIFSGEAITNEDIVVCMIKDTMPG
SEQ ID NO:2 (pMEB097)  (1014) KKFKLTARMKKGTPVVGVANNAIVGHLIFSGEAITNEDIVVCMIKDTMPG
SEQ ID NO:4 (pMEB084)  (1014) KKFKLTARMKKGTPVVGVANNAIVGHLIFSGEAITNEDIVVCMIKDTMPG

                                  1801                                              1850
SEQ ID NO:1 (AAT01711) (1801) LPAYKAATKAGVKKGAVLAKDGAPTYIVGTHEAMKGNGVGYCSCVSRSML
SEQ ID NO:2 (pMEB097)  (1064) LPAYKAATKAGVGGGAVLAKDGAPTYIVGTHEAMGGNGVGYCSCVSRSML
SEQ ID NO:4 (pMEB084)  (1064) LPAYKAATKAGVGGGAVLAKDGAPTYIVGTHEAMGGNGVGYCSCVSRSML

                                  1851                                              1900
SEQ ID NO:1 (AAT01711) (1851) KMPAHVDPEPHHEGLIVDTRDVEERVHVMRKTKLAPTVAHGVFNPEFGPA
SEQ ID NO:2 (pMEB097)  (1114) KMPAHVDPEPHHE-------------------------------------
SEQ ID NO:4 (pMEB084)  (1114) KMPAHVDPEPHHE-------------------------------------
```

Figure 7A (continued)

```
                                      1901                                             1950
SEQ ID NO:1 (AATC1711) (1901) ALSNKDPRLNDGVVLDEVIFSKHKGDTKMSEEDKALFRRCAADYASRLHS
SEQ ID NO:2 (pMEB097)  (1127) --------------------------------------------------
SEQ ID NO:4 (pMEB084)  (1127) --------------------------------------------------

                                      1951                                             2000
SEQ ID NO:1 (AATC1711) (1951) VLGTANAPLSIYEAIKGVDGLDAMEPDTAPGLPWALQGKRRGALIDFENG
SEQ ID NO:2 (pMEB097)  (1127) --------------------------------------------------
SEQ ID NO:4 (pMEB084)  (1127) --------------------------------------------------

                                      2001                                             2050
SEQ ID NO:1 (AATC1711) (2001) TVGPEVEAALKLMEKREYKFACQTFLKDEIRPMEKVRAGKTRIVDVLPVE
SEQ ID NO:2 (pMEB097)  (1127) --------------------------------------------------
SEQ ID NO:4 (pMEB084)  (1127) --------------------------------------------------

                                      2051                                             2100
SEQ ID NO:1 (AATC1711) (2051) HILYTRMMIGRFCAQMHSNNGPQIGSAVGCNPDVDWQRFGTHFAQYRNVW
SEQ ID NO:2 (pMEB097)  (1127) --------------------------------------------------
SEQ ID NO:4 (pMEB084)  (1127) --------------------------------------------------

                                      2101                                             2150
SEQ ID NO:1 (AATC1711) (2101) DVDYSAFDANHCSDAMNIMFEEVFRTEFCFHPNAEWILKTLVNTEHAYEN
SEQ ID NO:2 (pMEB097)  (1127) --------------------------------------------------
SEQ ID NO:4 (pMEB084)  (1127) --------------------------------------------------

                                      2151                                             2200
SEQ ID NO:1 (AATC1711) (2151) KRITVEGGMPSGCSATSIINTILNNIYVLYALRRHYEGVELDTYTMISYG
SEQ ID NO:2 (pMEB097)  (1127) --------------------------------------------------
SEQ ID NO:4 (pMEB084)  (1127) --------------------------------------------------

                                      2201                                             2250
SEQ ID NO:1 (AATC1711) (2201) DDIVVASDYDLDFEALKPHFKSLGQTITPADKSDKGFVLGHSITDVTFLK
SEQ ID NO:2 (pMEB097)  (1127) --------------------------------------------------
SEQ ID NO:4 (pMEB084)  (1127) --------------------------------------------------

                                      2251                                             2300
SEQ ID NO:1 (AATC1711) (2251) RHFHMDYGTGFYKPVMASKTLEAILSFARRGTIQEKLISVAGLAVHSGPD
SEQ ID NO:2 (pMEB097)  (1127) --------------------------------------------------
SEQ ID NO:4 (pMEB084)  (1127) --------------------------------------------------

                                      2301                           2333
SEQ ID NO:1 (AATC1711) (2301) EYRRLFEPFQGLFEIPSYRSLYLRWVNAVCGDA
SEQ ID NO:2 (pMEB097)  (1127) ---------------------------------
SEQ ID NO:4 (pMEB084)  (1127) ---------------------------------
```

Figure 7B

Alignment of the amino acid sequences of P1 region of the recombinant polyprotein in pMEB099 and the reference sequence (Genbank AAT01766) using the vector NTI program

```
                        1                                                 50
P1 AAT01766      (1)   -GAGQSSPATGSQNQSGNTGSIINNYYMQQYQNSMDTQLGDNATSGGSNE
 p1 pMEB099      (1)   MGAGQSSPATGSQNQSGNTSSIINGYYMQQYQNSMDTQLGDNATSGGSNE

                        51                                               100
P1 AAT01766     (50)   GSTDTTSTHTTNTQNNDWFSKLASSAFSGLFGALLADKKTEETTLLEDRI
 p1 pMEB099     (51)   GSTDTTSTHTTNIQNNDWFSKLASSAFSGLFGALLADKKTEETTLLEDRI

                        101                                              150
P1 AAT01766    (100)   LTTRNGHTTSTTQSSVGVTYGYATAEDFVSGPNTSGLETRVAQAERFFKT
 p1 pMEB099    (101)   LTTRNGHTTSTTQSSVGVTYGYATAEDFVSGPNTSGLETRVAQAERFFKT

                        151                                              200
P1 AAT01766    (150)   HLFDWVTSDPFGRCHLLELPTDHKGVYGSLTDSYAYMRNGWDVEVTAVGN
 p1 pMEB099    (151)   HLFDWVTSDPFGRCHLLELPTDHKGVYGCLTDSYAYMRNGWDVEVTAVGN

                        201                                              250
P1 AAT01766    (200)   QFNGGCLLVAMVPELCSIQKRELYQLTLFPHQFINPRTNMTAHITVPFVG
 p1 pMEB099    (201)   QFNGGCLLVAMVPELCSIQKRELYQLTLFPHQFINPRTNMTAHITVPFVG

                        251                                              300
P1 AAT01766    (250)   VNRYDQYKVHKPWTLVVMVVAPLIVNSEGAPQIKVYANIAPTNVHVAGEF
 p1 pMEB099    (251)   VNRYDQYKVHKPWTLVVMVVAPLTVNSEGAPQIKVYANIAPTNVHVAGEF

                        301                                              350
P1 AAT01766    (300)   PSKEGIFPVACSDGYGGLVTTDPKTADPAYGKVFNPPRNMLPGRFTNFLD
 p1 pMEB099    (301)   PSKEGIFPVACSDGYGGLVTTDPKTADPAYGKVFNPPKNMLPGRFTNFLD

                        351                                              400
P1 AAT01766    (350)   VAEACPTFLHFEGDVPYVTTKTDSDRVLAQFDLSLAAKHMSNTFLAGLAQ
 p1 pMEB099    (351)   VAEACPTFLHFEGDVPYVTTKTDGDRVLAQFDLSLAAKHMSNTFLAGLAQ

                        401                                              450
P1 AAT01766    (400)   YYTQYSGTINLHFMFTGPTDAKARYMIAYAPPGMEPPKTPEAAAHCIHAE
 p1 pMEB099    (401)   YYTQYSGTINLHFMFTGPTDAKARYMIAYAPPGMEPPKTPEAAAHCIHAE

                        451                                              500
P1 AAT01766    (450)   WDTGLNSKFTFSIPYLSAADYAYTASDTAETTNVQGWVCLFQITHGKADG
 p1 pMEB099    (451)   WDTGLNSKFTFSIPYLSAADYAYTASDTAETTNVQGWVCLFQITHGKADG

                        501                                              550
P1 AAT01766    (500)   DALVVLASAGKDFELRLPVDARTQTTSAGESADPVTATVENYGGETQVQR
 p1 pMEB099    (501)   DALVVLASAGKDFELRLPVDARTQTTSAGESADPVTATVENYGGETQVQR

                        551                                              600
P1 AAT01766    (550)   RQHTDVSFILDRFVKVTPKDQINVLDLMQTPAHTLVGALLRTATYYFADL
 p1 pMEB099    (551)   RQHTDVSFILDRFVKVTPKDQINVLDLMQTPAHTLVGALLRTATYYFADL
```

Figure 7B (continued)

```
                        601                                               650
P1 AAT01766    (600)  EVAVKHEGRLTWVPNGAPEAALDNTTNPTAYHKAPLTPLALFYTAPHPVL
 p1 pMEB099    (601)  EVAVKHEGRLTWVPNGAPEAALDNTTNPTAYRKAPLTRLALFYTAPHRVL

                        651                                               700
P1 AAT01766    (650)  ATVYRGNSNYSDGTVANVRGDLQVLAQKAARALPTSFNYGAIKATRVTEL
 p1 pMEB099    (651)  ATVYRGNSNYSDGTVANVRGDLQVLAQKAARALPTSFNYGAIKATRVTEL

                        701                                  737
P1 AAT01766    (700)  LYRNKPAETYCPRPLLAIHFDQARHKQKIVAPVKQLL
 p1 pMEB099    (701)  LYRNKPAETYCPRPLLAIHFDQARHKQFIVAPVKQLL
```

P1 AAT01766: SEQ ID NO:5; p1 pMEB099: part of SEQ ID NO:6

Alignment of the amino acid sequences of P1 region of the recombinant polyprotein using the vector NTI program Figure 7C (continued)

```
                                251                                               300
SEQ ID NO:10        (251) SNKYDQYALHKPWTLVVMVVSPLTVKAGGSEQIKVYMNAAPTSVHVAGEL
SEQ ID NO:12        (251) SNRYDQYASHKPWTLVVMVVSPLTTSNVSASQIKVYANNAPTSVHVAGEL
SEQ ID NO:13        (251) SNRYDQYALHKPWTLVVMVVSPLTVKAGGSEQIKVYMNAAPTSVHVAGEL
SEQ ID NO:16        (251) SNKYDQYASHKPWTLVVMVVSPLTTSNTSASQIKVYANNAPTSVHVAGEL
SEQ ID NO:2         (251) SNRYDQYASHKPWTLVVMVVSPLTTSNTSASQIKVYANNAPTSVHVAGEL
SEQ ID NO:4         (251) SNRYDQYASHKPWTLVVMVVSPLTTSNTSASQIKVYANNAPTSVHVAGEL
SEQ ID NO:8         (251) SNRYDQYASHKPWTLVVMVVSPLTTSNVSASQIKVYANNAPTSVHVAGEL

                                301                                               350
SEQ ID NO:10        (301) PSKEGIFPVACADGYGNSVTTDPKTADPAYGAVSNPPRTNLPGRPTNFLD
SEQ ID NO:12        (301) PSKEGIFPVACADGYGSSVTTDPKTADPAYGMVSNPPRTNSPGRPTNSLD
SEQ ID NO:13        (301) PSKEGIFPVACADGYGNSVTTDPKTADPAYGAVSNPPRTNLPGRPTNFLD
SEQ ID NO:16        (301) PSKEGIFPVACADGYGSSVTTDPKTADPAYGAVSNPPRTNSPGRPTNSLD
SEQ ID NO:2         (301) PSKEGIFPVACADGYGSSVTTDPKTADPAYGAVSNPPRTNSPGRPTNSLD
SEQ ID NO:4         (301) PSKEGIFPVACADGYGSSVTTDPKTADPAYGAVSNPPRTNSPGRPTNSLD
SEQ ID NO:8         (301) PSKEGIFPVACADGYGSSVTTDPKTADPAYGMVSNPPRTNSPGRPTNSLD

                                351                                               400
SEQ ID NO:10        (351) VAEACPTFLRFG-EVPSVKTVNSGDRLLAKFDASLAAGHMSNTYLSGSAQ
SEQ ID NO:12        (351) VAEACPTFLSPSSSSPSVVTSSSSQRLLAKFDASLAASHMSNTYLSGSAQ
SEQ ID NO:13        (351) VAEACPTFLRFG-EVPSVKTVNSGDRLLAKFDASLAAGHMSNTYLSGSAQ
SEQ ID NO:16        (351) VAEACPTFLSPSSSKPSVTTSSSSTRLLAKFDASLAASHMSNTYLSGSAQ
SEQ ID NO:2         (351) VAEACPTFLSPSSSKPSVTTSSSSTRLLAKFDASLAASHMSNTYLSGSAQ
SEQ ID NO:4         (351) VAEACPTFLSPSSSKPSVTTSSSSTRLLAKFDASLAASHMSNTYLSGSAQ
SEQ ID NO:8         (351) VAEACPTFLSPSSSKPSVVTSSSSQRLLAKFDASLAASHMSNTYLSGSAQ

                                401                                               450
SEQ ID NO:10        (400) YYAQYSGTSNSHFMFTGPTDSKARYMVAYSPP-GMTPPTDPEHAAHCIHS
SEQ ID NO:12        (401) YYAQYSGTSNSHFMFTGSTDSKARYMVAYSPPSSSTPPSSSPESAAHCIHS
SEQ ID NO:13        (400) YYAQYSGTSNSHFMFTGPTDSKARYMVAYSPP-GMTPPTDPEHAAHCIHS
SEQ ID NO:16        (401) YYAQYSGTSNSHFMFTGSTDSKARYMVAYSPPSSSTPPSSSPESAAHCIHS
SEQ ID NO:2         (401) YYAQYSGTSNSHFMFTGSTDSKARYMVAYSPPSSSTPPSSSPESAAHCIHS
SEQ ID NO:4         (401) YYAQYSGTSNSHFMFTGSTDSKARYMVAYSPPSSSTPPSSSPESAAHCIHS
SEQ ID NO:8         (401) YYAQYSGTSNSHFMFTGSTDSKARYMVAYSPPSSSTPPSSSPESAAHCIHS

                                451                                               500
SEQ ID NO:10        (449) EWDTGLNSKFTFSIPYSSAADYAYTASDSAETSSVQGWVCIYQITHGKAE
SEQ ID NO:12        (451) EWDTGLNSKFTFSIPYSSAADYAYTASDSAETSSVQGWVCIYQITHGKAE
SEQ ID NO:13        (449) EWDTGLNSKFTFSIPYSSAADYAYTASDSAETSSVQGWVCIYQITHGKAE
SEQ ID NO:16        (451) EWDTGLNSKFTFSIPYSSAADYAYTASDTAETISVQGWVCIYQITHGKAE
SEQ ID NO:2         (451) EWDTGLNSKFTFSIPYSSAADYAYTASDTAETISVQGWVCIYQITHGKAE
SEQ ID NO:4         (451) EWDTGLNSKFTFSIPYSSAADYAYTASDTAETISVQGWVCIYQITHGKAE
SEQ ID NO:8         (451) EWDTGLNSKFTFSIPYSSAADYAYTASDSAETSSVQGWVCIYQITHGKAE

                                501                                               550
SEQ ID NO:10        (499) GDALVVSVSAGKDFEFPLPSDAPSQTTSTGESADPVTTTVENYGGETQTA
SEQ ID NO:12        (501) SDSLVVSVSAGKDFESRLPSDSKSQTTSTGESADPVTTTVENYGGETQSS
SEQ ID NO:13        (499) GDALVVSVSAGKDFEFRLPSDARSQTTSTGESADPVTTTVENYGGETQTA
SEQ ID NO:16        (501) SDSLVVSVSAGKDFESRLPSDSRSQTTATGESADPVTTTVENYGGETQSS
SEQ ID NO:2         (501) SDSLVVSVSAGKDFESPLPSDSPSQTTATGESADPVTTTVENYGGETQSS
SEQ ID NO:4         (501) SDSLVVSVSAGKDFESRLPSDSRSQTTATGESADPVTTTVENYGGETQSS
SEQ ID NO:8         (501) SDSLVVSVSAGKDFESRLPSDSKSQTTSTGESADPVTTTVENYGGETQSS
```

Figure 7C (continued)

```
                         551                                              600
SEQ ID NO:10     (549)   RRLHTDVAFIQDRFVKETKPKNIQTVDLMQIPSHTLVGALLRTATYYFSD
SEQ ID NO:12     (551)   RRQHTDVTFIMDRFVKIQNINGTHKVDLMQTQQHQLVGALLSTATYYFSD
SEQ ID NO:13     (549)   RRLHTDVAFIQDRFVKETKPKNIQTVDLMQIPSHTLVGALLRTATYYFSD
SEQ ID NO:16     (551)   RRHHTDVAFIMDRFVKIQKESGTHKVDLMQAKQHQLVGALLRTATYYFSD
SEQ ID NO:2      (551)   RRHHTDVAFIMDRFVKIQKESGTHKVDLMQAKQHQLVGALLSTATYYFSD
SEQ ID NO:4      (551)   RRHHTDVAFIMDRFVKIQKESGTHKVDLMQAKQHQLVGALLRTATYYFSD
SEQ ID NO:8      (551)   RRQHTDVTFIMDRFVKIQNINGTHKVDLMQTQQHQLVGALLRTATYYFSD

                         601                                              650
SEQ ID NO:10     (599)   LEVAKVKTGPQTWVFNGAPKDALNNQTNPTAYELQPITRLALPYTAPHRV
SEQ ID NO:12     (601)   LEQVWRKAGSQTWVFNGAPQSALSNQGNPTAYLFAPQTRLALPYTAPHRV
SEQ ID NO:13     (599)   LEVAKVKTGPQTWVFNGAPKDALNNQTNPTAYEKQPITRLALPYTAPHRV
SEQ ID NO:16     (601)   LEQVWRKAGSQTWVFNGAPQSALLNQTNPTAYEKAPQTRLALPYTAPHRV
SEQ ID NO:2      (601)   LEQVWRKAGSQTWVFNGAPQSALLNQTNPTAYEKAPQTRLALPYTAPHRV
SEQ ID NO:4      (601)   LEQVWRKAGSQTWVFNGAPQSALLNQTNPTAYEKAPQTRLALPYTAPHRV
SEQ ID NO:8      (601)   LEQVWRKAGSQTWVFNGAPQSALSNQGNPTAYLFAPQTRLALPYTAPHRV

                         651                                              700
SEQ ID NO:10     (649)   LATVYRGKTAYCETTE-RPGDGQSLAQRGQAPLPTSFNECASAAQPITEL
SEQ ID NO:12     (651)   LATVYNGQAKYEACGQPRRGDKSFLAERVQQLPASFNDCAAQATELIKEL
SEQ ID NO:13     (649)   LATVYNGKTAYGETTE-RRGDGQSLAQRGQARLPTSFNECASAAQPITEL
SEQ ID NO:16     (651)   LATVYRGQAKYEVCGQPRPGDKQSLAERVKQLPASFNDCAAQAQAIKEL
SEQ ID NO:2      (651)   LATVYNGQAKYEVCGQPRRGDKQSLAERVKQLPASFNDCAAQAQAIKEL
SEQ ID NO:4      (651)   LATVYNGQAKYEVCGQPRRGDKQSLAERVKQLPASFNDCAAQAQAIKEL
SEQ ID NO:8      (651)   LATVYRGQAKYEACGQPRPGDKSFLAERVQQLPASFNDCAAQATELIKEL

                         701                                              750
SEQ ID NO:10     (698)   LVRMKRAETYCPRPLLAQRTE-QDRRKQEIIAPEKQKLNFDLLKLAGDVE
SEQ ID NO:12     (701)   LKPMKRAEKYCPRPLLAEREQQDRRKQKIIAPEKQELNFDLLKLAGDVE
SEQ ID NO:13     (698)   LVRMKRAETYCPRPLLAQRTE-QDRRKQEIIAPEKQKLNFDLLKLAGDVE
SEQ ID NO:16     (701)   LVRMKRAEKYCPRPLLAERVEQDRRKQKIIAPEKQELNFDLLKLAGDVE
SEQ ID NO:2      (701)   LKPMKRAEKYCPRPLLAEREQQDRRKQKIIAPEKQELNFDLLKLAGDVE
SEQ ID NO:4      (701)   LVRMKRAEKYCPRPLLAERVEQDRRKQKIIAPEKQELNFDLLKLAGDVE
SEQ ID NO:8      (701)   LVRMKRAEKYCPRPLLAEREQQDRRKQKIIAPEKQELNFDLLKLAGDVE

                         751                                              800
SEQ ID NO:10     (747)   SNPGPFFFADVRSNFSKLVDTINQMQEDMSTKHGPDFNRLVSAFEELATG
SEQ ID NO:12     (751)   SNPGPFFFADVRSNFSKLVDTINQMQEDMSTKHGPDFNRLVSAFEELATG
SEQ ID NO:13     (747)   SNPGPFFFADVRSNFSKLVDTINQMQEDMSTKHGPDFNRLVSAFEELATG
SEQ ID NO:16     (751)   SNPGPFFFADVRSNFSKLVDTINQMQEDMSTKHGPDFNRLVSAFEELATG
SEQ ID NO:2      (751)   SNPGPFFFADVRSNFSKLVDTINQMQEDMSTKHGPDFNRLVSAFEELATG
SEQ ID NO:4      (751)   SNPGPFFFADVRSNFSKLVDTINQMQEDMSTKHGPDFNRLVSAFEELATG
SEQ ID NO:8      (751)   SNPGPFFFADVRSNFSKLVDTINQMQEDMSTKHGPDFNRLVSAFEELATG

                         801                                              850
SEQ ID NO:10     (797)   VKAIRTGLDEAKPWYKLIKLLSRLSCMAAVAARSKDPVLVAIMLADTGLE
SEQ ID NO:12     (801)   VKAIPTGLDEAKPWYKLIKLLSRLSCMAAVAARSKDPVLVAIMLADTGLE
SEQ ID NO:13     (797)   VKAIRTGLDEAKPWYKLIKLLSRLSCMAAVAARSKDPVLVAIMLADTGLE
SEQ ID NO:16     (801)   VKAIRTGLDEAKPWYKLIKLLSRLSCMAAVAARSKDPVLVAIMLADTGLE
SEQ ID NO:2      (801)   VKAIPTGLDEAKPWYKLIKLLSRLSCMAAVAARSKDPVLVAIMLADTGLE
SEQ ID NO:4      (801)   VKAIRTGLDEAKPWYKLIKLLSRLSCMAAVAARSKDPVLVAIMLADTGLE
SEQ ID NO:8      (801)   VKAIRTGLDEAKPWYKLIKLLSRLSCMAAVAARSKDPVLVAIMLADTGLE
```

Figure 7C (continued)

```
                          851                                              900
SEQ ID NO:10      (847)   --------------------------------------------------
SEQ ID NO:12      (851)   --------------------------------------------------
SEQ ID NO:13      (847)   --------------------------------------------------
SEQ ID NO:16      (851)   ILDSTFVVKKISDSLSSLFHVPAPVFSFGAPILLAGLVKVASSFFRSTPE
SEQ ID NO:2       (851)   --------------------------------------------------
SEQ ID NO:4       (851)   --------------------------------------------------
SEQ ID NO:8       (851)   --------------------------------------------------

                          901                                              950
SEQ ID NO:10      (847)   --------RQRPLKVRAKLPQQEGPYAGPLERQKPLKVKAKAPVVKEGPY
SEQ ID NO:12      (851)   --------RQRPLKVRAKLPQQEGPYAGPLERQKPLKVKAKAPVVKEGPY
SEQ ID NO:13      (847)   --------RQRPLKVRAKLPQQEGPYAGPLERQKPLKVKAKAPVVKEGPY
SEQ ID NO:16      (901)   DLERAEKQRQRPLKVRAKLPQQEGPYAGPLERQKPLKVKAKAPVVKEGPY
SEQ ID NO:2       (851)   --------RQRPLKVRAKLPQQEGPYAGPLERQKPLKVKAKAPVVKEGPY
SEQ ID NO:4       (851)   --------RQRPLKVRAKLPQQEGPYAGPLERQKPLKVKAKAPVVKEGPY
SEQ ID NO:8       (851)   --------RQRPLKVRAKLPQQEGPYAGPLERQKPLKVKAKAPVVKEGPY

                          951                                             1000
SEQ ID NO:10      (889)   EGPVKKPVALKVKAKNLIVTESGAPPTDLQKMVMGNTKPVELIILDGKTVA
SEQ ID NO:12      (893)   EGPVKKPVALKVKAKNLIVTESGAPPTDLQKMVMGNTKPVELIILDGKTVA
SEQ ID NO:13      (889)   EGPVKKPVALKVKAKNLIVTESGAPPTDLQKMVMGNTKPVELIILDGKTVA
SEQ ID NO:16      (951)   EGPVKKPVALKVKAKNLIVTESGAPPTDLQKMVMGNTKPVELIILDGKTVA
SEQ ID NO:2       (893)   EGPVKKPVALKVKAKNLIVTESGAPPTDLQKMVMGNTKPVELIILDGKTVA
SEQ ID NO:4       (893)   EGPVKKPVALKVKAKNLIVTESGAPPTDLQKMVMGNTKPVELIILDGKTVA
SEQ ID NO:8       (893)   EGPVKKPVALKVKAKNLIVTESGAPPTDLQKMVMGNTKPVELIILDGKTVA

                          1001                                            1050
SEQ ID NO:10      (939)   ICCATGVFGTAYLVPRHLFAEKYDKIMLDGRAMTDSDYRVFEFEIKVKGQ
SEQ ID NO:12      (943)   ICCATGVFGTAYLVPRHLFAEKYDKIMLDGRAMTDSDYRVFEFEIKVKGQ
SEQ ID NO:13      (939)   ICCATGVFGTAYLVPRHLFAEKYDKIMLDGRAMTDSDYRVFEFEIKVKGQ
SEQ ID NO:16     (1001)   ICCATGVFGTAYLVPRHLFAEKYDKIMLDGRAMTDSDYRVFEFEIKVKGQ
SEQ ID NO:2       (943)   ICCATGVFGTAYLVPRHLFAEKYDKIMLDGRAMTDSDYRVFEFEIKVKGQ
SEQ ID NO:4       (943)   ICCATGVFGTAYLVPRHLFAEKYDKIMLDGRAMTDSDYRVFEFEIKVKGQ
SEQ ID NO:8       (943)   ICCATGVFGTAYLVPRHLFAEKYDKIMLDGRAMTDSDYRVFEFEIKVKGQ

                          1051                                            1100
SEQ ID NO:10      (989)   DMLSDAALMVLHRGNRVRDITKHFRDTARMKKGTPVVGVVNNADVGRLIF
SEQ ID NO:12      (993)   DMLSDAALMVLHRGNRVRDITKHFRDTARMKKGTPVVGVVNNADVGRLIF
SEQ ID NO:13      (989)   DMLSDAALMVLHRGNRVRDITKHFRDTARMKKGTPVVGVVNNADVGRLIF
SEQ ID NO:16     (1051)   DMLSDAALMVLHRGNPVRDITKHFRDTARMKKGTPVVGVVNNADVGRLIF
SEQ ID NO:2       (993)   DMLSDAALMVLHRGNPVRDITKHFRDTARMKKGTPVVGVVNNADVGRLIF
SEQ ID NO:4       (993)   DMLSDAALMVLHRGNRVRDITKHFRDTARMKKGTPVVGVVNNADVGRLIF
SEQ ID NO:8       (993)   DMLSDAALMVLHRGNRVRDITKHFRDTARMKKGTPVVGVVNNADVGRLIF

                          1101                                            1150
SEQ ID NO:10     (1039)   SGEALTYKDIVV[illegible]MDGDTMPGLFAYKAATKAGYCGGAVLAKDGADTFIVG
SEQ ID NO:12     (1043)   SGEALTYKDIVV[illegible]MDGDTNPGLFAYKAATKAGYCGGAVLAKDGADTFIVG
SEQ ID NO:13     (1039)   SGEALTYKDIVV[illegible]MDGDTNPGLFAYKAATKAGYCGGAVLAKDGADTFIVG
SEQ ID NO:16     (1101)   SGEALTYKDIVVTMDGDTNPGLFAYKAATKAGYCGGAVLAKDGADTFIVG
SEQ ID NO:2      (1043)   SGEALTYKDIVV[illegible]MDGDTNPGLFAYKAATKAGYCGGAVLAKDGADTFIVG
SEQ ID NO:4      (1043)   SGEALTYKDIVV[illegible]MDGDTNPGLFAYKAATKAGYCGGAVLAKDGADTFIVG
SEQ ID NO:8      (1043)   SGEALTYKDIVV[illegible]MDGDTNPGLFAYKAATKAGYCGGAVLAKDGADTFIVG
```

Figure 7C (continued)

| | | 1151 1184 |
|---|---|---|
| SEQ ID NO:10 | (1089) | THSAGGNGVGYCSCVSRSMLLRMKAHVDPEPQHE |
| SEQ ID NO:12 | (1093) | THSAGGNGVGYCSCVSRSMLLRMKAHVDPEPQHE |
| SEQ ID NO:13 | (1089) | THSAGGNGVGYCSCVSRSMLLRMKAHVDPEPQHE |
| SEQ ID NO:16 | (1151) | THSAGGNGVGYCSCVSRSMLLRMKAHVDPEPQHE |
| SEQ ID NO:2 | (1093) | THSAGGNGVGYCSCVSRSMLLRMKAHVDPEPQHE |
| SEQ ID NO:4 | (1093) | THSAGGNGVGYCSCVSRSMLLRMKAHVDPEPQHE |
| SEQ ID NO:8 | (1093) | THSAGGNGVGYCSCVSRSMLLRMKAHVDPEPQHE |

Figure 7D

```
                     1                                                50
SEQ ID NO:16    (1)  MGAGQSSPATGSQNQSGNTGSIINNYYMQQYQNSMDTQLGDNAISGGSNE
SEQ ID NO:2     (1)  MSAGQKSPATGSQKQSGNTGSIINNYYMQQYQNSMDTQLGDNAISGGSNE
SEQ ID NO:4     (1)  MGAGQSSPATGSQNQSGNTGSIINNYYMQQYQNSMDTQLGDNAISGGSNE

                     51                                              100
SEQ ID NO:16   (51)  GSTDTTSTHTTNTQNNDWFSKLASSAFTGLFGALLADKKTEETTLLEDRI
SEQ ID NO:2    (51)  GSTDTTSTHTTNTQNNDWFSKLASSAFTGLFGALLADKKTEETTLLEDRI
SEQ ID NO:4    (51)  GSTDTTSTHTTNTQNNDWFSKLASSAFTGLFGALLADKKTEETTLLEDRI

                     101                                             150
SEQ ID NO:16  (101)  LTTRNGHTTSTTQSSVGVTHGYSTEEDHVAGPNTSGLETRVVQAERFYKK
SEQ ID NO:2   (101)  LTTRNGHTTSTTQSSVGVTHGYSTEEDHVAGPNTSGLETRVVQAERFYKK
SEQ ID NO:4   (101)  LTTRNGHTTSTTQSSVGVTHGYSTEEDHVAGPNTSGLETRVVQAERFYKK

                     151                                             200
SEQ ID NO:16  (151)  YLFDWTTDKAFGHLEKLELPSDHHGVFGHLVDSYAYMRNGWDVEVSAVGN
SEQ ID NO:2   (151)  YLFDWTTDKAFGHLEKLELPSDHHGVFGHLVDSYAYMRNGWDVEVSAVGN
SEQ ID NO:4   (151)  YLFDWTTDKAFGHLEKLELPSDHHGVFGHLVDSYAYMRNGWDVEVSAVGN

                     201                                             250
SEQ ID NO:16  (201)  QFNGGCLLVAMVPEWKEFDTPEKYQLTLFPHQFISPRTNMTAHITVPYLG
SEQ ID NO:2   (201)  QFNGGCLLVAMVPEWKEFDTPEKYQLTLFPHQFISPRTNMTAHITVPYLG
SEQ ID NO:4   (201)  QFNGGCLLVAMVPEWKEFDTPEKYQLTLFPHQFISPRTNMTAHITVPYLG

                     251                                             300
SEQ ID NO:16  (251)  VNRYDQYKKHKPWTLVVMVVSPLTVNNTSAAQIKVYANIAPTYVHVAGEL
SEQ ID NO:2   (251)  VNRYDQYKKHKPWTLVVMVVSPLTVNNTSAAQIKVYANIAPTYVHVAGEL
SEQ ID NO:4   (251)  VNRYDQYKKHKPWTLVVMVVSPLTVNNTSAAQIKVYANIAPTYVHVAGEL

                     301                                             350
SEQ ID NO:16  (301)  PSKEGIFPVACADGYGGLVTTDPKTADPAYGKVYNPPRTNYPGRFTNLLD
SEQ ID NO:2   (301)  PSKEGIFPVACADGYGGLVTTDPKTADPAYGKVYNPPRTNYPGRFTNLLD
SEQ ID NO:4   (301)  PSKEGIFPVACADGYGGLVTTDPKTADPAYGKVYNPPRTNYPGRFTNLLD

                     351                                             400
SEQ ID NO:16  (351)  VAEACPTFLCFDDGKPYVTTRTDDTRLLAKFDLSLAAKHMSNTYLSGIAQ
SEQ ID NO:2   (351)  VAEACPTFLCFDDGKPYVTTRTDDTRLLAKFDLSLAAKHMSNTYLSGIAQ
SEQ ID NO:4   (351)  VAEACPTFLCFDDGKPYVTTRTDDTRLLAKFDLSLAAKHMSNTYLSGIAQ

                     401                                             450
SEQ ID NO:16  (401)  YYTQYSGTINLHFMFTGSTDSKARYMVAYIPPGVETPPDTPERAAHCIHA
SEQ ID NO:2   (401)  YYTQYSGTINLHFMFTGSTDSKARYMVAYIPPGVETPPDTPERAAHCIHA
SEQ ID NO:4   (401)  YYTQYSGTINLHFMFTGSTDSKARYMVAYIPPGVETPPDTPERAAHCIHA

                     451                                             500
SEQ ID NO:16  (451)  EWDTGLNSKFTFSIPYVSAADYAYTASDTASTINVQGWVCIYQITHGKAE
SEQ ID NO:2   (451)  EWDTGLNSKFTFSIPYVSAADYAYTASDTASTINVQGWVCIYQITHGKAE
SEQ ID NO:4   (451)  EWDTGLNSKFTFSIPYVSAADYAYTASDTASTINVQGWVCIYQITHGKAE

                     501                                             550
SEQ ID NO:16  (501)  NDTLVVSVSAGKDFELRLPIDPRQQTTATGESADPVTTTVENYGGETQIQ
SEQ ID NO:2   (501)  NDTLVVSVSAGKDFELRLPIDPRQQTTATGESADPVTTTVENYGGETQIQ
SEQ ID NO:4   (501)  NDTLVVSVSAGKDFELRLPIDPRQQTTATGESADPVTTTVENYGGETQIQ

                     551                                             600
SEQ ID NO:16  (551)  RRHHTDIGFIMDRFVKIQSLSPTHVIDLMQAHQHGLVGALLRAATYYFSD
SEQ ID NO:2   (551)  RRHHTDIGFIMDRFVKIQSLSPTHVIDLMQAHQHGLVGALLRAATYYFSD
SEQ ID NO:4   (551)  RRHHTDIGFIMDRFVKIQSLSPTHVIDLMQAHQHGLVGALLRAATYYFSD

                     601                                             650
SEQ ID NO:16  (601)  LEIVVRHEGNLTWVPNGAPESALLNTSNPTAYNKAPFTRLALPYTAPHRV
SEQ ID NO:2   (601)  LEIVVRHEGNLTWVPNGAPESALLNTSNPTAYNKAPFTRLALPYTAPHRV
SEQ ID NO:4   (601)  LEIVVRHEGNLTWVPNGAPESALLNTSNPTAYNKAPFTRLALPYTAPHRV
```

Figure 7D (continued)

```
                     651                                              700
SEQ ID NO:16  (651)  LATVYNGTSKYAVGGSGPRGDMGSLAAPVVKQLPASFNYGAIKADAIHEL
SEQ ID NO:2   (651)  LATVYNGTSKYAVGGSGRRGDMGSLAARVVKQLPASFNYGAIKADAIHEL
SEQ ID NO:4   (651)  LATVYNGTSKYAVGGSGPRGDMGSLAAPVVKQLPASFNYGAIKADAIHEL

                     701                                              750
SEQ ID NO:16  (701)  LVKSNKAELYCPRPLLAIEVSSQDRHKQRIIAPAKQLLNFDLLKLAGDVE
SEQ ID NO:2   (701)  LVEMKRAELYCPPPLLAIEVSSQDPHKQKIIAIAKQLLKFDLLKLAGDVE
SEQ ID NO:4   (701)  LVKSNKAELYCPRPLLAIEVSSQDRHKQRIIAPAKQLLNFDLLKLAGDVE

                     751                                              800
SEQ ID NO:16  (751)  SNPGPFFFADVRSNFSKLVDTINQMQEDMSTKHGFDFNRLVSAFEELATG
SEQ ID NO:2   (751)  SNPGPFFFADVRSNFSKLVDTINQMQEDMSTKHGFDFNRLVSAFEELATG
SEQ ID NO:4   (751)  SNPGPFFFADVRSNFSKLVDTINQMQEDMSTKHGFDFNRLVSAFEELATG

                     801                                              850
SEQ ID NO:16  (801)  VKAIRTGLDEAKPWYKLIKLLSRLSCMAAVAARSKDPVLVAIMLADTGLE
SEQ ID NO:2   (801)  VKAIRTGLDEAFPWYKLIKLLSKLSCMAAVAARSKDPVLVAIMLADTGLE
SEQ ID NO:4   (801)  VKAIRTGLDEAKPWYKLIKLLSRLSCMAAVAARSKDPVLVAIMLADTGLE

                     851                                              900
SEQ ID NO:16  (851)  ILDSTFVVKKISDSLSSLFHVPAPVFSFGAPILLAGLVKVASSFFRSTPE
SEQ ID NO:2   (851)  --------------------------------------------------
SEQ ID NO:4   (851)  --------------------------------------------------

                     901                                              950
SEQ ID NO:16  (901)  DLERAEKQRQRPLEVKAKLPQQSGPYAGPLERQKPLKVEARAPVVKEGPY
SEQ ID NO:2   (851)  ---------RQRPLKVKAPLPQQEGPYAGPLERQKPLKVKAKAPVVKEGPY
SEQ ID NO:4   (851)  ---------RQRPLEVKAKLPQQSGPYAGPLERQKPLKVEARAPVVKEGPY

                     951                                             1000
SEQ ID NO:16  (951)  EGPVKKPVALKVKAKNLIVTESGAPPTDLQKMVMGNTKPVELILDGKTVA
SEQ ID NO:2   (893)  EQPVKKPVALNVKAKNLIVTEGSAPPTDLQKMVMGNTKPVELILDGKTVA
SEQ ID NO:4   (893)  EGPVKKPVALKVKAKNLIVTESGAPPTDLQKMVMGNTKPVELILDGKTVA

                     1001                                            1050
SEQ ID NO:16 (1001)  ICCATGVFGTAYLVPRHLFAEKYDKIMLDGRAMTDSDYRVFEFEIKVKGQ
SEQ ID NO:2   (943)  ICCATGVFGTAYLVPRHLFAEKYDKIMLDGRAMTDSDYRVFEFEIKVKGQ
SEQ ID NO:4   (943)  ICCATGVFGTAYLVPRHLFAEKYDKIMLDGRAMTDSDYRVFEFEIKVKGQ

                     1051                                            1100
SEQ ID NO:16 (1051)  DMLSDAALMVLHPGNRVRDITKHFRDTARMKKGTPVVGVVNNADVGRLIF
SEQ ID NO:2   (993)  DMLSDAALMVLHKGNRVRDITKHFRDTARMKKGTPVVGVVNNADVGRLIF
SEQ ID NO:4   (993)  DMLSDAALMVLHPGNRVRDITKHFRDTARMKKGTPVVGVVNNADVGRLIF

                     1101                                            1150
SEQ ID NO:16 (1101)  SGEALTYKDIVVTMDGDTMPGLFAYKAATKAGYCGGAVLAKDGADTFIVG
SEQ ID NO:2  (1043)  SGEALTYKDIVV[illegible]MDGDTMPGLFAYKAATKAGYCGGAVLAKDGADTFIVG
SEQ ID NO:4  (1043)  SGEALTYKDIVV[illegible]MDGDTMPGLFAYKAATKAGYCGGAVLAKDGADTFIVG

                     1151                            1184
SEQ ID NO:16 (1151)  THSAGGNGVGYCSCVSRSMLLRMFAEVDPEPQHE
SEQ ID NO:2  (1093)  THSAGGNGVGYCSCVSRSMLLRMKAEVDPEPQHE
SEQ ID NO:4  (1093)  THSAGGNGVGYCSCVSRSMLLRMFAEVDPEPQHE
```

FMDV VLPs

| Batch Size | Titer[a] (Log10CCID$_{50}$/mL) | ELISA M326/M326→146S[b] (Log10CCID$_{50}$/mL) | EM (VLPs/mL) |
|---|---|---|---|
| 150 L | 7.14 | 2.19; *2.14 (heated)* | 5 x $10^{9}$ [c] |
| 4 L | 7.17 | 2.09; *1.89 (heated)* | 2 x $10^{9}$ [d] |

a: supernatant D3 1xC
b: supernatant D5 1xC
c: supernatant D5 concentrated 12.8 x g (CENTRICON tube)
d: supernatant D5 concentrated 9.5 x g (VIVAFLOW)

The evolution of mean FMDV A24 Cruzeiro neutralizing antibody titers

G1: Lemna; G2: Baculovirus;
G3: vCP2186; G4 Controls

Figure 10

FMDV A24 Cruzeiro neutralizing antibody titers

| Group | Cattle | FMD A24 Cruzeiro neutralizing titre (Log10 PD50) | | | |
|---|---|---|---|---|---|
| | | D0 | D21 | D25* | D28* |
| 1 (Lemna-FMDV PE 5X) | 3953 | 0.60 | 0.60 | 1.95 | - |
| | 3954 | 0.75 | 0.75 | 1.80 | - |
| | 3955 | <=0.30 | 0.75 | - | 2.85 |
| | 3956 | <=0.30 | 0.90 | - | >=3.45 |
| | 3957 | 0.30 | <=0.30 | 1.95 | - |
| | Mean | <= 0.45 | <=0.66 | 1.90 | >= 3.15 |
| | *S.d.* | *0.21* | *0.23* | *0.09* | *0.42* |
| 2 (Batch n°4 Baculo 14.4xC) | 3958 | 1.05 | 1.35 | - | >=3.45 |
| | 3959 | 0.30 | 1.05 | - | 3.30 |
| | 3960 | 0.45 | 1.50 | - | 3.30 |
| | 3961 | 0.60 | 1.05 | - | 3.30 |
| | 3962 | 0.45 | 1.20 | - | >=3.45 |
| | Mean | 0.57 | 1.23 | - | >=3.36 |
| | *S.d.* | *0.29* | *0.20* | - | *0.08* |
| 3 (Batch n°1 vCP 2186-1) | 3963 | 0.30 | 0.75 | 2.70 | - |
| | 3964 | 0.30 | 0.90 | 2.25 | - |
| | 3965 | 0.60 | 1.20 | 2.25 | - |
| | 3966 | <=0.30 | 0.90 | 1.80 | - |
| | 3967 | 0.45 | <=0.30 | 1.65 | - |
| | Mean | <=0.39 | <=0.81 | 2.13 | - |
| | *S.d.* | *0.13* | *0.33* | *0.42* | - |
| 4 Control | 3932 | 0.45 | <=0.30 | - | 2.10 |
| | 3933 | 0.45 | <=0.30 | - | 2.85 |
| | Mean | 0.45 | <=0.30 | - | 2.48 |
| | *S.d.* | *0.00* | *0.00* | - | *0.53* |

G1: Lemna duckweed; G2: Baculo;
G3: vCP2186; G4 Controls)

Evolution of mean FMDV A24 Cruzeiro neutralizing antibody titers

G1: baculo filtered 2.0 mL;
G2: baculo filtered 0.5 mL;
G3: baculo filtered 0.125 mL;
G4: controls Evolution of mean FMDV A24 Cruzeiro neutralizing antibody titers G4: controls;
G5: baculo not filtered 2.0 mL;
G6: baculo not filtered 0.5 mL;
G7: vCP 2.0 mL Evolution of mean rectal temperature after challenge G1: baculo filtered 2.0 mL; G2 baculo filtered 0.5 mL;
G3: baculo filtered 0.125 mL; G4: controls Evolution of mean rectal temperature after challenge G5 baculo not filtered 2.0 mL; G6: baculo not filtered 0.5 mL; G7: vCP 2.0 mL Figure 12C
Sero-neutralization test results

| Group | Cattle | FMD A24 neutralizing titres (Log10(PD50)) | | |
|---|---|---|---|---|
| | | D0 | D21 | D28* |
| 1 Filtered BAC 2 mL | 4869 | 0.75 | 1.65 | 3.30 |
| | 4870 | < 0.30 | 1.35 | 3.15 |
| | 4871 | < 0.30 | 1.95 | 2.10 |
| | 4872 | < 0.30 | 1.35 | 3.15 |
| | 4873 | < 0.30 | 1.95 | 2.25 |
| | **Mean** | **< 0.39** | **1.65** | **2.79** |
| | *Sd* | *0.20* | *0.30* | *0.57* |
| 2 Filtered BAC 0.5 mL | 4874 | < 0.30 | 0.90 | 3.30 |
| | 4875 | < 0.30 | 1.65 | 3.30 |
| | 4876 | 1.20 | 1.20 | 3.30 |
| | 4877 | 0.60 | 1.35 | 3.00 |
| | 4878 | 0.60 | 1.20 | 2.70 |
| | **Mean** | **< 0.60** | **1.26** | **3.12** |
| | *Sd* | *0.37* | *0.27* | *0.27* |
| 3 Filtered BAC 0.125 mL | 4879 | < 0.30 | 0.75 | 3.00 |
| | 4880 | < 0.30 | 1.05 | 2.70 |
| | 4881 | 0.60 | 0.75 | 3.30 |
| | 4882 | < 0.30 | 0.75 | * 1.80 |
| | 4883 | < 0.30 | 1.35 | 1.80 |
| | **Mean** | **< 0.36** | **0.93** | **2.52** |
| | *Sd* | *0.13* | *0.27* | *0.69* |
| 4 Controls | 4884 | < 0.30 | < 0.30 | * 0.90 |
| | 4885 | 0.60 | < 0.30 | * 0.75 |
| | **Mean** | **< 0.45** | **< 0.30** | **0.83** |
| | *Sd* | *0.21* | *0.00* | *0.11* |
| 5 Not filtered BAC 2 mL | 4886 | 0.75 | 1.05 | 3.30 |
| | 4887 | 0.60 | 1.05 | 3.30 |
| | 4888 | < 0.30 | 1.50 | 2.10 |
| | 4889 | 0.75 | 1.05 | 1.50 |
| | 4890 | < 0.30 | 1.50 | 2.10 |
| | **Mean** | **< 0.54** | **1.23** | **2.46** |
| | *Sd* | *0.23* | *0.25* | *0.80* |
| 6 Not filtered BAC 0.5 mL | 4891 | < 0.30 | 1.05 | 2.70 |
| | 4892 | 0.60 | 1.05 | 3.00 |
| | 4893 | < 0.30 | 1.05 | 3.15 |
| | 4894 | < 0.30 | 0.75 | 2.70 |
| | 4895 | < 0.30 | 1.05 | 2.40 |
| | **Mean** | **< 0.36** | **0.99** | **2.79** |
| | *Sd* | *0.13* | *0.13* | *0.29* |
| 7 vCP 2 mL | 4896 | < 0.30 | 1.20 | 2.70 |
| | 4897 | < 0.30 | 1.05 | 2.40 |
| | 4898 | < 0.30 | 1.05 | 3.00 |
| | 4899 | < 0.30 | 1.20 | 3.00 |
| | 4900 | 0.60 | 1.20 | 3.00 |
| | **Mean** | **< 0.36** | **1.14** | **2.82** |

Figure 13

EM analysis of A24 Cruzeiro VLPs with (MEB097) or without (MEB084) the covalent cage mutation in the presence or absence of heat or acid

| Recombinant Baculovirus Construction | **A**<br>W/O treatment | **B**<br>1h at 56°C | **C**<br>Acidification. pH=5 |
| --- | --- | --- | --- |
| "classical A24"<br>=**BacMEB084**<br>Samples [] 4X | 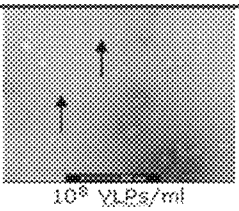<br>$10^8$ VLPs/ml | 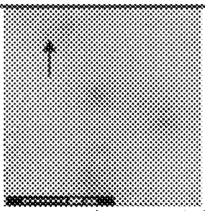<br>Only very few particles detected | No VLPs |
| "stabilized A24"<br>=**BacMEB097**<br>Samples []<br>3,3X | 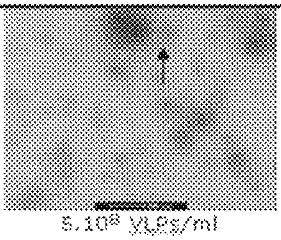<br>5.$10^8$ VLPs/ml | 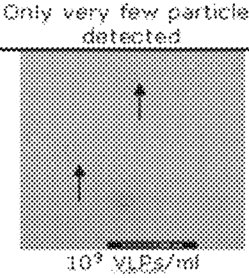<br>$10^9$ VLPs/ml | 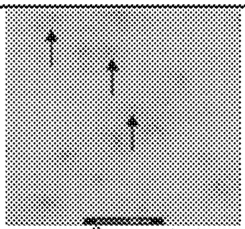<br>2.$10^9$ VLPs/ml |

Figure 14
ELISA analysis of VLPs with (MEB097) or without (MEB084) the covalent cage mutation for the A24 Cruzeiro serotype after heating
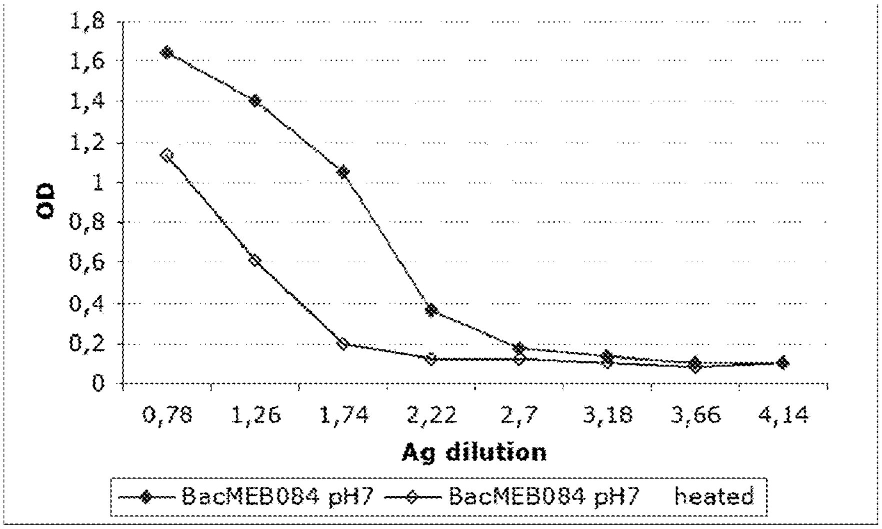
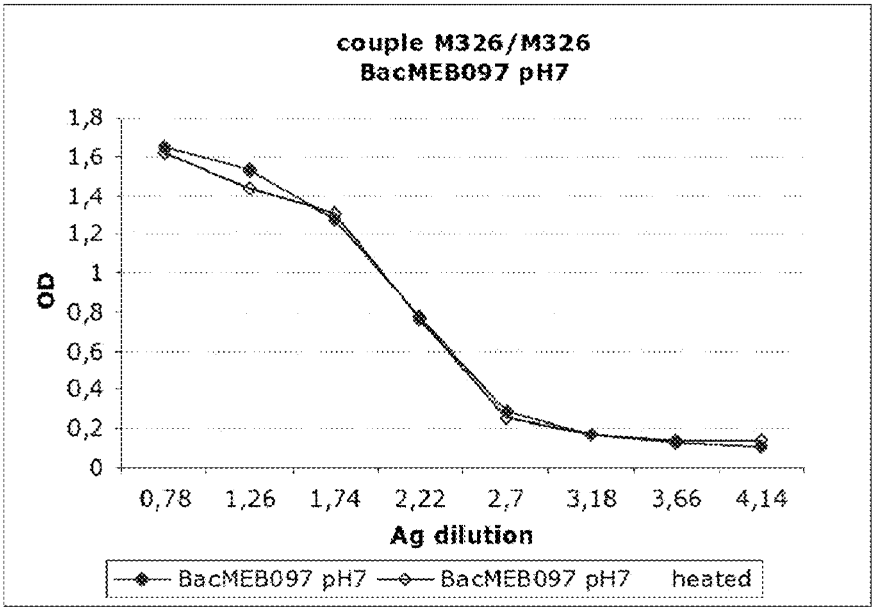

ELISA analysis of A24 Cruzeiro VLPs with (MEB097, covalent cage) or without (MEB084, wild type) the covalent cage mutation stored at 5°C over time ELISA results and EM pictures showing O1 Manisa covalent cage VLPs are resistant to heat Figure 17
ELISA results showing O1 Manisa covalent cage VLP stability in heat
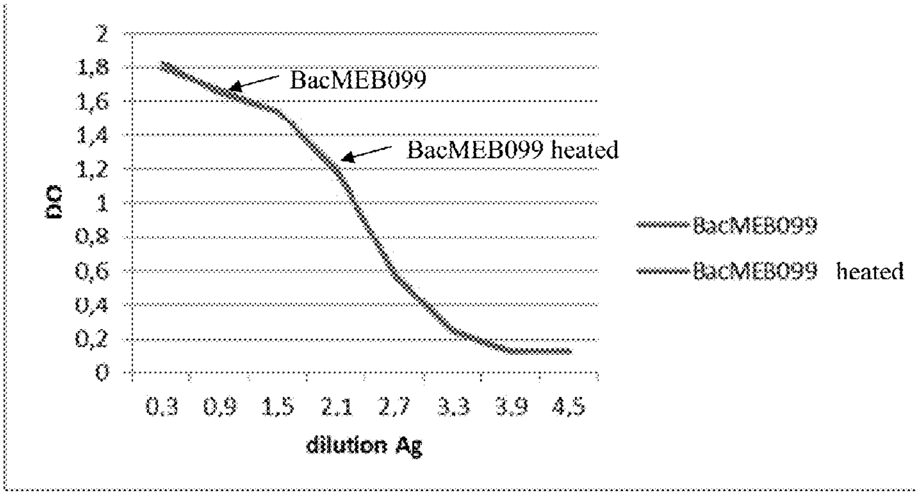
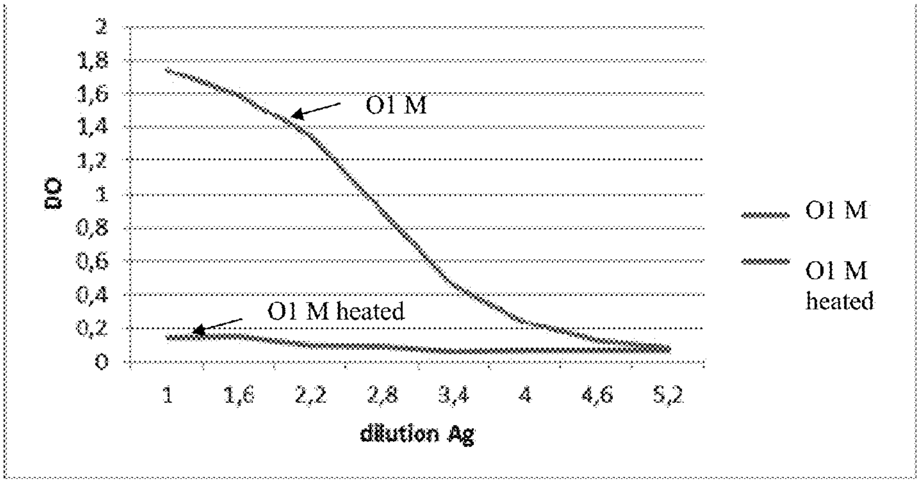

Vaccination and analysis scheme

Evolution of neutralizing antibody titers against FMD Asia1 Shamir and FMD A22 Iraq Humoral response - Memory B cells detection 7 day re-stimulation         Plate coating PBMCs → Asia1 Shamir VLP → Asia1 Shamir inactivated AI
PBMCs → Asia1 Shamir VLP → A22 Iraq inactivated AI
PBMCs → A22 Iraq VLP → Asia1 Shamir inactivated AI
PBMCs → A22 Iraq VLP → A22 Iraq inactivated AI

Figure 19B

Asia Shamir covalent cage & Iraq A22 covalent cage VLP serology data

| | | Antigens specific responses | | | |
|---|---|---|---|---|---|
| | | Asia 1 Shamir | | A22 Iraq | |
| Assay | Group ⟶ | Asia Shamir VLP +TS6 | A22 Iraq VLP +TS6 | Asia Shamir VLP +TS6 | A22 Iraq VLP +TS6 |
| IFNγ secreting cells | Peptide pool | + | - | + | + |
| IgG secreting plasma cell | Inactivated AI | ++ | - | + | + |
| IgG secreting memory B cells | Coating Asia1 shamir AI | ++ | + | + | +/- |
| | Coating A22 Iraq AI | + | + | + | ++ |

Specific IgG secreting plasma cells

Specific IgG secreting memory B cells

Specific IFNγ secreting cells

FMDV SVN log10 titer by Groups for Day 42

Mean FMDV VN log10 titer

Plasmid pAD3027 map

Western Blot of vAD3027

Lane 1: control to show VP2 (fully processed)
Lane 2: vAD3027

SEQUENCE LISTING

<160> NUMBER OF SEQ ID NOS: 20

<210> SEQ ID NO 1
<211> LENGTH: 2333
<212> TYPE: PRT
<213> ORGANISM: artificial sequence
<220> FEATURE:
<223> OTHER INFORMATION: Wild-type polyprotein of A24 Cruzeiro Strain (GenBank AAT01711)

<400> SEQUENCE: 1

Met Asn Thr Thr Asp Cys Phe Ile Ala Leu Val His Ala Ile Arg Glu
1 5 10 15

Ile Arg Ala Phe Phe Leu Pro Arg Ala Thr Gly Arg Met Glu Phe Thr
20 25 30

Leu His Asn Gly Glu Arg Lys Val Phe Tyr Ser Arg Pro Asn Asn His
35 40 45

Asp Asn Cys Trp Leu Asn Thr Ile Leu Gln Leu Phe Arg Tyr Val Gly
50 55 60

Glu Pro Phe Phe Asp Trp Val Tyr Asp Ser Pro Glu Asn Leu Thr Leu
65 70 75 80

Glu Ala Ile Glu Gln Leu Glu Glu Leu Thr Gly Leu Glu Leu His Glu
85 90 95

Gly Gly Pro Pro Ala Leu Val Ile Trp Asn Ile Lys His Leu Leu His
100 105 110

Thr Gly Ile Gly Thr Ala Ser Arg Pro Ser Glu Val Cys Met Val Asp
115 120 125

Gly Thr Asn Met Cys Leu Ala Asp Phe His Ala Gly Ile Phe Leu Lys
130 135 140

Gly Gln Glu His Ala Val Phe Ala Cys Val Thr Ser Asn Gly Trp Tyr
145 150 155 160

Ala Ile Asp Asp Glu Asp Phe Tyr Pro Trp Thr Pro Asp Pro Ser Asp
165 170 175

Val Leu Val Phe Val Pro Tyr Asp Gln Glu Pro Leu Asn Gly Glu Trp
180 185 190

Lys Thr Lys Val Gln Gln Lys Leu Lys Gly Ala Gly Gln Ser Ser Pro
195 200 205

Ala Thr Gly Ser Gln Asn Gln Ser Gly Asn Thr Gly Ser Ile Ile Asn
210 215 220

Asn Tyr Tyr Met Gln Gln Tyr Gln Asn Ser Met Asp Thr Gln Leu Gly
225 230 235 240

Asp Asn Ala Ile Ser Gly Gly Ser Asn Glu Gly Ser Thr Asp Thr Thr
245 250 255

Ser Thr His Thr Thr Asn Thr Gln Asn Asn Asp Trp Phe Ser Lys Leu
260 265 270

Ala Ser Ser Ala Phe Thr Gly Leu Phe Gly Ala Leu Leu Ala Asp Lys
275 280 285

Lys Thr Glu Glu Thr Thr Leu Leu Glu Asp Arg Ile Leu Thr Thr Arg
290 295 300

Asn Gly His Thr Thr Ser Thr Thr Gln Ser Ser Val Gly Val Thr His
305 310 315 320

Gly Tyr Ser Thr Glu Glu Asp His Val Ala Gly Pro Asn Thr Ser Gly
325 330 335

Leu Glu Thr Arg Val Val Gln Ala Glu Arg Phe Tyr Lys Lys Tyr Leu
340 345 350

-continued

```
Phe Asp Trp Thr Thr Asp Lys Ala Phe Gly His Leu Glu Lys Leu Glu
        355                 360                 365

Leu Pro Ser Asp His His Gly Val Phe Gly His Leu Val Asp Ser Tyr
    370                 375                 380

Ala Tyr Met Arg Asn Gly Trp Asp Val Glu Val Ser Ala Val Gly Asn
385                 390                 395                 400

Gln Phe Asn Gly Gly Cys Leu Leu Val Ala Met Val Pro Glu Trp Lys
                405                 410                 415

Glu Phe Asp Thr Arg Glu Lys Tyr Gln Leu Thr Leu Phe Pro His Gln
            420                 425                 430

Phe Ile Ser Pro Arg Thr Asn Met Thr Ala His Ile Thr Val Pro Tyr
        435                 440                 445

Leu Gly Val Asn Arg Tyr Asp Gln Tyr Lys Lys His Lys Pro Trp Thr
    450                 455                 460

Leu Val Val Met Val Val Ser Pro Leu Thr Val Asn Asn Thr Ser Ala
465                 470                 475                 480

Ala Gln Ile Lys Val Tyr Ala Asn Ile Ala Pro Thr Tyr Val His Val
                485                 490                 495

Ala Gly Glu Leu Pro Ser Lys Glu Gly Ile Phe Pro Val Ala Cys Ala
            500                 505                 510

Asp Gly Tyr Gly Gly Leu Val Thr Thr Asp Pro Lys Thr Ala Asp Pro
        515                 520                 525

Ala Tyr Gly Lys Val Tyr Asn Pro Pro Arg Thr Asn Tyr Pro Gly Arg
    530                 535                 540

Phe Thr Asn Leu Leu Asp Val Ala Glu Ala Cys Pro Thr Phe Leu Cys
545                 550                 555                 560

Phe Asp Asp Gly Lys Pro Tyr Val Thr Thr Arg Thr Asp Asp Thr Arg
                565                 570                 575

Leu Leu Ala Lys Phe Asp Leu Ser Leu Ala Ala Lys His Met Ser Asn
            580                 585                 590

Thr Tyr Leu Ser Gly Ile Ala Gln Tyr Tyr Thr Gln Tyr Ser Gly Thr
        595                 600                 605

Ile Asn Leu His Phe Met Phe Thr Gly Ser Thr Asp Ser Lys Ala Arg
    610                 615                 620

Tyr Met Val Ala Tyr Ile Pro Pro Gly Val Glu Thr Pro Pro Asp Thr
625                 630                 635                 640

Pro Glu Arg Ala Ala His Cys Ile His Ala Glu Trp Asp Thr Gly Leu
                645                 650                 655

Asn Ser Lys Phe Thr Phe Ser Ile Pro Tyr Val Ser Ala Ala Asp Tyr
            660                 665                 670

Ala Tyr Thr Ala Ser Asp Thr Ala Glu Thr Ile Asn Val Gln Gly Trp
        675                 680                 685

Val Cys Ile Tyr Gln Ile Thr His Gly Lys Ala Glu Asn Asp Thr Leu
    690                 695                 700

Val Val Ser Val Ser Ala Gly Lys Asp Phe Glu Leu Arg Leu Pro Ile
705                 710                 715                 720

Asp Pro Arg Gln Gln Thr Thr Ala Thr Gly Glu Ser Ala Asp Pro Val
                725                 730                 735

Thr Thr Thr Val Glu Asn Tyr Gly Gly Glu Thr Gln Ile Gln Arg Arg
            740                 745                 750

His His Thr Asp Ile Gly Phe Ile Met Asp Arg Phe Val Lys Ile Gln
        755                 760                 765

Ser Leu Ser Pro Thr His Val Ile Asp Leu Met Gln Thr His Gln His
```

-continued

```
    770                 775                 780

Gly Leu Val Gly Ala Leu Leu Arg Ala Ala Thr Tyr Tyr Phe Ser Asp
785                 790                 795                 800

Leu Glu Ile Val Val Arg His Glu Gly Asn Leu Thr Trp Val Pro Asn
                805                 810                 815

Gly Ala Pro Glu Ser Ala Leu Leu Asn Thr Ser Asn Pro Thr Ala Tyr
            820                 825                 830

Asn Lys Ala Pro Phe Thr Arg Leu Ala Leu Pro Tyr Thr Ala Pro His
        835                 840                 845

Arg Val Leu Ala Thr Val Tyr Asn Gly Thr Ser Lys Tyr Ala Val Gly
    850                 855                 860

Gly Ser Gly Arg Arg Gly Asp Met Gly Ser Leu Ala Ala Arg Val Val
865                 870                 875                 880

Lys Gln Leu Pro Ala Ser Phe Asn Tyr Gly Ala Ile Lys Ala Asp Ala
                885                 890                 895

Ile His Glu Leu Leu Val Arg Met Lys Arg Ala Glu Leu Tyr Cys Pro
            900                 905                 910

Arg Pro Leu Leu Ala Ile Glu Val Ser Ser Gln Asp Arg His Lys Gln
        915                 920                 925

Lys Ile Ile Ala Pro Ala Lys Gln Leu Leu Asn Phe Asp Leu Leu Lys
    930                 935                 940

Leu Ala Gly Asp Val Glu Ser Asn Pro Gly Pro Phe Phe Phe Ser Asp
945                 950                 955                 960

Val Arg Ser Asn Phe Ser Lys Leu Val Asp Thr Ile Asn Gln Met Gln
                965                 970                 975

Glu Asp Met Ser Thr Lys His Gly Pro Asp Phe Asn Arg Leu Val Ser
            980                 985                 990

Ala Phe Glu Glu Leu Ala Thr Gly  Val Lys Ala Ile Arg  Thr Gly Leu
        995                 1000                1005

Asp Glu  Ala Lys Pro Trp Tyr  Lys Leu Ile Lys Leu  Leu Ser Arg
    1010                1015                1020

Leu Ser  Cys Met Ala Ala Val  Ala Ala Arg Ser Lys  Asp Pro Val
    1025                1030                1035

Leu Val  Ala Ile Met Leu Ala  Asp Thr Gly Leu Glu  Ile Leu Asp
    1040                1045                1050

Ser Thr  Phe Val Val Lys Lys  Ile Ser Asp Ser Leu  Ser Ser Leu
    1055                1060                1065

Phe His  Val Pro Ala Pro Val  Phe Ser Phe Gly Ala  Pro Ile Leu
    1070                1075                1080

Leu Ala  Gly Leu Val Lys Val  Ala Ser Ser Phe Phe  Arg Ser Thr
    1085                1090                1095

Pro Glu  Asp Leu Glu Arg Ala  Glu Lys Gln Leu Lys  Ala Arg Asp
    1100                1105                1110

Ile Asn  Asp Ile Phe Ala Ile  Leu Lys Asn Gly Glu  Trp Leu Val
    1115                1120                1125

Lys Leu  Ile Leu Ala Ile Arg  Asp Trp Ile Lys Ala  Trp Ile Ala
    1130                1135                1140

Ser Glu  Glu Lys Phe Val Thr  Thr Thr Asp Leu Val  Pro Gly Ile
    1145                1150                1155

Leu Glu  Lys Gln Arg Asp Leu  Asn Asp Pro Ser Lys  Tyr Lys Glu
    1160                1165                1170

Ala Lys  Glu Trp Leu Asp Asn  Ala Arg Gln Ala Cys  Leu Lys Ser
    1175                1180                1185
```

```
Gly Asn Val His Ile Ala Asn Leu Cys Lys Val Val Ala Pro Ala
    1190                1195                1200

Pro Ser Arg Ser Arg Pro Glu Pro Val Val Val Cys Leu Arg Gly
    1205                1210                1215

Lys Ser Gly Gln Gly Lys Ser Phe Leu Ala Asn Val Leu Ala Gln
    1220                1225                1230

Ala Ile Ser Thr His Phe Thr Gly Arg Thr Asp Ser Val Trp Tyr
    1235                1240                1245

Cys Pro Pro Asp Pro Asp His Phe Asp Gly Tyr Asn Gln Gln Thr
    1250                1255                1260

Val Val Val Met Asp Asp Leu Gly Gln Asn Pro Asp Gly Lys Asp
    1265                1270                1275

Phe Lys Tyr Phe Ala Gln Met Val Ser Thr Thr Gly Phe Ile Pro
    1280                1285                1290

Pro Met Ala Ser Leu Glu Asp Lys Gly Lys Pro Phe Asn Ser Lys
    1295                1300                1305

Val Ile Ile Ala Thr Thr Asn Leu Tyr Ser Gly Phe Thr Pro Arg
    1310                1315                1320

Thr Met Val Cys Pro Asp Ala Leu Asn Arg Arg Phe His Phe Asp
    1325                1330                1335

Ile Asp Val Ser Ala Lys Asp Gly Tyr Lys Ile Asn Asn Lys Leu
    1340                1345                1350

Asp Ile Ile Lys Ala Leu Glu Asp Thr His Thr Asn Pro Val Ala
    1355                1360                1365

Met Phe Gln Tyr Asp Cys Ala Leu Leu Asn Gly Met Ala Val Glu
    1370                1375                1380

Met Lys Arg Met Gln Gln Asp Met Phe Lys Pro Gln Pro Pro Leu
    1385                1390                1395

Gln Asn Val Tyr Gln Leu Val Gln Glu Val Ile Glu Arg Val Glu
    1400                1405                1410

Leu His Glu Lys Val Ser Ser His Pro Ile Phe Lys Gln Ile Ser
    1415                1420                1425

Ile Pro Ser Gln Lys Ser Val Leu Tyr Phe Leu Ile Glu Lys Gly
    1430                1435                1440

Gln His Glu Ala Ala Ile Glu Phe Phe Glu Gly Met Val His Asp
    1445                1450                1455

Ser Ile Lys Glu Glu Leu Arg Pro Leu Ile Gln Gln Thr Ser Phe
    1460                1465                1470

Val Lys Arg Ala Phe Lys Arg Leu Lys Glu Asn Phe Glu Ile Val
    1475                1480                1485

Ala Leu Cys Leu Thr Leu Leu Ala Asn Ile Val Ile Met Ile Arg
    1490                1495                1500

Glu Thr Arg Lys Arg Gln Lys Met Val Asp Asp Ala Val Ser Glu
    1505                1510                1515

Tyr Ile Glu Arg Ala Asn Ile Thr Thr Asp Asp Lys Thr Leu Asp
    1520                1525                1530

Glu Ala Glu Lys Asn Pro Leu Glu Thr Ser Gly Ala Ser Thr Val
    1535                1540                1545

Gly Phe Arg Glu Arg Pro Leu Pro Gly Gln Lys Ala Arg Asn Asp
    1550                1555                1560

Glu Asn Ser Glu Pro Ala Gln Pro Ala Glu Glu Gln Pro Gln Ala
    1565                1570                1575
```

```
Glu Gly  Pro Tyr Ala Gly Pro  Leu Glu Arg Gln Lys  Pro Leu Lys
    1580                 1585                 1590

Val Arg  Ala Lys Leu Pro Gln  Gln Glu Gly Pro Tyr  Ala Gly Pro
    1595                 1600                 1605

Met Glu  Arg Gln Lys Pro Leu  Lys Val Lys Ala Lys  Ala Pro Val
    1610                 1615                 1620

Val Lys  Glu Gly Pro Tyr Glu  Gly Pro Val Lys Lys  Pro Val Ala
    1625                 1630                 1635

Leu Lys  Val Lys Ala Lys Asn  Leu Ile Val Thr Glu  Ser Gly Ala
    1640                 1645                 1650

Pro Pro  Thr Asp Leu Gln Lys  Leu Val Met Gly Asn  Thr Lys Pro
    1655                 1660                 1665

Val Glu  Leu Ile Leu Asp Gly  Lys Thr Val Ala Ile  Cys Cys Ala
    1670                 1675                 1680

Thr Gly  Val Phe Gly Thr Ala  Tyr Leu Val Pro Arg  His Leu Phe
    1685                 1690                 1695

Ala Glu  Lys Tyr Asp Lys Ile  Met Leu Asp Gly Arg  Ala Met Thr
    1700                 1705                 1710

Asp Ser  Asp Tyr Arg Val Phe  Glu Phe Glu Ile Lys  Val Lys Gly
    1715                 1720                 1725

Gln Asp  Met Leu Ser Asp Ala  Ala Leu Met Val Leu  His Arg Gly
    1730                 1735                 1740

Asn Arg  Val Arg Asp Ile Thr  Lys His Phe Arg Asp  Thr Ala Arg
    1745                 1750                 1755

Met Lys  Lys Gly Thr Pro Val  Val Gly Val Ile Asn  Asn Ala Asp
    1760                 1765                 1770

Val Gly  Arg Leu Ile Phe Ser  Gly Glu Ala Leu Thr  Tyr Lys Asp
    1775                 1780                 1785

Ile Val  Val Cys Met Asp Gly  Asp Thr Met Pro Gly  Leu Phe Ala
    1790                 1795                 1800

Tyr Lys  Ala Ala Thr Lys Ala  Gly Tyr Cys Gly Gly  Ala Val Leu
    1805                 1810                 1815

Ala Lys  Asp Gly Ala Asp Thr  Phe Ile Val Gly Thr  His Ser Ala
    1820                 1825                 1830

Gly Gly  Asn Gly Val Gly Tyr  Cys Ser Cys Val Ser  Arg Ser Met
    1835                 1840                 1845

Leu Leu  Lys Met Lys Ala His  Val Asp Pro Glu Pro  His His Glu
    1850                 1855                 1860

Gly Leu  Ile Val Asp Thr Arg  Asp Val Glu Glu Arg  Val His Val
    1865                 1870                 1875

Met Arg  Lys Thr Lys Leu Ala  Pro Thr Val Ala His  Gly Val Phe
    1880                 1885                 1890

Asn Pro  Glu Phe Gly Pro Ala  Ala Leu Ser Asn Lys  Asp Pro Arg
    1895                 1900                 1905

Leu Asn  Asp Gly Val Val Leu  Asp Glu Val Ile Phe  Ser Lys His
    1910                 1915                 1920

Lys Gly  Asp Thr Lys Met Ser  Glu Glu Asp Lys Ala  Leu Phe Arg
    1925                 1930                 1935

Arg Cys  Ala Ala Asp Tyr Ala  Ser Arg Leu His Ser  Val Leu Gly
    1940                 1945                 1950

Thr Ala  Asn Ala Pro Leu Ser  Ile Tyr Glu Ala Ile  Lys Gly Val
    1955                 1960                 1965

Asp Gly  Leu Asp Ala Met Glu  Pro Asp Thr Ala Pro  Gly Leu Pro
```

-continued

```
    1970                1975                1980

Trp Ala  Leu Gln Gly Lys Arg  Arg Gly Ala Leu Ile  Asp Phe Glu
    1985                1990                1995

Asn Gly  Thr Val Gly Pro Glu  Val Glu Ala Ala Leu  Lys Leu Met
    2000                2005                2010

Glu Lys  Arg Glu Tyr Lys Phe  Ala Cys Gln Thr Phe  Leu Lys Asp
    2015                2020                2025

Glu Ile  Arg Pro Met Glu Lys  Val Arg Ala Gly Lys  Thr Arg Ile
    2030                2035                2040

Val Asp  Val Leu Pro Val Glu  His Ile Leu Tyr Thr  Arg Met Met
    2045                2050                2055

Ile Gly  Arg Phe Cys Ala Gln  Met His Ser Asn Asn  Gly Pro Gln
    2060                2065                2070

Ile Gly  Ser Ala Val Gly Cys  Asn Pro Asp Val Asp  Trp Gln Arg
    2075                2080                2085

Phe Gly  Thr His Phe Ala Gln  Tyr Arg Asn Val Trp  Asp Val Asp
    2090                2095                2100

Tyr Ser  Ala Phe Asp Ala Asn  His Cys Ser Asp Ala  Met Asn Ile
    2105                2110                2115

Met Phe  Glu Glu Val Phe Arg  Thr Glu Phe Gly Phe  His Pro Asn
    2120                2125                2130

Ala Glu  Trp Ile Leu Lys Thr  Leu Val Asn Thr Glu  His Ala Tyr
    2135                2140                2145

Glu Asn  Lys Arg Ile Thr Val  Glu Gly Gly Met Pro  Ser Gly Cys
    2150                2155                2160

Ser Ala  Thr Ser Ile Ile Asn  Thr Ile Leu Asn Asn  Ile Tyr Val
    2165                2170                2175

Leu Tyr  Ala Leu Arg Arg His  Tyr Glu Gly Val Glu  Leu Asp Thr
    2180                2185                2190

Tyr Thr  Met Ile Ser Tyr Gly  Asp Asp Ile Val Val  Ala Ser Asp
    2195                2200                2205

Tyr Asp  Leu Asp Phe Glu Ala  Leu Lys Pro His Phe  Lys Ser Leu
    2210                2215                2220

Gly Gln  Thr Ile Thr Pro Ala  Asp Lys Ser Asp Lys  Gly Phe Val
    2225                2230                2235

Leu Gly  His Ser Ile Thr Asp  Val Thr Phe Leu Lys  Arg His Phe
    2240                2245                2250

His Met  Asp Tyr Gly Thr Gly  Phe Tyr Lys Pro Val  Met Ala Ser
    2255                2260                2265

Lys Thr  Leu Glu Ala Ile Leu  Ser Phe Ala Arg Arg  Gly Thr Ile
    2270                2275                2280

Gln Glu  Lys Leu Ile Ser Val  Ala Gly Leu Ala Val  His Ser Gly
    2285                2290                2295

Pro Asp  Glu Tyr Arg Arg Leu  Phe Glu Pro Phe Gln  Gly Leu Phe
    2300                2305                2310

Glu Ile  Pro Ser Tyr Arg Ser  Leu Tyr Leu Arg Trp  Val Asn Ala
    2315                2320                2325

Val Cys  Gly Asp Ala
    2330
```

```
<210> SEQ ID NO 2
<211> LENGTH: 1126
<212> TYPE: PRT
<213> ORGANISM: artificial sequence
```

<220> FEATURE:
<223> OTHER INFORMATION: Modified polyprotein of A24 Cruzeiro Strain in
VP2 (H93C) or P1 (H179C)

<400> SEQUENCE: 2

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly Cys Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Val Asn Asn Thr Ser Ala Ala Gln Ile Lys Val Tyr Ala Asn
        275                 280                 285

Ile Ala Pro Thr Tyr Val His Val Ala Gly Glu Leu Pro Ser Lys Glu
    290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Asp Gly Lys Pro Tyr Val
        355                 360                 365

Thr Thr Arg Thr Asp Asp Thr Arg Leu Leu Ala Lys Phe Asp Leu Ser
    370                 375                 380

Leu Ala Ala Lys His Met Ser Asn Thr Tyr Leu Ser Gly Ile Ala Gln
```

-continued

```
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Arg Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
        515                 520                 525

Thr Gly Glu Ser Ala Asp Pro Val Thr Thr Thr Val Glu Asn Tyr Gly
    530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
            580                 585                 590

Ala Ala Thr Tyr Tyr Phe Ser Asp Leu Glu Ile Val Val Arg His Glu
        595                 600                 605

Gly Asn Leu Thr Trp Val Pro Asn Gly Ala Pro Glu Ser Ala Leu Leu
    610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ala Val Gly Gly Ser Gly Arg Arg Gly Asp Met
            660                 665                 670

Gly Ser Leu Ala Ala Arg Val Val Lys Gln Leu Pro Ala Ser Phe Asn
        675                 680                 685

Tyr Gly Ala Ile Lys Ala Asp Ala Ile His Glu Leu Leu Val Arg Met
    690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
            740                 745                 750

Pro Gly Pro Phe Phe Phe Ala Asp Val Arg Ser Asn Phe Ser Lys Leu
        755                 760                 765

Val Asp Thr Ile Asn Gln Met Gln Glu Asp Met Ser Thr Lys His Gly
    770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
                805                 810                 815
```

```
Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
        835                 840                 845

Leu Glu Arg Gln Arg Pro Leu Lys Val Arg Ala Lys Leu Pro Gln Gln
    850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
            980                 985                 990

Asp Met Leu Ser Asp Ala Ala Leu  Met Val Leu His Arg  Gly Asn Arg
        995                 1000                 1005

Val Arg  Asp Ile Thr Lys His  Phe Arg Asp Thr Ala  Arg Met Lys
    1010                 1015                 1020

Lys Gly  Thr Pro Val Val Gly  Val Val Asn Asn Ala  Asp Val Gly
    1025                 1030                 1035

Arg Leu  Ile Phe Ser Gly Glu  Ala Leu Thr Tyr Lys  Asp Ile Val
    1040                 1045                 1050

Val Cys  Met Asp Gly Asp Thr  Met Pro Gly Leu Phe  Ala Tyr Lys
    1055                 1060                 1065

Ala Ala  Thr Lys Ala Gly Tyr  Cys Gly Gly Ala Val  Leu Ala Lys
    1070                 1075                 1080

Asp Gly  Ala Asp Thr Phe Ile  Val Gly Thr His Ser  Ala Gly Gly
    1085                 1090                 1095

Asn Gly  Val Gly Tyr Cys Ser  Cys Val Ser Arg Ser  Met Leu Leu
    1100                 1105                 1110

Arg Met  Lys Ala His Val Asp  Pro Glu Pro Gln His  Glu
    1115                 1120                 1125
```

<210> SEQ ID NO 3
<211> LENGTH: 3378
<212> TYPE: DNA
<213> ORGANISM: artificial sequence
<220> FEATURE:
<223> OTHER INFORMATION: Polynucleotide encoding modified polyprotein of A24

<400> SEQUENCE: 3

```
atgggtgctg gccagtcctc ccctgctacc ggttcccaga accagtccgg caacaccggt     60

tccatcatca acaactacta catgcagcag taccagaact ccatggacac ccagctggga    120

gacaacgcta tctccggtgg ttccaacgag ggttccaccg acaccacctc tacccacacc    180

accaacaccc agaacaacga ctggttctcc aagctggctt cctccgcttt caccggcctg    240
```

-continued

```
ttcggtgctc tgctggctga caagaaaacc gaggaaacca ccctgctcga ggaccgtatc    300
ctgaccaccc gtaacggtca caccacttcc accacccagt cctccgtggg cgtgacccac    360
ggttactcca ccgaagagga ccacgtggcc ggtcctaaca cctccggcct ggaaacccgt    420
gtggtgcagg ctgagcgctt ctacaagaag tacctgttcg actggaccac cgacaaggct    480
ttcggtcacc tggaaaagct ggaactgccc tccgaccacc acggcgtgtt cggatgcctg    540
gtggactcct acgcttacat gcgtaacggc tgggacgtgg aggtgtccgc tgtgggcaac    600
cagttcaacg gtggttgcct gctggtggct atggtgcccg agtggaagga atttgacacc    660
cgcgagaagt accagctgac cctgttcccc caccagttca tctccccccg taccaacatg    720
accgctcaca tcaccgtgcc ctacctgggc gtgaaccgtt acgaccagta caagaagcac    780
aagccctgga ccctggtggt catggtggtg tccccccctga ccgtgaacaa cacctccgct    840
gctcagatca aggtgtacgc taacatcgct cccacctacg tgcacgtcgc cggagagctg    900
ccctccaagg aaggcatctt ccccgtcgct tgcgctgacg gttacggtgg cctggtcacc    960
accgacccca agaccgctga ccccgcttac ggcaaggtgt acaacccccc tcgcaccaac   1020
taccccggtc gtttcaccaa cctgctggac gtggccgagg cttgccccac cttcctgtgc   1080
ttcgacgacg gcaagcccta cgtgaccacc aggaccgacg acacccgtct gctggctaag   1140
ttcgacctgt ccctggctgc taagcacatg tccaacacct acctgtccgg tatcgctcag   1200
tactacaccc agtactccgg caccatcaac ctgcacttca tgttcaccgg ctccaccgac   1260
tccaaggctc gttacatggt ggcttacatc ccccctggtg tcgagactcc ccccgacact   1320
cctgagcgtg ctgctcactg catccacgct gagtgggaca ccggcctgaa ctccaagttc   1380
accttctcca tcccttacgt gtccgctgct gactacgcgt acaccgcttc cgacaccgct   1440
gagactatca acgtgcaggg ctgggtctgc atctaccaga tcacccacgg caaggctgag   1500
aacgacaccc tggtcgtgtc cgtgtccgcc ggcaaggact tcgagctgcg tctgcccatc   1560
gaccctcgtc agcagaccac cgctaccggc gagtctgctg acccagtgac caccaccgtg   1620
gagaactacg gtggcgagac tcagatccag cgtcgtcacc acaccgacat cggtttcatc   1680
atggaccgct tcgtgaagat ccagtccctg tcccctaccc acgtgatcga cctgatgcag   1740
gctcaccagc acggactcgt gggtgctctc ctgcgtgctg ctacctacta cttctccgac   1800
ctggaaatcg tcgtgcgtca cgagggcaac ctgacctggg tgcccaacgg tgctcctgag   1860
tccgctctgc tgaacacctc caaccccacc gcttacaaca aggctccctt cacccgtctg   1920
gctctgcctt acaccgctcc ccaccgtgtg ctggctaccg tgtacaacgg cacctccaag   1980
tacgctgtgg gcggttccgg tcgtcgtggc gacatgggtt ccctggccgc tcgtgtggtc   2040
aagcagctgc ccgcttcctt caactacggt gctatcaagg ctgacgctat ccacgagctg   2100
ttggtgcgta tgaagcgtgc tgagctgtac tgcccccgtc ccctgctggc tatcgaggtg   2160
tcctcccagg accgtcacaa gcagaagatc atcgctcccg ctaagcagct gctgaacttc   2220
gacctgctga agctggctgg cgacgtcgag tccaaccccg gtcccttctt cttcgctgac   2280
gtgcgttcca acttctctaa gctggtggac actatcaacc agatgcaaga ggacatgtcc   2340
accaagcacg gtcccgactt caaccgtctg gtgtccgctt tcgaggaact ggctaccggc   2400
gtgaaggcta tccgtaccgg cctggacgag gctaagccct ggtacaagct gatcaagctg   2460
ctgtcccgtc tgtcctgcat ggctgctgtg gctgctcgtt ccaaggaccc cgtgctggtg   2520
gccatcatgc tggccgacac cggcttggag cgccagcgtc ccctgaaggt ccgcgctaag   2580
```

```
ctgccccagc aggaaggccc ttacgctggt cccctcgagc gtcagaagcc tctgaaggtc   2640

aaggctaagg ctcccgtggt caaggaagga ccctacgagg gacccgtgaa gaagcccgtc   2700

gctctcaagg ttaaggccaa gaacctgatc gtgaccgagt ccggtgctcc tcccaccgac   2760

ctgcaaaaga tggtcatggg caacaccaag cccgtggagc tgatcctgga cggcaagacc   2820

gtggctatct gctgcgctac cggtgttttc ggcaccgctt acctggtgcc ccgtcacctg   2880

ttcgctgaga agtacgacaa gatcatgctg gacggtcgtg ctatgaccga ctccgactac   2940

cgtgtgttcg agttcgagat caaggtcaag ggccaggaca tgctgtccga cgctgctctg   3000

atggtgctgc accgtggcaa ccgtgtgcgt gacatcacca agcacttccg tgacaccgct   3060

cgtatgaaga agggcacccc cgtcgtcggt gtcgtgaaca acgctgacgt gggtcgtctg   3120

atcttctccg gcgaggctct gacctacaag gacatcgtcg tgtgcatgga cggcgacacc   3180

atgcccggac tgttcgctta caaggctgct accaaggctg gttactgcgg tggtgctgtg   3240

ctggccaagg acggtgctga caccttcatc gtgggcaccc actccgctgg tggcaacggt   3300

gtcggttact gctcctgcgt gtcccgttcc atgctgctgc gcatgaaggc tcacgtggac   3360

cccgagcccc agcacgag                                                 3378
```

```
<210> SEQ ID NO 4
<211> LENGTH: 1126
<212> TYPE: PRT
<213> ORGANISM: artificial sequence
<220> FEATURE:
<223> OTHER INFORMATION: Unmodified Polyprotein of A24 Cruzeiro Strain

<400> SEQUENCE: 4

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
    210                 215                 220
```

-continued

```
Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Val Asn Asn Thr Ser Ala Ala Gln Ile Lys Val Tyr Ala Asn
        275                 280                 285

Ile Ala Pro Thr Tyr Val His Val Ala Gly Glu Leu Pro Ser Lys Glu
    290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Asp Gly Lys Pro Tyr Val
        355                 360                 365

Thr Thr Arg Thr Asp Asp Thr Arg Leu Leu Ala Lys Phe Asp Leu Ser
    370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Arg Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510

Asp Phe Glu Leu Arg Leu Pro Ile Asp Pro Arg Gln Gln Thr Thr Ala
        515                 520                 525

Thr Gly Glu Ser Ala Asp Pro Val Thr Thr Thr Val Glu Asn Tyr Gly
    530                 535                 540

Gly Glu Thr Gln Ile Gln Arg Arg His His Thr Asp Ile Gly Phe Ile
545                 550                 555                 560

Met Asp Arg Phe Val Lys Ile Gln Ser Leu Ser Pro Thr His Val Ile
                565                 570                 575

Asp Leu Met Gln Ala His Gln His Gly Leu Val Gly Ala Leu Leu Arg
            580                 585                 590

Ala Ala Thr Tyr Tyr Phe Ser Asp Leu Glu Ile Val Val Arg His Glu
        595                 600                 605

Gly Asn Leu Thr Trp Val Pro Asn Gly Ala Pro Glu Ser Ala Leu Leu
    610                 615                 620

Asn Thr Ser Asn Pro Thr Ala Tyr Asn Lys Ala Pro Phe Thr Arg Leu
625                 630                 635                 640
```

-continued

```
Ala Leu Pro Tyr Thr Ala Pro His Arg Val Leu Ala Thr Val Tyr Asn
            645                 650                 655

Gly Thr Ser Lys Tyr Ala Val Gly Gly Ser Gly Arg Arg Gly Asp Met
        660                 665                 670

Gly Ser Leu Ala Ala Arg Val Val Lys Gln Leu Pro Ala Ser Phe Asn
        675                 680                 685

Tyr Gly Ala Ile Lys Ala Asp Ala Ile His Glu Leu Leu Val Arg Met
    690                 695                 700

Lys Arg Ala Glu Leu Tyr Cys Pro Arg Pro Leu Leu Ala Ile Glu Val
705                 710                 715                 720

Ser Ser Gln Asp Arg His Lys Gln Lys Ile Ile Ala Pro Ala Lys Gln
            725                 730                 735

Leu Leu Asn Phe Asp Leu Leu Lys Leu Ala Gly Asp Val Glu Ser Asn
        740                 745                 750

Pro Gly Pro Phe Phe Phe Ala Asp Val Arg Ser Asn Phe Ser Lys Leu
        755                 760                 765

Val Asp Thr Ile Asn Gln Met Gln Glu Asp Met Ser Thr Lys His Gly
    770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
            805                 810                 815

Leu Ile Lys Leu Leu Ser Arg Leu Ser Cys Met Ala Ala Val Ala Ala
        820                 825                 830

Arg Ser Lys Asp Pro Val Leu Val Ala Ile Met Leu Ala Asp Thr Gly
        835                 840                 845

Leu Glu Arg Gln Arg Pro Leu Lys Val Arg Ala Lys Leu Pro Gln Gln
    850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
            885                 890                 895

Lys Lys Pro Val Ala Leu Lys Val Lys Ala Lys Asn Leu Ile Val Thr
        900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
            965                 970                 975

Asp Ser Asp Tyr Arg Val Phe Glu Phe Glu Ile Lys Val Lys Gly Gln
        980                 985                 990

Asp Met Leu Ser Asp Ala Ala Leu  Met Val Leu His Arg  Gly Asn Arg
        995                 1000                1005

Val Arg  Asp Ile Thr Lys His  Phe Arg Asp Thr Ala  Arg Met Lys
    1010                1015                1020

Lys Gly  Thr Pro Val Val Gly  Val Val Asn Asn Ala  Asp Val Gly
    1025                1030                1035

Arg Leu  Ile Phe Ser Gly Glu  Ala Leu Thr Tyr Lys  Asp Ile Val
    1040                1045                1050

Val Cys  Met Asp Gly Asp Thr  Met Pro Gly Leu Phe  Ala Tyr Lys
```

```
    1055                1060                1065

Ala Ala  Thr Lys Ala Gly Tyr  Cys Gly Gly Ala Val  Leu Ala Lys
    1070                1075                1080

Asp Gly  Ala Asp Thr Phe Ile  Val Gly Thr His Ser  Ala Gly Gly
    1085                1090                1095

Asn Gly  Val Gly Tyr Cys Ser  Cys Val Ser Arg Ser  Met Leu Leu
    1100                1105                1110

Arg Met  Lys Ala His Val Asp  Pro Glu Pro Gln His  Glu
    1115                1120                1125


<210> SEQ ID NO 5
<211> LENGTH: 736
<212> TYPE: PRT
<213> ORGANISM: artificial sequence
<220> FEATURE:
<223> OTHER INFORMATION: Wild-type polyprotein of FMDV O1 manisa strain
      (GenBank AAT01766)

<400> SEQUENCE: 5

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Thr Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
        115                 120                 125

Ser Gly Pro Asn Thr Ser Gly Leu Glu Thr Arg Val Ala Gln Ala Glu
    130                 135                 140

Arg Phe Phe Lys Thr His Leu Phe Asp Trp Val Thr Ser Asp Pro Phe
145                 150                 155                 160

Gly Arg Cys His Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Leu Cys Ser Ile Gln Lys Arg Glu Leu Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Phe Val Gly Val Asn Arg Tyr Asp Gln Tyr
                245                 250                 255

Lys Val His Lys Pro Trp Thr Leu Val Val Met Val Val Ala Pro Leu
            260                 265                 270

Thr Val Asn Ser Glu Gly Ala Pro Gln Ile Lys Val Tyr Ala Asn Ile
        275                 280                 285
```

-continued

```
Ala Pro Thr Asn Val His Val Ala Gly Glu Phe Pro Ser Lys Glu Gly
    290                 295                 300

Ile Phe Pro Val Ala Cys Ser Asp Gly Tyr Gly Gly Leu Val Thr Thr
305                 310                 315                 320

Asp Pro Lys Thr Ala Asp Pro Ala Tyr Gly Lys Val Phe Asn Pro Pro
                325                 330                 335

Arg Asn Met Leu Pro Gly Arg Phe Thr Asn Phe Leu Asp Val Ala Glu
            340                 345                 350

Ala Cys Pro Thr Phe Leu His Phe Glu Gly Asp Val Pro Tyr Val Thr
        355                 360                 365

Thr Lys Thr Asp Ser Asp Arg Val Leu Ala Gln Phe Asp Leu Ser Leu
    370                 375                 380

Ala Ala Lys His Met Ser Asn Thr Phe Leu Ala Gly Leu Ala Gln Tyr
385                 390                 395                 400

Tyr Thr Gln Tyr Ser Gly Thr Ile Asn Leu His Phe Met Phe Thr Gly
                405                 410                 415

Pro Thr Asp Ala Lys Ala Arg Tyr Met Ile Ala Tyr Ala Pro Pro Gly
            420                 425                 430

Met Glu Pro Pro Lys Thr Pro Glu Ala Ala Ala His Cys Ile His Ala
        435                 440                 445

Glu Trp Asp Thr Gly Leu Asn Ser Lys Phe Thr Phe Ser Ile Pro Tyr
    450                 455                 460

Leu Ser Ala Ala Asp Tyr Ala Tyr Thr Ala Ser Asp Thr Ala Glu Thr
465                 470                 475                 480

Thr Asn Val Gln Gly Trp Val Cys Leu Phe Gln Ile Thr His Gly Lys
                485                 490                 495

Ala Asp Gly Asp Ala Leu Val Val Leu Ala Ser Ala Gly Lys Asp Phe
            500                 505                 510

Glu Leu Arg Leu Pro Val Asp Ala Arg Thr Gln Thr Thr Ser Ala Gly
        515                 520                 525

Glu Ser Ala Asp Pro Val Thr Ala Thr Val Glu Asn Tyr Gly Gly Glu
    530                 535                 540

Thr Gln Val Gln Arg Arg Gln His Thr Asp Val Ser Phe Ile Leu Asp
545                 550                 555                 560

Arg Phe Val Lys Val Thr Pro Lys Asp Gln Ile Asn Val Leu Asp Leu
                565                 570                 575

Met Gln Thr Pro Ala His Thr Leu Val Gly Ala Leu Leu Arg Thr Ala
            580                 585                 590

Thr Tyr Tyr Phe Ala Asp Leu Glu Val Ala Val Lys His Glu Gly Asn
        595                 600                 605

Leu Thr Trp Val Pro Asn Gly Ala Pro Glu Ala Ala Leu Asp Asn Thr
    610                 615                 620

Thr Asn Pro Thr Ala Tyr His Lys Ala Pro Leu Thr Arg Leu Ala Leu
625                 630                 635                 640

Pro Tyr Thr Ala Pro His Arg Val Leu Ala Thr Val Tyr Asn Gly Asn
                645                 650                 655

Ser Lys Tyr Gly Asp Gly Thr Val Ala Asn Val Arg Gly Asp Leu Gln
            660                 665                 670

Val Leu Ala Gln Lys Ala Ala Arg Ala Leu Pro Thr Ser Phe Asn Tyr
        675                 680                 685

Gly Ala Ile Lys Ala Thr Arg Val Thr Glu Leu Leu Tyr Arg Met Lys
    690                 695                 700

Arg Ala Glu Thr Tyr Cys Pro Arg Pro Leu Leu Ala Ile His Pro Asp
```

```
705                 710                 715                 720

Gln Ala Arg His Lys Gln Lys Ile Val Ala Pro Val Lys Gln Leu Leu
                725                 730                 735


<210> SEQ ID NO 6
<211> LENGTH: 737
<212> TYPE: PRT
<213> ORGANISM: artificial sequence
<220> FEATURE:
<223> OTHER INFORMATION: Modified polyprotein of FMDV O1 manisa strain
      in VP2 (S93C) or P1 (S179C)

<400> SEQUENCE: 6

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Thr Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Thr Ala Glu Asp Phe
        115                 120                 125

Val Ser Gly Pro Asn Thr Ser Gly Leu Glu Thr Arg Val Ala Gln Ala
    130                 135                 140

Glu Arg Phe Phe Lys Thr His Leu Phe Asp Trp Val Thr Ser Asp Pro
145                 150                 155                 160

Phe Gly Arg Cys His Leu Leu Glu Leu Pro Thr Asp His Lys Gly Val
                165                 170                 175

Tyr Gly Cys Leu Thr Asp Ser Tyr Ala Tyr Met Arg Asn Gly Trp Asp
            180                 185                 190

Val Glu Val Thr Ala Val Gly Asn Gln Phe Asn Gly Gly Cys Leu Leu
        195                 200                 205

Val Ala Met Val Pro Glu Leu Cys Ser Ile Gln Lys Arg Glu Leu Tyr
    210                 215                 220

Gln Leu Thr Leu Phe Pro His Gln Phe Ile Asn Pro Arg Thr Asn Met
225                 230                 235                 240

Thr Ala His Ile Thr Val Pro Phe Val Gly Val Asn Arg Tyr Asp Gln
                245                 250                 255

Tyr Lys Val His Lys Pro Trp Thr Leu Val Val Met Val Val Ala Pro
            260                 265                 270

Leu Thr Val Asn Ser Glu Gly Ala Pro Gln Ile Lys Val Tyr Ala Asn
        275                 280                 285

Ile Ala Pro Thr Asn Val His Val Ala Gly Glu Phe Pro Ser Lys Glu
    290                 295                 300

Gly Ile Phe Pro Val Ala Cys Ser Asp Gly Tyr Gly Gly Leu Val Thr
305                 310                 315                 320

Thr Asp Pro Lys Thr Ala Asp Pro Ala Tyr Gly Lys Val Phe Asn Pro
                325                 330                 335
```

```
Pro Arg Asn Met Leu Pro Gly Arg Phe Thr Asn Phe Leu Asp Val Ala
            340                 345                 350

Glu Ala Cys Pro Thr Phe Leu His Phe Glu Gly Asp Val Pro Tyr Val
        355                 360                 365

Thr Thr Lys Thr Asp Ser Asp Arg Val Leu Ala Gln Phe Asp Leu Ser
    370                 375                 380

Leu Ala Ala Lys His Met Ser Asn Thr Phe Leu Ala Gly Leu Ala Gln
385                 390                 395                 400

Tyr Tyr Thr Gln Tyr Ser Gly Thr Ile Asn Leu His Phe Met Phe Thr
                405                 410                 415

Gly Pro Thr Asp Ala Lys Ala Arg Tyr Met Ile Ala Tyr Ala Pro Pro
            420                 425                 430

Gly Met Glu Pro Pro Lys Thr Pro Glu Ala Ala Ala His Cys Ile His
        435                 440                 445

Ala Glu Trp Asp Thr Gly Leu Asn Ser Lys Phe Thr Phe Ser Ile Pro
    450                 455                 460

Tyr Leu Ser Ala Ala Asp Tyr Ala Tyr Thr Ala Ser Asp Thr Ala Glu
465                 470                 475                 480

Thr Thr Asn Val Gln Gly Trp Val Cys Leu Phe Gln Ile Thr His Gly
                485                 490                 495

Lys Ala Asp Gly Asp Ala Leu Val Val Leu Ala Ser Ala Gly Lys Asp
            500                 505                 510

Phe Glu Leu Arg Leu Pro Val Asp Ala Arg Thr Gln Thr Thr Ser Ala
        515                 520                 525

Gly Glu Ser Ala Asp Pro Val Thr Ala Thr Val Glu Asn Tyr Gly Gly
    530                 535                 540

Glu Thr Gln Val Gln Arg Arg Gln His Thr Asp Val Ser Phe Ile Leu
545                 550                 555                 560

Asp Arg Phe Val Lys Val Thr Pro Lys Asp Gln Ile Asn Val Leu Asp
                565                 570                 575

Leu Met Gln Thr Pro Ala His Thr Leu Val Gly Ala Leu Leu Arg Thr
            580                 585                 590

Ala Thr Tyr Tyr Phe Ala Asp Leu Glu Val Ala Val Lys His Glu Gly
        595                 600                 605

Asn Leu Thr Trp Val Pro Asn Gly Ala Pro Glu Ala Ala Leu Asp Asn
    610                 615                 620

Thr Thr Asn Pro Thr Ala Tyr His Lys Ala Pro Leu Thr Arg Leu Ala
625                 630                 635                 640

Leu Pro Tyr Thr Ala Pro His Arg Val Leu Ala Thr Val Tyr Asn Gly
                645                 650                 655

Asn Ser Lys Tyr Gly Asp Gly Thr Val Ala Asn Val Arg Gly Asp Leu
            660                 665                 670

Gln Val Leu Ala Gln Lys Ala Ala Arg Ala Leu Pro Thr Ser Phe Asn
        675                 680                 685

Tyr Gly Ala Ile Lys Ala Thr Arg Val Thr Glu Leu Leu Tyr Arg Met
    690                 695                 700

Lys Arg Ala Glu Thr Tyr Cys Pro Arg Pro Leu Leu Ala Ile His Pro
705                 710                 715                 720

Asp Gln Ala Arg His Lys Gln Lys Ile Val Ala Pro Val Lys Gln Leu
                725                 730                 735

Leu

<210> SEQ ID NO 7
```

```
<211> LENGTH: 2211
<212> TYPE: DNA
<213> ORGANISM: artificial sequence
<220> FEATURE:
<223> OTHER INFORMATION: Polynucleotide encoding modified polyprotein of
      FMDV O1 manisa strain

<400> SEQUENCE: 7

atgggtgctg gccagtcctc ccccgctacc ggttcccaga accagtccgg caacaccggt     60

tccatcatca acaactacta catgcagcag taccagaact ccatggacac ccagctgggc    120

gacaacgcta cctccggtgg ttccaacgag ggttccaccg acaccacctc tacccacacc    180

accaacaccc agaacaacga ctggttctcc aagctggctt cctccgcttt ctccggcctg    240

ttcggtgctc tgctggctga caagaagacc gaggaaacca ccctgctcga ggaccgtatc    300

ctgaccaccc gtaacggtca caccacctcc accacccagt cctccgtggg tgtcacctac    360

ggttacgcta ccgctgagga cttcgtgtcc ggtcccaaca cctccggcct ggaaacccgt    420

gtggctcagg ctgagcgctt cttcaagacc cacctgttcg actgggtcac ctccgacccc    480

ttcggtcgtt gccacctgtt ggagctgccc accgaccaca agggcgtgta cggttgcctg    540

accgactcct acgcttacat gcgtaacggc tgggacgtgg aagtgaccgc tgtgggcaac    600

cagttcaacg gtggttgcct gctggtggct atggtgcccg agctgtgctc catccagaag    660

cgcgagctgt accagctgac cctgttcccc caccagttca tcaacccccg taccaacatg    720

accgctcaca tcaccgtgcc cttcgtgggc gtgaaccgtt acgaccagta caaggtgcac    780

aagccctgga ccctggtcgt gatggtggtg gctcccctga ccgtgaactc cgagggtgct    840

ccccagatca aggtgtacgc taacatcgct cccaccaacg tgcacgtggc cggcgagttc    900

ccatccaagg aaggcatctt ccccgtcgct tgctccgacg gttacggtgg cctggtcacc    960

actgacccca agaccgctga ccccgcttac ggcaaggtgt tcaacccccc tcgtaacatg   1020

ctgcccggtc gtttcaccaa cttcttggac gtggccgagg cttgccccac cttcctgcac   1080

ttcgagggcg acgtgcccta cgtgaccacc aagactgact ccgaccgtgt gctggctcag   1140

ttcgacctgt ccctggctgc taagcacatg tccaacactt tcttggctgg cctggctcag   1200

tactacaccc agtactccgg caccatcaac ctgcacttca tgttcaccgg tcccaccgac   1260

gctaaggctc gttacatgat cgcttacgct ccccctggca tggaaccccc caagacccca   1320

gaggctgctg ctcactgcat ccacgctgag tgggacaccg gcctgaactc caagttcacc   1380

ttctccatcc cttacctgtc cgctgctgac tacgcctaca ccgcttccga caccgctgag   1440

actaccaacg tccagggctg ggtctgcctg ttccagatca cccacggcaa ggctgacggc   1500

gacgctctgg tggtgctggc ttccgctggc aaggacttcg agctgcgtct gcccgtggac   1560

gctcgtaccc agaccacctc cgctggcgag tctgctgacc ccgtgaccgc taccgtcgag   1620

aactacggtg gcgagactca ggtgcagcgt cgtcagcaca ccgacgtgtc cttcatcctg   1680

gaccgtttcg tgaaggtcac ccccaaggac cagatcaacg tgctggacct gatgcagacc   1740

cccgctcaca ccctcgtggg cgctctgctg cgtaccgcta cctactactt cgctgacctg   1800

gaagtggctg tgaagcacga gggcaacctg acctgggtgc ccaacggtgc tcccgaggct   1860

gctctggaca acaccactaa ccccaccgct taccacaagg ctcctctgac ccgtctggct   1920

ctgccttaca ctgctcccca ccgcgtgctg gctaccgtgt acaacggcaa ctctaagtac   1980

ggcgacggca ccgtggctaa cgtgcgtggc gatctgcagg tcctggctca gaaggctgct   2040

cgcgctctgc ccacctcctt caactacggt gctatcaagg ctacccgtgt gaccgagctg   2100
```

```
ctgtaccgta tgaagcgtgc tgagacttac tgcccccgtc ccctgctggc tatccaccct   2160

gaccaggctc gtcacaagca aaagatcgtg gctcccgtga agcagctgct g            2211


<210> SEQ ID NO 8
<211> LENGTH: 1126
<212> TYPE: PRT
<213> ORGANISM: artificial sequence
<220> FEATURE:
<223> OTHER INFORMATION: modified polyprotein of FMDV Iraq strain

<400> SEQUENCE: 8

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ser Thr Gln Glu Asp His
        115                 120                 125

Val Ser Gly Pro Asn Thr Ser Gly Leu Glu Thr Arg Val Val Gln Ala
    130                 135                 140

Glu Arg Phe Phe Lys Lys His Leu Phe Asp Trp Thr Pro Asp Lys Ala
145                 150                 155                 160

Phe Gly His Leu Glu Lys Leu Glu Leu Pro Thr Asp His Lys Gly Val
                165                 170                 175

Tyr Gly Cys Leu Val Asp Ser Phe Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Thr Pro Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Val Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Thr Asn Thr Val Ser Ala Gly Gln Ile Lys Val Tyr Ala Asn
        275                 280                 285

Ile Ala Pro Thr His Val His Val Ala Gly Glu Leu Pro Ser Lys Glu
    290                 295                 300

Gly Ile Val Pro Val Ala Cys Ser Asp Gly Tyr Gly Gly Leu Val Thr
305                 310                 315                 320

Thr Asp Pro Lys Thr Ala Asp Pro Val Tyr Gly Met Val Tyr Asn Pro
                325                 330                 335

Pro Arg Thr Asn Tyr Pro Gly Arg Phe Thr Asn Leu Leu Asp Val Ala
            340                 345                 350
```

```
Glu Ala Cys Pro Thr Phe Leu Cys Phe Asp Glu Gly Lys Pro Tyr Val
        355                 360                 365

Val Thr Arg Thr Asp Glu Gln Arg Leu Leu Ala Lys Phe Asp Val Ser
    370                 375                 380

Leu Ala Ala Lys His Met Ser Asn Thr Tyr Leu Ser Gly Ile Ala Gln
385                 390                 395                 400

Tyr Tyr Ala Gln Tyr Ser Gly Thr Ile Asn Leu His Phe Met Phe Thr
                405                 410                 415

Gly Ser Thr Asp Ser Lys Ala Arg Tyr Met Val Ala Tyr Val Pro Pro
            420                 425                 430

Gly Val Glu Thr Pro Pro Asp Thr Pro Glu Lys Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Val Ala
465                 470                 475                 480

Glu Thr Thr Asn Val Gln Gly Trp Val Cys Ile Tyr Gln Ile Thr His
                485                 490                 495

Gly Lys Ala Glu Gln Asp Thr Leu Val Val Ser Val Ser Ala Gly Lys
            500                 505                 510

Asp Phe Glu Leu Arg Leu Pro Ile Asp Pro Arg Ser Gln Thr Thr Thr
        515                 520                 525

Thr Gly Glu Ser Ala Asp Pro Val Thr Thr Thr Val Glu Asn Tyr Gly
    530                 535                 540

Gly Glu Thr Gln Val Gln Arg Arg Gln His Thr Asp Val Thr Phe Ile
545                 550                 555                 560

Met Asp Arg Phe Val Lys Ile Gln Asn Leu Asn Pro Thr His Val Ile
                565                 570                 575

Asp Leu Met Gln Thr His Gln His Gly Leu Val Gly Ala Leu Leu Arg
            580                 585                 590

Ala Ala Thr Tyr Tyr Phe Ser Asp Leu Glu Ile Val Val Arg His Asp
        595                 600                 605

Gly Asn Leu Thr Trp Val Pro Asn Gly Ala Pro Glu Ala Ala Leu Ser
    610                 615                 620

Asn Thr Gly Asn Pro Thr Ala Tyr Leu Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ser Ala Gly Gly Thr Gly Arg Arg Gly Asp Leu
            660                 665                 670

Gly Pro Leu Ala Ala Arg Val Ala Ala Gln Leu Pro Ala Ser Phe Asn
        675                 680                 685

Phe Gly Ala Ile Gln Ala Thr Thr Ile His Glu Leu Leu Val Arg Met
    690                 695                 700

Lys Arg Ala Glu Leu Tyr Cys Pro Arg Pro Leu Leu Ala Val Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
            740                 745                 750

Pro Gly Pro Phe Phe Phe Ala Asp Val Arg Ser Asn Phe Ser Lys Leu
        755                 760                 765
```

-continued

```
Val Asp Thr Ile Asn Gln Met Gln Glu Asp Met Ser Thr Lys His Gly
    770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
        835                 840                 845

Leu Glu Arg Gln Arg Pro Leu Lys Val Arg Ala Lys Leu Pro Gln Gln
    850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
            980                 985                 990

Asp Met Leu Ser Asp Ala Ala Leu  Met Val Leu His Arg  Gly Asn Arg
        995                 1000                1005

Val Arg  Asp Ile Thr Lys His  Phe Arg Asp Thr Ala  Arg Met Lys
    1010                1015                1020

Lys Gly  Thr Pro Val Val Gly  Val Val Asn Asn Ala  Asp Val Gly
    1025                1030                1035

Arg Leu  Ile Phe Ser Gly Glu  Ala Leu Thr Tyr Lys  Asp Ile Val
    1040                1045                1050

Val Cys  Met Asp Gly Asp Thr  Met Pro Gly Leu Phe  Ala Tyr Lys
    1055                1060                1065

Ala Ala  Thr Lys Ala Gly Tyr  Cys Gly Gly Ala Val  Leu Ala Lys
    1070                1075                1080

Asp Gly  Ala Asp Thr Phe Ile  Val Gly Thr His Ser  Ala Gly Gly
    1085                1090                1095

Asn Gly  Val Gly Tyr Cys Ser  Cys Val Ser Arg Ser  Met Leu Leu
    1100                1105                1110

Arg Met  Lys Ala His Val Asp  Pro Glu Pro Gln His  Glu
    1115                1120                1125


<210> SEQ ID NO 9
<211> LENGTH: 3378
<212> TYPE: DNA
<213> ORGANISM: artificial sequence
<220> FEATURE:
<223> OTHER INFORMATION: Polynucleotide encoding modified polyprotein of
      FMDV Iraq strain

<400> SEQUENCE: 9
```

atgggtgctg gccagtcctc ccccgctacc ggttcccaga accagtccgg caacaccggt 60
tccatcatca acaactacta catgcagcag taccagaact ccatggacac ccaactcggc 120
gacaacgcta tctccggtgg ttccaacgag ggttccaccg acaccacctc tacccacacc 180
accaacaccc agaacaacga ctggttctcc aagctggctt cctccgcttt ctccggcctg 240
ttcggtgctc tgctggctga caagaagacc gaggaaacca ccctgctcga ggaccgtatc 300
ctgaccaccc gtaacggtca caccacctcc accacccagt cctccgtggg tgttacctac 360
ggttactcca cccaagagga ccacgtgtcc ggtcccaaca cctccggcct ggaaacccgt 420
gtggtgcagg ctgagcgctt cttcaagaag cacctgttcg actggacccc cgacaaggct 480
ttcggtcacc tcgagaagct cgagctgccc accgaccaca agggcgtgta cggttgcctg 540
gtggacagct tcgcttacat gcgtaacggc tgggacgtcg aggtgtccgc tgtgggcaac 600
cagttcaacg gtggttgcct gctggtggct atggtgcccg agtggaaaga attcacccct 660
cgcgagaagt accagctgac cctgttcccc caccagttca tctccccccg taccaacatg 720
accgctcaca tcgtggtgcc ctacctgggt gtcaaccgtt acgaccagta caagaagcac 780
aagccctgga ccctggtggt tatggtggtg tctcccctga ccactaacac cgtgtccgct 840
ggccagatca aggtgtacgc taacatcgct cccacccacg tgcacgtcgc gggcgagctg 900
ccttccaaag aaggcatcgt ccccgtcgct tgctccgacg gttacggtgg cctggtcacc 960
accgacccca agaccgctga ccccgtgtac ggcatggtgt acaacccccc tcgcaccaac 1020
taccccggtc gtttcaccaa cctgctggac gtggccgagg cttgccccac cttcctgtgc 1080
ttcgacgagg gcaagcccta cgtggtcacc cgtaccgacg agcagcgtct gctggctaag 1140
ttcgacgtgt ccctggctgc taagcacatg tccaacacct acctgtccgg tatcgctcag 1200
tactacgccc agtactccgg caccatcaac ctgcacttca tgttcaccgg ctccaccgat 1260
tccaaggctc gttacatggt ggcttacgtg ccccctggtg tcgagactcc ccccgacacc 1320
cctgagaagg ctgctcactg catccacgct gagtgggaca ccggcctgaa ctccaagttc 1380
accttctcca tcccttacgt gtccgccgct gactacgctt acaccgcttc cgacgtcgcc 1440
gagactacca acgtgcaggg ctgggtctgc atctaccaga tcacccacgg caaggctgag 1500
caggacaccc tggtcgtgtc cgtgtctgct ggcaaggact tcgaactccg tctgcccatc 1560
gacccccgtt cccagaccac caccaccggc gagtctgccg accctgtgac caccaccgtg 1620
gaaaactacg gtggcgagac tcaggtgcag cgtcgtcagc acaccgacgt gaccttcatc 1680
atggaccgtt tcgtgaagat ccagaacctg aaccctaccc acgtgatcga cctgatgcag 1740
actcaccagc acggcctcgt gggcgctctg ctgcgtgctg ctacctacta cttctccgac 1800
ctcgagatcg tcgtccgtca cgacggcaac ctgacctggg tgcccaacgg tgctcccgag 1860
gctgctctgt ctaacaccgg caaccccacc gcttacctga aggctccctt cacccgtctg 1920
gctctgccct acaccgctcc ccaccgtgtg ctggctaccg tgtacaacgg cacctccaag 1980
tactccgctg gtggcaccgg tcgtcgtggc gacttgggtc ctctggctgc tcgtgtggct 2040
gctcagctgc ccgcttcctt caacttcggt gctatccagg ctaccaccat ccacgaactc 2100
ctcgtgcgta tgaagcgtgc tgagctgtac tgcccccgtc ccctgctggc tgtggaagtg 2160
tcctcccagg accgtcacaa gcagaagatc atcgctcccg ctaagcagct gctgaacttc 2220
gacctgctga agctggctgg cgacgtggaa tccaaccccg gtcccttctt cttcgctgac 2280
gtgcgttcca acttctctaa gctggtggac actatcaacc agatgcaaga ggacatgtcc 2340

```
accaagcacg gtcccgactt caaccgtctg gtgtccgctt tcgaggaact ggctaccggt   2400

gtcaaggcta tccgtaccgg cctggacgag gctaagccct ggtacaagct gatcaagctg   2460

ctgtcccgtc tgtcctgcat ggctgctgtc gctgctcgtt ccaaggaccc cgtgctggtc   2520

gctatcatgc tggccgacac cggcttggag cgtcagcgtc ctctgaaagt ccgcgctaag   2580

ctgccccagc aagagggccc gtacgctggt cccctcgagc gtcagaagcc cctgaaggtt   2640

aaagccaagg ctcccgtggt caaagaaggc ccatacgagg gtcccgtgaa gaagcccgtc   2700

gctctcaagg tcaaggccaa gaacctgatc gtgaccgagt ccggtgctcc ccccaccgac   2760

ctgcaaaaga tggtcatggg caacaccaag cccgtcgagc tgatcctgga cggcaagacc   2820

gtggctatct gctgcgctac cggcgtgttc ggtactgctt acctggtgcc ccgtcacctg   2880

ttcgctgaga agtacgacaa gatcatgctg gacggtcgtg ctatgaccga ctccgactac   2940

cgtgtgttcg agttcgagat caaagtcaag ggccaggaca tgctgtccga cgctgctctg   3000

atggtgctgc accgtggcaa ccgtgtgcgt gacatcacca agcacttccg tgacaccgct   3060

cgtatgaaga agggcacccc cgtcgtcggt gtcgtgaaca acgctgacgt gggtcgtctg   3120

atcttctccg gcgaggctct gacctacaag gacatcgtcg tgtgcatgga tggcgacacc   3180

atgcctggcc tgttcgctta caaggctgct accaaggctg gttactgcgg tggtgctgtc   3240

ctggctaagg acggtgctga caccttcatc gtgggcaccc actccgctgg cggaaacggt   3300

gtcggttact gctcctgcgt gtcccgttcc atgctgctgc gcatgaaggc tcacgtggac   3360

cccgagcccc agcacgag                                                 3378
```

<210> SEQ ID NO 10
<211> LENGTH: 1122
<212> TYPE: PRT
<213> ORGANISM: artificial sequence
<220> FEATURE:
<223> OTHER INFORMATION: modified polyprotein of FMDV Asia strain

<400> SEQUENCE: 10

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Asn Asn Thr Gln
    50                  55                  60

Asn Asn Asp Trp Phe Ser Arg Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Val Ala Glu Asp Ala
        115                 120                 125

Val Ser Gly Pro Asn Thr Ser Gly Leu Glu Thr Arg Val Gln Gln Ala
    130                 135                 140

Glu Arg Phe Phe Lys Lys His Leu Phe Asp Trp Thr Pro Asn Leu Ala
145                 150                 155                 160

Phe Gly His Cys Tyr Tyr Leu Glu Leu Pro Thr Glu His Lys Gly Val
                165                 170                 175
```

-continued

```
Tyr Gly Cys Leu Met Gly Ser Tyr Ala Tyr Met Arg Asn Gly Trp Asp
            180                 185                 190

Ile Glu Val Thr Ala Val Gly Asn Gln Phe Asn Gly Gly Cys Leu Leu
        195                 200                 205

Val Ala Leu Val Pro Glu Leu Lys Glu Leu Asp Thr Arg Gln Lys Tyr
    210                 215                 220

Gln Leu Thr Leu Phe Pro His Gln Phe Ile Asn Pro Arg Thr Asn Met
225                 230                 235                 240

Thr Ala His Ile Asn Val Pro Tyr Val Gly Ile Asn Arg Tyr Asp Gln
                245                 250                 255

Tyr Ala Leu His Lys Pro Trp Thr Leu Val Val Met Val Val Ala Pro
            260                 265                 270

Leu Thr Val Lys Thr Gly Gly Ser Glu Gln Ile Lys Val Tyr Met Asn
        275                 280                 285

Ala Ala Pro Thr Tyr Val His Val Ala Gly Glu Leu Pro Ser Lys Glu
    290                 295                 300

Gly Ile Val Pro Val Ala Cys Ala Asp Gly Tyr Gly Asn Met Val Thr
305                 310                 315                 320

Thr Asp Pro Lys Thr Ala Asp Pro Val Tyr Gly Lys Val Phe Asn Pro
                325                 330                 335

Pro Arg Thr Asn Leu Pro Gly Arg Phe Thr Asn Phe Leu Asp Val Ala
            340                 345                 350

Glu Ala Cys Pro Thr Phe Leu Arg Phe Gly Glu Val Pro Phe Val Lys
        355                 360                 365

Thr Val Asn Ser Gly Asp Arg Leu Leu Ala Lys Phe Asp Val Ser Leu
    370                 375                 380

Ala Ala Gly His Met Ser Asn Thr Tyr Leu Ala Gly Leu Ala Gln Tyr
385                 390                 395                 400

Tyr Thr Gln Tyr Ser Gly Thr Met Asn Val His Phe Met Phe Thr Gly
                405                 410                 415

Pro Thr Asp Ala Lys Ala Arg Tyr Met Val Ala Tyr Val Pro Pro Gly
            420                 425                 430

Met Thr Pro Pro Thr Asp Pro Glu His Ala Ala His Cys Ile His Ser
        435                 440                 445

Glu Trp Asp Thr Gly Leu Asn Ser Lys Phe Thr Phe Ser Ile Pro Tyr
    450                 455                 460

Leu Ser Ala Ala Asp Tyr Ala Tyr Thr Ala Ser Asp Val Ala Glu Thr
465                 470                 475                 480

Thr Ser Val Gln Gly Trp Val Cys Ile Tyr Gln Ile Thr His Gly Lys
                485                 490                 495

Ala Glu Gly Asp Ala Leu Val Val Ser Val Ser Ala Gly Lys Asp Phe
            500                 505                 510

Glu Phe Arg Leu Pro Val Asp Ala Arg Gln Gln Thr Thr Thr Thr Gly
        515                 520                 525

Glu Ser Ala Asp Pro Val Thr Thr Thr Val Glu Asn Tyr Gly Gly Glu
    530                 535                 540

Thr Gln Thr Ala Arg Arg Leu His Thr Asp Val Ala Phe Ile Leu Asp
545                 550                 555                 560

Arg Phe Val Lys Leu Thr Ala Pro Lys Asn Ile Gln Thr Leu Asp Leu
                565                 570                 575

Met Gln Ile Pro Ser His Thr Leu Val Gly Ala Leu Leu Arg Ser Ala
            580                 585                 590

Thr Tyr Tyr Phe Ser Asp Leu Glu Val Ala Leu Val His Thr Gly Pro
```

```
        595                 600                 605

Val Thr Trp Val Pro Asn Gly Ala Pro Lys Asp Ala Leu Asn Asn Gln
    610                 615                 620

Thr Asn Pro Thr Ala Tyr Gln Lys Gln Pro Ile Thr Arg Leu Ala Leu
625                 630                 635                 640

Pro Tyr Thr Ala Pro His Arg Val Leu Ala Thr Val Tyr Asn Gly Lys
                645                 650                 655

Thr Ala Tyr Gly Glu Thr Thr Ser Arg Arg Gly Asp Met Ala Ala Leu
            660                 665                 670

Ala Gln Arg Leu Ser Ala Arg Leu Pro Thr Ser Phe Asn Tyr Gly Ala
        675                 680                 685

Val Lys Ala Asp Thr Ile Thr Glu Leu Leu Ile Arg Met Lys Arg Ala
    690                 695                 700

Glu Thr Tyr Cys Pro Arg Pro Leu Leu Ala Leu Asp Thr Thr Gln Asp
705                 710                 715                 720

Arg Arg Lys Gln Glu Ile Ile Ala Pro Glu Lys Gln Val Leu Asn Phe
                725                 730                 735

Asp Leu Leu Lys Leu Ala Gly Asp Val Glu Ser Asn Pro Gly Pro Phe
            740                 745                 750

Phe Phe Ala Asp Val Arg Ser Asn Phe Ser Lys Leu Val Asp Thr Ile
        755                 760                 765

Asn Gln Met Gln Glu Asp Met Ser Thr Lys His Gly Pro Asp Phe Asn
    770                 775                 780

Arg Leu Val Ser Ala Phe Glu Glu Leu Ala Thr Gly Val Lys Ala Ile
785                 790                 795                 800

Arg Thr Gly Leu Asp Glu Ala Lys Pro Trp Tyr Lys Leu Ile Lys Leu
                805                 810                 815

Leu Ser Arg Leu Ser Cys Met Ala Ala Val Ala Ala Arg Ser Lys Asp
            820                 825                 830

Pro Val Leu Val Ala Ile Met Leu Ala Asp Thr Gly Leu Glu Arg Gln
        835                 840                 845

Arg Pro Leu Lys Val Arg Ala Lys Leu Pro Gln Gln Glu Gly Pro Tyr
    850                 855                 860

Ala Gly Pro Leu Glu Arg Gln Lys Pro Leu Lys Val Lys Ala Lys Ala
865                 870                 875                 880

Pro Val Val Lys Glu Gly Pro Tyr Glu Gly Pro Val Lys Lys Pro Val
                885                 890                 895

Ala Leu Lys Val Lys Ala Lys Asn Leu Ile Val Thr Glu Ser Gly Ala
            900                 905                 910

Pro Pro Thr Asp Leu Gln Lys Met Val Met Gly Asn Thr Lys Pro Val
        915                 920                 925

Glu Leu Ile Leu Asp Gly Lys Thr Val Ala Ile Cys Cys Ala Thr Gly
    930                 935                 940

Val Phe Gly Thr Ala Tyr Leu Val Pro Arg His Leu Phe Ala Glu Lys
945                 950                 955                 960

Tyr Asp Lys Ile Met Leu Asp Gly Arg Ala Met Thr Asp Ser Asp Tyr
                965                 970                 975

Arg Val Phe Glu Phe Glu Ile Lys Val Lys Gly Gln Asp Met Leu Ser
            980                 985                 990

Asp Ala Ala Leu Met Val Leu His  Arg Gly Asn Arg Val  Arg Asp Ile
        995                 1000                1005

Thr Lys  His Phe Arg Asp Thr  Ala Arg Met Lys Lys  Gly Thr Pro
    1010                1015                1020
```

```
Val Val  Gly Val Val Asn Asn  Ala Asp Val Gly Arg  Leu Ile Phe
    1025                 1030                 1035

Ser Gly  Glu Ala Leu Thr Tyr  Lys Asp Ile Val Val  Cys Met Asp
    1040                 1045                 1050

Gly Asp  Thr Met Pro Gly Leu  Phe Ala Tyr Lys Ala  Ala Thr Lys
    1055                 1060                 1065

Ala Gly  Tyr Cys Gly Gly Ala  Val Leu Ala Lys Asp  Gly Ala Asp
    1070                 1075                 1080

Thr Phe  Ile Val Gly Thr His  Ser Ala Gly Gly Asn  Gly Val Gly
    1085                 1090                 1095

Tyr Cys  Ser Cys Val Ser Arg  Ser Met Leu Leu Arg  Met Lys Ala
    1100                 1105                 1110

His Val  Asp Pro Glu Pro Gln  His Glu
    1115                 1120
```

<210> SEQ ID NO 11
<211> LENGTH: 3366
<212> TYPE: DNA
<213> ORGANISM: artificial sequence
<220> FEATURE:
<223> OTHER INFORMATION: Polynucleotide encoding modified protein of FMDV Asia strain

<400> SEQUENCE: 11

```
atgggtgctg gccagtcctc ccctgctacc ggttcccaga accagtccgg caacaccggt      60

tccatcatca acaactacta catgcagcag taccagaact ccatggacac ccagctcggc     120

gacaacgcta tctccggtgg ttccaacgag ggttccaccg acaccacctc cacccacacc     180

aacaacaccc agaacaacga ctggttctcc cgtctggctt cctccgcttt ctccggcctg     240

ttcggtgctc tgctggctga caagaagacc gaggaaacca ccctgctcga ggaccgtatc     300

ctgaccaccc gtaacggtca caccacctct accacccagt cctctgtggg tgtcacctac     360

ggttacgctg tggctgagga cgctgtgtcc ggtcccaaca cctccggcct ggaaacccgt     420

gtgcagcagg ctgagcgctt cttcaagaag cacctgttcg actggacccc caacctggct     480

ttcggtcact gctactacct cgagctgccc accgagcaca agggcgtgta cggttgcctg     540

atgggctcct acgcttacat gcgtaacggc tgggacatcg aagtgaccgc tgtgggcaac     600

cagttcaacg gtggttgcct gctggtggct ctggtgcccg agctgaaaga actggacacc     660

cgtcagaagt accagctgac cctgttcccc caccagttca tcaacccccg taccaacatg     720

accgctcaca tcaacgtgcc ctacgtgggt atcaaccgtt acgaccagta cgctctgcac     780

aagccctgga ccctggtcgt gatggtggtg gctcccctga ccgtcaagac cggtggctcc     840

gagcagatca aggtgtacat gaacgctgct cccacctacg tgcacgtggc cggcgagctg     900

ccctccaaag aaggcatcgt ccccgtcgct tgcgctgacg gttacggcaa catggtcacc     960

accgacccca agaccgctga ccccgtgtac ggcaaggtgt tcaacccccc tcgtaccaac    1020

ctgcccggtc gttttaccaa cttcctcgac gtggccgagg cttgccccac cttcctgcgt    1080

ttcggcgagg tccccttcgt caagactgtg aactccggcg accgtctgct ggctaagttc    1140

gacgtgtccc tggctgctgg tcacatgtcc aacacctacc tggctggcct ggctcagtac    1200

tacacccagt actccggcac catgaacgtc cacttcatgt tcaccggtcc caccgacgct    1260

aaggctcgtt acatggtggc ttacgtgccc cctggcatga cccccccctac cgaccctgaa    1320

cacgctgctc actgcatcca ctccgagtgg gacaccggcc tgaactccaa gttcaccttc    1380
```

```
tccatccctt acctgtccgc tgctgactac gcctacaccg cttccgatgt cgccgagact   1440
acctccgtgc agggctgggt ttgcatctac cagatcaccc acggcaaggc tgagggcgac   1500
gctctggtgg tgtccgtgtc cgctggcaag gacttcgagt tccgtctgcc cgtggacgct   1560
cgtcagcaga ccaccaccac cggcgagtcc gctgacccag tgaccaccac cgtggaaaac   1620
tacggtggcg agactcagac cgctcgtcgc ctgcacaccg acgtggcctt catcctggac   1680
cgtttcgtga agctgaccgc tcccaagaac atccagaccc tggacctgat gcagatcccc   1740
tcccacaccc tcgtgggcgc tctgctgcgt tccgctacct actacttctc cgacctggaa   1800
gtcgctctgg tccacaccgg tcccgtgacc tgggtgccca acggtgctcc caaggacgct   1860
ctgaacaacc agaccaaccc caccgcttac cagaagcagc ccatcacccg cctggctctg   1920
ccttacaccg ctccccaccg tgtcctggct actgtgtaca acggcaagac cgcttacggc   1980
gaaaccacct cccgtcgtgg cgacatggct gctctggctc agcgtctgtc cgctcgtctg   2040
cccacctcct tcaactacgg tgctgtgaag gctgacacca tcaccgagct gctgatccgt   2100
atgaagcgtg ctgagactta ctgcccccgt cccctgctgg ctctggacac cacccaggac   2160
cgtcgcaagc aagagatcat cgctcccgag aagcaggtcc tgaacttcga cctgctgaag   2220
ctggctggcg acgtcgagtc caaccccggt cccttcttct tcgctgacgt gcgttccaac   2280
ttctccaagc tggtggacac catcaaccag atgcaagagg acatgtccac caagcacggt   2340
cccgacttca accgtctggt gtccgctttc gaggaactgg ctaccggtgt caaggctatc   2400
cgtaccggcc tggacgaggc taagccctgg tacaagctga tcaagctgct gtcccgtctg   2460
tcctgcatgg ctgctgtcgc tgctcgttcc aaggaccccg tgctggtcgc tatcatgctg   2520
gccgacaccg gcttggagcg ccagcgtcct ctgaaggttc gcgctaagct gcctcagcaa   2580
gagggacctt acgctggtcc cctcgagcgt cagaagcccc tgaaggtcaa ggctaaggct   2640
cccgtggtca aagaaggccc ctacgagggt cccgtgaaga agcccgtcgc tctcaaggtc   2700
aaggccaaga acctgatcgt gaccgagtcc ggtgctcccc ccaccgacct gcaaaagatg   2760
gtcatgggca acaccaagcc cgtcgagctg atcctggacg gaaagaccgt ggctatctgc   2820
tgcgctaccg gcgtgttcgg aaccgcttac ctggtgcccc gtcacctgtt cgctgagaag   2880
tacgacaaga tcatgctgga cggtcgtgct atgaccgact ccgactaccg tgtgttcgag   2940
ttcgagatca aggtcaaggg ccaggacatg ctctccgacg ctgctctgat ggtgctgcac   3000
cgtggcaacc gtgtgcgtga catcaccaag cacttccgtg acaccgctcg tatgaagaag   3060
ggcacccccg tcgtcggtgt cgtgaacaac gctgacgtgg gtcgtctgat cttctccggc   3120
gaggctctga cctacaagga catcgtcgtg tgcatggacg gcgataccat gcctggcctg   3180
ttcgcttaca aggctgctac caaggctggt tactgcggtg gtgctgtgct ggccaaggac   3240
ggtgctgaca ccttcatcgt gggcacccac tccgctggtg gcaacggtgt cggttactgc   3300
tcctgcgtgt cccgttccat gctgctgcgt atgaaggctc acgtggaccc cgagccccag   3360
cacgag                                                               3366
```

<210> SEQ ID NO 12
<211> LENGTH: 1126
<212> TYPE: PRT
<213> ORGANISM: artificial sequence
<220> FEATURE:
<223> OTHER INFORMATION: Wild-type polyprotein of FMDV Iraq strain

<400> SEQUENCE: 12

Met Gly Ala Gly Gln Ser Ser Pro Ala Thr Gly Ser Gln Asn Gln Ser

-continued

```
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ser Thr Gln Glu Asp His
        115                 120                 125

Val Ser Gly Pro Asn Thr Ser Gly Leu Glu Thr Arg Val Val Gln Ala
    130                 135                 140

Glu Arg Phe Phe Lys Lys His Leu Phe Asp Trp Thr Pro Asp Lys Ala
145                 150                 155                 160

Phe Gly His Leu Glu Lys Leu Glu Leu Pro Thr Asp His Lys Gly Val
                165                 170                 175

Tyr Gly His Leu Val Asp Ser Phe Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Thr Pro Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Val Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Thr Asn Thr Val Ser Ala Gly Gln Ile Lys Val Tyr Ala Asn
        275                 280                 285

Ile Ala Pro Thr His Val His Val Ala Gly Glu Leu Pro Ser Lys Glu
    290                 295                 300

Gly Ile Val Pro Val Ala Cys Ser Asp Gly Tyr Gly Gly Leu Val Thr
305                 310                 315                 320

Thr Asp Pro Lys Thr Ala Asp Pro Val Tyr Gly Met Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Glu Gly Lys Pro Tyr Val
        355                 360                 365

Val Thr Arg Thr Asp Glu Gln Arg Leu Leu Ala Lys Phe Asp Val Ser
    370                 375                 380

Leu Ala Ala Lys His Met Ser Asn Thr Tyr Leu Ser Gly Ile Ala Gln
385                 390                 395                 400

Tyr Tyr Ala Gln Tyr Ser Gly Thr Ile Asn Leu His Phe Met Phe Thr
                405                 410                 415

Gly Ser Thr Asp Ser Lys Ala Arg Tyr Met Val Ala Tyr Val Pro Pro
            420                 425                 430
```

-continued

```
Gly Val Glu Thr Pro Pro Asp Thr Pro Glu Lys Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Val Ala
465                 470                 475                 480

Glu Thr Thr Asn Val Gln Gly Trp Val Cys Ile Tyr Gln Ile Thr His
                485                 490                 495

Gly Lys Ala Glu Gln Asp Thr Leu Val Val Ser Val Ser Ala Gly Lys
            500                 505                 510

Asp Phe Glu Leu Arg Leu Pro Ile Asp Pro Arg Ser Gln Thr Thr Thr
        515                 520                 525

Thr Gly Glu Ser Ala Asp Pro Val Thr Thr Thr Val Glu Asn Tyr Gly
    530                 535                 540

Gly Glu Thr Gln Val Gln Arg Arg Gln His Thr Asp Val Thr Phe Ile
545                 550                 555                 560

Met Asp Arg Phe Val Lys Ile Gln Asn Leu Asn Pro Thr His Val Ile
                565                 570                 575

Asp Leu Met Gln Thr His Gln His Gly Leu Val Gly Ala Leu Leu Arg
            580                 585                 590

Ala Ala Thr Tyr Tyr Phe Ser Asp Leu Glu Ile Val Val Arg His Asp
        595                 600                 605

Gly Asn Leu Thr Trp Val Pro Asn Gly Ala Pro Glu Ala Ala Leu Ser
    610                 615                 620

Asn Thr Gly Asn Pro Thr Ala Tyr Leu Lys Ala Pro Phe Thr Arg Leu
625                 630                 635                 640

Ala Leu Pro Tyr Thr Ala Pro His Arg Val Leu Ala Thr Val Tyr Asn
                645                 650                 655

Gly Thr Ser Lys Tyr Ser Ala Gly Gly Thr Gly Arg Arg Gly Asp Leu
            660                 665                 670

Gly Pro Leu Ala Ala Arg Val Ala Ala Gln Leu Pro Ala Ser Phe Asn
        675                 680                 685

Phe Gly Ala Ile Gln Ala Thr Thr Ile His Glu Leu Leu Val Arg Met
    690                 695                 700

Lys Arg Ala Glu Leu Tyr Cys Pro Arg Pro Leu Leu Ala Val Glu Val
705                 710                 715                 720

Ser Ser Gln Asp Arg His Lys Gln Lys Ile Ile Ala Pro Ala Lys Gln
                725                 730                 735

Leu Leu Asn Phe Asp Leu Leu Lys Leu Ala Gly Asp Val Glu Ser Asn
            740                 745                 750

Pro Gly Pro Phe Phe Phe Ala Asp Val Arg Ser Asn Phe Ser Lys Leu
        755                 760                 765

Val Asp Thr Ile Asn Gln Met Gln Glu Asp Met Ser Thr Lys His Gly
    770                 775                 780

Pro Asp Phe Asn Arg Leu Val Ser Ala Phe Glu Glu Leu Ala Thr Gly
785                 790                 795                 800

Val Lys Ala Ile Arg Thr Gly Leu Asp Glu Ala Lys Pro Trp Tyr Lys
                805                 810                 815

Leu Ile Lys Leu Leu Ser Arg Leu Ser Cys Met Ala Ala Val Ala Ala
            820                 825                 830

Arg Ser Lys Asp Pro Val Leu Val Ala Ile Met Leu Ala Asp Thr Gly
        835                 840                 845
```

```
Leu Glu Arg Gln Arg Pro Leu Lys Val Arg Ala Lys Leu Pro Gln Gln
    850                 855                 860

Glu Gly Pro Tyr Ala Gly Pro Leu Glu Arg Gln Lys Pro Leu Lys Val
865                 870                 875                 880

Lys Ala Lys Ala Pro Val Val Lys Glu Gly Pro Tyr Glu Gly Pro Val
                885                 890                 895

Lys Lys Pro Val Ala Leu Lys Val Lys Ala Lys Asn Leu Ile Val Thr
            900                 905                 910

Glu Ser Gly Ala Pro Pro Thr Asp Leu Gln Lys Met Val Met Gly Asn
        915                 920                 925

Thr Lys Pro Val Glu Leu Ile Leu Asp Gly Lys Thr Val Ala Ile Cys
    930                 935                 940

Cys Ala Thr Gly Val Phe Gly Thr Ala Tyr Leu Val Pro Arg His Leu
945                 950                 955                 960

Phe Ala Glu Lys Tyr Asp Lys Ile Met Leu Asp Gly Arg Ala Met Thr
                965                 970                 975

Asp Ser Asp Tyr Arg Val Phe Glu Phe Glu Ile Lys Val Lys Gly Gln
            980                 985                 990

Asp Met Leu Ser Asp Ala Ala Leu  Met Val Leu His Arg  Gly Asn Arg
        995                 1000                1005

Val Arg  Asp Ile Thr Lys His  Phe Arg Asp Thr Ala  Arg Met Lys
    1010                 1015                1020

Lys Gly  Thr Pro Val Val Gly  Val Val Asn Asn Ala  Asp Val Gly
    1025                 1030                1035

Arg Leu  Ile Phe Ser Gly Glu  Ala Leu Thr Tyr Lys  Asp Ile Val
    1040                 1045                1050

Val Cys  Met Asp Gly Asp Thr  Met Pro Gly Leu Phe  Ala Tyr Lys
    1055                 1060                1065

Ala Ala  Thr Lys Ala Gly Tyr  Cys Gly Gly Ala Val  Leu Ala Lys
    1070                 1075                1080

Asp Gly  Ala Asp Thr Phe Ile  Val Gly Thr His Ser  Ala Gly Gly
    1085                 1090                1095

Asn Gly  Val Gly Tyr Cys Ser  Cys Val Ser Arg Ser  Met Leu Leu
    1100                 1105                1110

Arg Met  Lys Ala His Val Asp  Pro Glu Pro Gln His  Glu
    1115                 1120                1125


<210> SEQ ID NO 13
<211> LENGTH: 1122
<212> TYPE: PRT
<213> ORGANISM: artificial sequence
<220> FEATURE:
<223> OTHER INFORMATION: Wild-type polyprotein of FMDV Asia strain

<400> SEQUENCE: 13

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Asn Asn Thr Gln
    50                  55                  60

Asn Asn Asp Trp Phe Ser Arg Leu Ala Ser Ser Ala Phe Ser Gly Leu
65                  70                  75                  80
```

-continued

```
Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Val Ala Glu Asp Ala
        115                 120                 125

Val Ser Gly Pro Asn Thr Ser Gly Leu Glu Thr Arg Val Gln Gln Ala
    130                 135                 140

Glu Arg Phe Phe Lys Lys His Leu Phe Asp Trp Thr Pro Asn Leu Ala
145                 150                 155                 160

Phe Gly His Cys Tyr Tyr Leu Glu Leu Pro Thr Glu His Lys Gly Val
                165                 170                 175

Tyr Gly Ser Leu Met Gly Ser Tyr Ala Tyr Met Arg Asn Gly Trp Asp
            180                 185                 190

Ile Glu Val Thr Ala Val Gly Asn Gln Phe Asn Gly Gly Cys Leu Leu
        195                 200                 205

Val Ala Leu Val Pro Glu Leu Lys Glu Leu Asp Thr Arg Gln Lys Tyr
    210                 215                 220

Gln Leu Thr Leu Phe Pro His Gln Phe Ile Asn Pro Arg Thr Asn Met
225                 230                 235                 240

Thr Ala His Ile Asn Val Pro Tyr Val Gly Ile Asn Arg Tyr Asp Gln
                245                 250                 255

Tyr Ala Leu His Lys Pro Trp Thr Leu Val Val Met Val Val Ala Pro
            260                 265                 270

Leu Thr Val Lys Thr Gly Gly Ser Glu Gln Ile Lys Val Tyr Met Asn
        275                 280                 285

Ala Ala Pro Thr Tyr Val His Val Ala Gly Glu Leu Pro Ser Lys Glu
    290                 295                 300

Gly Ile Val Pro Val Ala Cys Ala Asp Gly Tyr Gly Asn Met Val Thr
305                 310                 315                 320

Thr Asp Pro Lys Thr Ala Asp Pro Val Tyr Gly Lys Val Phe Asn Pro
                325                 330                 335

Pro Arg Thr Asn Leu Pro Gly Arg Phe Thr Asn Phe Leu Asp Val Ala
            340                 345                 350

Glu Ala Cys Pro Thr Phe Leu Arg Phe Gly Glu Val Pro Phe Val Lys
        355                 360                 365

Thr Val Asn Ser Gly Asp Arg Leu Leu Ala Lys Phe Asp Val Ser Leu
    370                 375                 380

Ala Ala Gly His Met Ser Asn Thr Tyr Leu Ala Gly Leu Ala Gln Tyr
385                 390                 395                 400

Tyr Thr Gln Tyr Ser Gly Thr Met Asn Val His Phe Met Phe Thr Gly
                405                 410                 415

Pro Thr Asp Ala Lys Ala Arg Tyr Met Val Ala Tyr Val Pro Pro Gly
            420                 425                 430

Met Thr Pro Pro Thr Asp Pro Glu His Ala Ala His Cys Ile His Ser
        435                 440                 445

Glu Trp Asp Thr Gly Leu Asn Ser Lys Phe Thr Phe Ser Ile Pro Tyr
    450                 455                 460

Leu Ser Ala Ala Asp Tyr Ala Tyr Thr Ala Ser Asp Val Ala Glu Thr
465                 470                 475                 480

Thr Ser Val Gln Gly Trp Val Cys Ile Tyr Gln Ile Thr His Gly Lys
                485                 490                 495

Ala Glu Gly Asp Ala Leu Val Val Ser Val Ser Ala Gly Lys Asp Phe
```

```
            500                 505                 510

Glu Phe Arg Leu Pro Val Asp Ala Arg Gln Gln Thr Thr Thr Thr Gly
        515                 520                 525

Glu Ser Ala Asp Pro Val Thr Thr Thr Val Glu Asn Tyr Gly Gly Glu
    530                 535                 540

Thr Gln Thr Ala Arg Arg Leu His Thr Asp Val Ala Phe Ile Leu Asp
545                 550                 555                 560

Arg Phe Val Lys Leu Thr Ala Pro Lys Asn Ile Gln Thr Leu Asp Leu
                565                 570                 575

Met Gln Ile Pro Ser His Thr Leu Val Gly Ala Leu Leu Arg Ser Ala
            580                 585                 590

Thr Tyr Tyr Phe Ser Asp Leu Glu Val Ala Leu Val His Thr Gly Pro
        595                 600                 605

Val Thr Trp Val Pro Asn Gly Ala Pro Lys Asp Ala Leu Asn Asn Gln
    610                 615                 620

Thr Asn Pro Thr Ala Tyr Gln Lys Gln Pro Ile Thr Arg Leu Ala Leu
625                 630                 635                 640

Pro Tyr Thr Ala Pro His Arg Val Leu Ala Thr Val Tyr Asn Gly Lys
                645                 650                 655

Thr Ala Tyr Gly Glu Thr Thr Ser Arg Arg Gly Asp Met Ala Ala Leu
            660                 665                 670

Ala Gln Arg Leu Ser Ala Arg Leu Pro Thr Ser Phe Asn Tyr Gly Ala
        675                 680                 685

Val Lys Ala Asp Thr Ile Thr Glu Leu Leu Ile Arg Met Lys Arg Ala
    690                 695                 700

Glu Thr Tyr Cys Pro Arg Pro Leu Leu Ala Leu Asp Thr Thr Gln Asp
705                 710                 715                 720

Arg Arg Lys Gln Glu Ile Ile Ala Pro Glu Lys Gln Val Leu Asn Phe
                725                 730                 735

Asp Leu Leu Lys Leu Ala Gly Asp Val Glu Ser Asn Pro Gly Pro Phe
            740                 745                 750

Phe Phe Ala Asp Val Arg Ser Asn Phe Ser Lys Leu Val Asp Thr Ile
        755                 760                 765

Asn Gln Met Gln Glu Asp Met Ser Thr Lys His Gly Pro Asp Phe Asn
    770                 775                 780

Arg Leu Val Ser Ala Phe Glu Glu Leu Ala Thr Gly Val Lys Ala Ile
785                 790                 795                 800

Arg Thr Gly Leu Asp Glu Ala Lys Pro Trp Tyr Lys Leu Ile Lys Leu
                805                 810                 815

Leu Ser Arg Leu Ser Cys Met Ala Ala Val Ala Ala Arg Ser Lys Asp
            820                 825                 830

Pro Val Leu Val Ala Ile Met Leu Ala Asp Thr Gly Leu Glu Arg Gln
        835                 840                 845

Arg Pro Leu Lys Val Arg Ala Lys Leu Pro Gln Gln Glu Gly Pro Tyr
    850                 855                 860

Ala Gly Pro Leu Glu Arg Gln Lys Pro Leu Lys Val Lys Ala Lys Ala
865                 870                 875                 880

Pro Val Val Lys Glu Gly Pro Tyr Glu Gly Pro Val Lys Lys Pro Val
                885                 890                 895

Ala Leu Lys Val Lys Ala Lys Asn Leu Ile Val Thr Glu Ser Gly Ala
            900                 905                 910

Pro Pro Thr Asp Leu Gln Lys Met Val Met Gly Asn Thr Lys Pro Val
        915                 920                 925
```

```
Glu Leu Ile Leu Asp Gly Lys Thr Val Ala Ile Cys Cys Ala Thr Gly
    930                 935                 940

Val Phe Gly Thr Ala Tyr Leu Val Pro Arg His Leu Phe Ala Glu Lys
945                 950                 955                 960

Tyr Asp Lys Ile Met Leu Asp Gly Arg Ala Met Thr Asp Ser Asp Tyr
                965                 970                 975

Arg Val Phe Glu Phe Glu Ile Lys Val Lys Gly Gln Asp Met Leu Ser
            980                 985                 990

Asp Ala Ala Leu Met Val Leu His  Arg Gly Asn Arg Val  Arg Asp Ile
        995                 1000                1005

Thr Lys  His Phe Arg Asp Thr  Ala Arg Met Lys Lys  Gly Thr Pro
    1010                1015                1020

Val Val  Gly Val Val Asn Asn  Ala Asp Val Gly Arg  Leu Ile Phe
    1025                1030                1035

Ser Gly  Glu Ala Leu Thr Tyr  Lys Asp Ile Val Val  Cys Met Asp
    1040                1045                1050

Gly Asp  Thr Met Pro Gly Leu  Phe Ala Tyr Lys Ala  Ala Thr Lys
    1055                1060                1065

Ala Gly  Tyr Cys Gly Gly Ala  Val Leu Ala Lys Asp  Gly Ala Asp
    1070                1075                1080

Thr Phe  Ile Val Gly Thr His  Ser Ala Gly Gly Asn  Gly Val Gly
    1085                1090                1095

Tyr Cys  Ser Cys Val Ser Arg  Ser Met Leu Leu Arg  Met Lys Ala
    1100                1105                1110

His Val  Asp Pro Glu Pro Gln  His Glu
    1115                1120
```

<210> SEQ ID NO 14
<211> LENGTH: 3378
<212> TYPE: DNA
<213> ORGANISM: artificial sequence
<220> FEATURE:
<223> OTHER INFORMATION: Polynucleotide encoding wild-type polyprotein
      of FMDV Iraq strain

<400> SEQUENCE: 14

```
atgggtgctg gccagtcctc ccccgctacc ggttcccaga accagtccgg caacaccggt     60

tccatcatca acaactacta catgcagcag taccagaact ccatggacac ccaactcggc    120

gacaacgcta tctccggtgg ttccaacgag ggttccaccg acaccacctc tacccacacc    180

accaacaccc agaacaacga ctggttctcc aagctggctt cctccgcttt ctccggcctg    240

ttcggtgctc tgctggctga caagaagacc gaggaaacca ccctgctcga ggaccgtatc    300

ctgaccaccc gtaacggtca caccacctcc accacccagt cctccgtggg tgttacctac    360

ggttactcca cccaagagga ccacgtgtcc ggtcccaaca cctccggcct ggaaacccgt    420

gtggtgcagg ctgagcgctt cttcaagaag cacctgttcg actggacccc cgacaaggct    480

ttcggtcacc tcgagaagct cgagctgccc accgaccaca agggcgtgta cggtcacctg    540

gtggacagct tcgcttacat gcgtaacggc tgggacgtcg aggtgtccgc tgtgggcaac    600

cagttcaacg gtggttgcct gctggtggct atggtgcccg agtggaaaga attcacccct    660

cgcgagaagt accagctgac cctgttcccc caccagttca tctccccccg taccaacatg    720

accgctcaca tcgtggtgcc ctacctgggt gtcaaccgtt acgaccagta caagaagcac    780

aagccctgga ccctggtggt tatggtggtg tctcccctga ccactaacac cgtgtccgct    840
```

-continued

```
ggccagatca aggtgtacgc taacatcgct cccacccacg tgcacgtcgc gggcgagctg    900
ccttccaaag aaggcatcgt ccccgtcgct tgctccgacg gttacggtgg cctggtcacc    960
accgacccca agaccgctga ccccgtgtac ggcatggtgt acaacccccc tcgcaccaac   1020
taccccggtc gtttcaccaa cctgctggac gtggccgagg cttgccccac cttcctgtgc   1080
ttcgacgagg gcaagcccta cgtggtcacc cgtaccgacg agcagcgtct gctggctaag   1140
ttcgacgtgt ccctggctgc taagcacatg tccaacacct acctgtccgg tatcgctcag   1200
tactacgccc agtactccgg caccatcaac ctgcacttca tgttcaccgg ctccaccgat   1260
tccaaggctc gttacatggt ggcttacgtg ccccctggtg tcgagactcc ccccgacacc   1320
cctgagaagg ctgctcactg catccacgct gagtgggaca ccggcctgaa ctccaagttc   1380
accttctcca tcccttacgt gtccgccgct gactacgctt acaccgcttc cgacgtcgcc   1440
gagactacca acgtgcaggg ctgggtctgc atctaccaga tcacccacgg caaggctgag   1500
caggacaccc tggtcgtgtc cgtgtctgct ggcaaggact tcgaactccg tctgcccatc   1560
gacccccgtt cccagaccac caccaccggc gagtctgccg accctgtgac caccaccgtg   1620
gaaaactacg gtggcgagac tcaggtgcag cgtcgtcagc acaccgacgt gaccttcatc   1680
atggaccgtt tcgtgaagat ccagaacctg aaccctaccc acgtgatcga cctgatgcag   1740
actcaccagc acggcctcgt gggcgctctg ctgcgtgctg ctacctacta cttctccgac   1800
ctcgagatcg tcgtccgtca cgacggcaac ctgacctggg tgcccaacgg tgctcccgag   1860
gctgctctgt ctaacaccgg caaccccacc gcttacctga aggctccctt cacccgtctg   1920
gctctgccct acaccgctcc ccaccgtgtg ctggctaccg tgtacaacgg cacctccaag   1980
tactccgctg gtggcaccgg tcgtcgtggc gacttgggtc ctctggctgc tcgtgtggct   2040
gctcagctgc ccgcttcctt caacttcggt gctatccagg ctaccaccat ccacgaactc   2100
ctcgtgcgta tgaagcgtgc tgagctgtac tgcccccgtc ccctgctggc tgtggaagtg   2160
tcctcccagg accgtcacaa gcagaagatc atcgctcccg ctaagcagct gctgaacttc   2220
gacctgctga agctggctgg cgacgtggaa tccaaccccg gtcccttctt cttcgctgac   2280
gtgcgttcca acttctctaa gctggtggac actatcaacc agatgcaaga ggacatgtcc   2340
accaagcacg gtcccgactt caaccgtctg gtgtccgctt tcgaggaact ggctaccggt   2400
gtcaaggcta tccgtaccgg cctggacgag gctaagccct ggtacaagct gatcaagctg   2460
ctgtcccgtc tgtcctgcat ggctgctgtc gctgctcgtt ccaaggaccc cgtgctggtc   2520
gctatcatgc tggccgacac cggcttggag cgtcagcgtc ctctgaaagt ccgcgctaag   2580
ctgccccagc aagagggccc gtacgctggt cccctcgagc gtcagaagcc cctgaaggtt   2640
aaagccaagg ctcccgtggt caaagaaggc ccatacgagg gtcccgtgaa gaagcccgtc   2700
gctctcaagg tcaaggccaa gaacctgatc gtgaccgagt ccggtgctcc ccccaccgac   2760
ctgcaaaaga tggtcatggg caacaccaag cccgtcgagc tgatcctgga cggcaagacc   2820
gtggctatct gctgcgctac cggcgtgttc ggtactgctt acctggtgcc ccgtcacctg   2880
ttcgctgaga agtacgacaa gatcatgctg gacggtcgtg ctatgaccga ctccgactac   2940
cgtgtgttcg agttcgagat caaagtcaag ggccaggaca tgctgtccga cgctgctctg   3000
atggtgctgc accgtggcaa ccgtgtgcgt gacatcacca agcacttccg tgacaccgct   3060
cgtatgaaga agggcacccc cgtcgtcggt gtcgtgaaca acgctgacgt gggtcgtctg   3120
atcttctccg gcgaggctct gacctacaag gacatcgtcg tgtgcatgga tggcgacacc   3180
atgcctggcc tgttcgctta caaggctgct accaaggctg gttactgcgg tggtgctgtc   3240
```

```
ctggctaagg acggtgctga caccttcatc gtgggcaccc actccgctgg cggaaacggt   3300

gtcggttact gctcctgcgt gtcccgttcc atgctgctgc gcatgaaggc tcacgtggac   3360

cccgagcccc agcacgag                                                3378


<210> SEQ ID NO 15
<211> LENGTH: 3366
<212> TYPE: DNA
<213> ORGANISM: artificial sequence
<220> FEATURE:
<223> OTHER INFORMATION: Polynucleotide encoding wild-type polyprotein
      of FMDV Asia strain

<400> SEQUENCE: 15

atgggtgctg gccagtcctc ccctgctacc ggttcccaga accagtccgg caacaccggt     60

tccatcatca acaactacta catgcagcag taccagaact ccatggacac ccagctcggc    120

gacaacgcta tctccggtgg ttccaacgag ggttccaccg acaccacctc cacccacacc    180

aacaacaccc agaacaacga ctggttctcc cgtctggctt cctccgcttt ctccggcctg    240

ttcggtgctc tgctggctga caagaagacc gaggaaacca ccctgctcga ggaccgtatc    300

ctgaccaccc gtaacggtca caccacctct accacccagt cctctgtggg tgtcacctac    360

ggttacgctg tggctgagga cgctgtgtcc ggtcccaaca cctccggcct ggaaacccgt    420

gtgcagcagg ctgagcgctt cttcaagaag cacctgttcg actggacccc caacctggct    480

ttcggtcact gctactacct cgagctgccc accgagcaca agggcgtgta cggttccctg    540

atgggctcct acgcttacat gcgtaacggc tgggacatcg aagtgaccgc tgtgggcaac    600

cagttcaacg gtggttgcct gctggtggct ctggtgcccg agctgaaaga actggacacc    660

cgtcagaagt accagctgac cctgttcccc caccagttca tcaacccccg taccaacatg    720

accgctcaca tcaacgtgcc ctacgtgggt atcaaccgtt acgaccagta cgctctgcac    780

aagccctgga ccctggtcgt gatggtggtg gctcccctga ccgtcaagac cggtggctcc    840

gagcagatca aggtgtacat gaacgctgct cccacctacg tgcacgtggc cggcgagctg    900

ccctccaaag aaggcatcgt ccccgtcgct tgcgctgacg gttacggcaa catggtcacc    960

accgacccca agaccgctga ccccgtgtac ggcaaggtgt tcaacccccc tcgtaccaac   1020

ctgcccggtc gttttaccaa cttcctcgac gtggccgagg cttgccccac cttcctgcgt   1080

ttcggcgagg tccccttcgt caagactgtg aactccggcg accgtctgct ggctaagttc   1140

gacgtgtccc tggctgctgg tcacatgtcc aacacctacc tggctggcct ggctcagtac   1200

tacacccagt actccggcac catgaacgtc cacttcatgt tcaccggtcc caccgacgct   1260

aaggctcgtt acatggtggc ttacgtgccc cctggcatga cccccccctac cgaccctgaa   1320

cacgctgctc actgcatcca ctccgagtgg gacaccggcc tgaactccaa gttcaccttc   1380

tccatccctt acctgtccgc tgctgactac gcctacaccg cttccgatgt cgccgagact   1440

acctccgtgc agggctgggt ttgcatctac cagatcaccc acggcaaggc tgagggcgac   1500

gctctggtgg tgtccgtgtc cgctggcaag gacttcgagt tccgtctgcc cgtggacgct   1560

cgtcagcaga ccaccaccac cggcgagtcc gctgacccag tgaccaccac cgtggaaaac   1620

tacggtggcg agactcagac cgctcgtcgc ctgcacaccg acgtggcctt catcctggac   1680

cgtttcgtga agctgaccgc tcccaagaac atccagaccc tggacctgat gcagatcccc   1740

tcccacaccc tcgtgggcgc tctgctgcgt tccgctacct actacttctc cgacctggaa   1800

gtcgctctgg tccacaccgg tcccgtgacc tgggtgccca acggtgctcc caaggacgct   1860
```

```
ctgaacaacc agaccaaccc caccgcttac cagaagcagc ccatcacccg cctggctctg   1920

ccttacaccg ctccccaccg tgtcctggct actgtgtaca acggcaagac cgcttacggc   1980

gaaaccacct cccgtcgtgg cgacatggct gctctggctc agcgtctgtc cgctcgtctg   2040

cccacctcct tcaactacgg tgctgtgaag gctgacacca tcaccgagct gctgatccgt   2100

atgaagcgtg ctgagactta ctgccccgt cccctgctgg ctctggacac cacccaggac    2160

cgtcgcaagc aagagatcat cgctcccgag aagcaggtcc tgaacttcga cctgctgaag   2220

ctggctggcg acgtcgagtc caaccccggt cccttcttct tcgctgacgt gcgttccaac   2280

ttctccaagc tggtggacac catcaaccag atgcaagagg acatgtccac caagcacggt   2340

cccgacttca accgtctggt gtccgctttc gaggaactgg ctaccggtgt caaggctatc   2400

cgtaccggcc tggacgaggc taagccctgg tacaagctga tcaagctgct gtcccgtctg   2460

tcctgcatgg ctgctgtcgc tgctcgttcc aaggaccccg tgctggtcgc tatcatgctg   2520

gccgacaccg gcttggagcg ccagcgtcct ctgaaggttc gcgctaagct gcctcagcaa   2580

gagggacctt acgctggtcc cctcgagcgt cagaagcccc tgaaggtcaa ggctaaggct   2640

cccgtggtca aagaaggccc ctacgagggt cccgtgaaga agcccgtcgc tctcaaggtc   2700

aaggccaaga acctgatcgt gaccgagtcc ggtgctcccc ccaccgacct gcaaaagatg   2760

gtcatgggca acaccaagcc cgtcgagctg atcctggacg gaaagaccgt ggctatctgc   2820

tgcgctaccg gcgtgttcgg aaccgcttac ctggtgcccc gtcacctgtt cgctgagaag   2880

tacgacaaga tcatgctgga cggtcgtgct atgaccgact ccgactaccg tgtgttcgag   2940

ttcgagatca aggtcaaggg ccaggacatg ctctccgacg ctgctctgat ggtgctgcac   3000

cgtggcaacc gtgtgcgtga catcaccaag cacttccgtg acaccgctcg tatgaagaag   3060

ggcacccccg tcgtcggtgt cgtgaacaac gctgacgtgg gtcgtctgat cttctccggc   3120

gaggctctga cctacaagga catcgtcgtg tgcatggacg gcgataccat gcctggcctg   3180

ttcgcttaca aggctgctac caaggctggt tactgcggtg gtgctgtgct ggccaaggac   3240

ggtgctgaca ccttcatcgt gggcacccac tccgctggtg gcaacggtgt cggttactgc   3300

tcctgcgtgt cccgttccat gctgctgcgt atgaaggctc acgtggaccc cgagccccag   3360

cacgag                                                              3366
```

<210> SEQ ID NO 16
<211> LENGTH: 1184
<212> TYPE: PRT
<213> ORGANISM: artificial sequence
<220> FEATURE:
<223> OTHER INFORMATION: FMDV capsid protein in adenovirus

<400> SEQUENCE: 16

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
```

```
                85                  90                  95

Glu Asp Arg Ile Leu Thr Thr Arg Asn Gly His Thr Thr Ser Thr Thr
            100                 105                 110

Gln Ser Ser Val Gly Val Thr His Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Tyr Lys Lys Tyr Leu Phe Asp Trp Thr Thr Asp Lys Ala
145                 150                 155                 160

Phe Gly His Leu Glu Lys Leu Glu Leu Pro Ser Asp His His Gly Val
                165                 170                 175

Phe Gly Cys Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Glu Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Val Ser Pro
            260                 265                 270

Leu Thr Val Asn Asn Thr Ser Ala Ala Gln Ile Lys Val Tyr Ala Asn
        275                 280                 285

Ile Ala Pro Thr Tyr Val His Val Ala Gly Glu Leu Pro Ser Lys Glu
    290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Ala Tyr Gly Lys Val Tyr Asn Pro
                325                 330                 335

Pro Arg Thr Asn Tyr Pro Gly Arg Phe Thr Asn Leu Leu Asp Val Ala
            340                 345                 350

Glu Ala Cys Pro Thr Phe Leu Cys Phe Asp Asp Gly Lys Pro Tyr Val
        355                 360                 365

Thr Thr Arg Thr Asp Asp Thr Arg Leu Leu Ala Lys Phe Asp Leu Ser
    370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Arg Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Ile Asn Val Gln Gly Trp Val Cys Ile Tyr Gln Ile Thr His
                485                 490                 495

Gly Lys Ala Glu Asn Asp Thr Leu Val Val Ser Val Ser Ala Gly Lys
            500                 505                 510
```

Asp Phe Glu Leu Arg Leu Pro Ile Asp Pro Arg Gln Gln Thr Thr Ala
515 520 525

Thr Gly Glu Ser Ala Asp Pro Val Thr Thr Thr Val Glu Asn Tyr Gly
530 535 540

Gly Glu Thr Gln Ile Gln Arg Arg His His Thr Asp Ile Gly Phe Ile
545 550 555 560

Met Asp Arg Phe Val Lys Ile Gln Ser Leu Ser Pro Thr His Val Ile
565 570 575

Asp Leu Met Gln Ala His Gln His Gly Leu Val Gly Ala Leu Leu Arg
580 585 590

Ala Ala Thr Tyr Tyr Phe Ser Asp Leu Glu Ile Val Val Arg His Glu
595 600 605

Gly Asn Leu Thr Trp Val Pro Asn Gly Ala Pro Glu Ser Ala Leu Leu
610 615 620

Asn Thr Ser Asn Pro Thr Ala Tyr Asn Lys Ala Pro Phe Thr Arg Leu
625 630 635 640

Ala Leu Pro Tyr Thr Ala Pro His Arg Val Leu Ala Thr Val Tyr Asn
645 650 655

Gly Thr Ser Lys Tyr Ala Val Gly Gly Ser Gly Arg Arg Gly Asp Met
660 665 670

Gly Ser Leu Ala Ala Arg Val Val Lys Gln Leu Pro Ala Ser Phe Asn
675 680 685

Tyr Gly Ala Ile Lys Ala Asp Ala Ile His Glu Leu Leu Val Arg Met
690 695 700

Lys Arg Ala Glu Leu Tyr Cys Pro Arg Pro Leu Leu Ala Ile Glu Val
705 710 715 720

Ser Ser Gln Asp Arg His Lys Gln Lys Ile Ile Ala Pro Ala Lys Gln
725 730 735

Leu Leu Asn Phe Asp Leu Leu Lys Leu Ala Gly Asp Val Glu Ser Asn
740 745 750

Pro Gly Pro Phe Phe Phe Ala Asp Val Arg Ser Asn Phe Ser Lys Leu
755 760 765

Val Asp Thr Ile Asn Gln Met Gln Glu Asp Met Ser Thr Lys His Gly
770 775 780

Pro Asp Phe Asn Arg Leu Val Ser Ala Phe Glu Glu Leu Ala Thr Gly
785 790 795 800

Val Lys Ala Ile Arg Thr Gly Leu Asp Glu Ala Lys Pro Trp Tyr Lys
805 810 815

Leu Ile Lys Leu Leu Ser Arg Leu Ser Cys Met Ala Ala Val Ala Ala
820 825 830

Arg Ser Lys Asp Pro Val Leu Val Ala Ile Met Leu Ala Asp Thr Gly
835 840 845

Leu Glu Ile Leu Asp Ser Thr Phe Val Val Lys Lys Ile Ser Asp Ser
850 855 860

Leu Ser Ser Leu Phe His Val Pro Ala Pro Val Phe Ser Phe Gly Ala
865 870 875 880

Pro Ile Leu Leu Ala Gly Leu Val Lys Val Ala Ser Ser Phe Phe Arg
885 890 895

Ser Thr Pro Glu Asp Leu Glu Arg Ala Glu Lys Gln Arg Gln Arg Pro
900 905 910

Leu Lys Val Arg Ala Lys Leu Pro Gln Gln Glu Gly Pro Tyr Ala Gly
915 920 925

```
Pro Leu Glu Arg Gln Lys Pro Leu Lys Val Lys Ala Lys Ala Pro Val
    930                 935                 940

Val Lys Glu Gly Pro Tyr Glu Gly Pro Val Lys Lys Pro Val Ala Leu
945                 950                 955                 960

Lys Val Lys Ala Lys Asn Leu Ile Val Thr Glu Ser Gly Ala Pro Pro
                965                 970                 975

Thr Asp Leu Gln Lys Met Val Met Gly Asn Thr Lys Pro Val Glu Leu
            980                 985                 990

Ile Leu Asp Gly Lys Thr Val Ala  Ile Cys Cys Ala Thr  Gly Val Phe
        995                 1000                 1005

Gly Thr  Ala Tyr Leu Val Pro  Arg His Leu Phe Ala  Glu Lys Tyr
    1010                 1015                 1020

Asp Lys  Ile Met Leu Asp Gly  Arg Ala Met Thr Asp  Ser Asp Tyr
    1025                 1030                 1035

Arg Val  Phe Glu Phe Glu Ile  Lys Val Lys Gly Gln  Asp Met Leu
    1040                 1045                 1050

Ser Asp  Ala Ala Leu Met Val  Leu His Arg Gly Asn  Arg Val Arg
    1055                 1060                 1065

Asp Ile  Thr Lys His Phe Arg  Asp Thr Ala Arg Met  Lys Lys Gly
    1070                 1075                 1080

Thr Pro  Val Val Gly Val Val  Asn Asn Ala Asp Val  Gly Arg Leu
    1085                 1090                 1095

Ile Phe  Ser Gly Glu Ala Leu  Thr Tyr Lys Asp Ile  Val Val Thr
    1100                 1105                 1110

Met Asp  Gly Asp Thr Met Pro  Gly Leu Phe Ala Tyr  Lys Ala Ala
    1115                 1120                 1125

Thr Lys  Ala Gly Tyr Cys Gly  Gly Ala Val Leu Ala  Lys Asp Gly
    1130                 1135                 1140

Ala Asp  Thr Phe Ile Val Gly  Thr His Ser Ala Gly  Gly Asn Gly
    1145                 1150                 1155

Val Gly  Tyr Cys Ser Cys Val  Ser Arg Ser Met Leu  Leu Arg Met
    1160                 1165                 1170

Lys Ala  His Val Asp Pro Glu  Pro Gln His Glu
    1175                 1180
```

<210> SEQ ID NO 17
<211> LENGTH: 3552
<212> TYPE: DNA
<213> ORGANISM: artificial sequence
<220> FEATURE:
<223> OTHER INFORMATION: Codon-optimized polynucleotide encoding FMDV capsid precursor

<400> SEQUENCE: 17

```
atgggggctg ggcagtcctc tcccgccaca ggctcacaga atcagtcagg caacacaggg     60

tctattatca acaattatta tatgcagcag taccagaact ccatggacac ccagctggga    120

gataacgcca tctccggcgg aagcaatgag ggtccacag acaccacaag cacccacacc    180

acaaacacac agaacaatga ttggttcagc aagctggcct ccagcgcttt taccggactc    240

ttcggggccc tgctcgctga caagaaaacc gaggaaacca cactgctcga ggatcgcatc    300

ctgaccacaa ggaacggcca caccacatcc accacacagt cttcagtggg agtcacccac    360

gggtacagca cagaggaaga ccatgtggcc ggcccaaata cctctggact ggaaacacgc    420

gtggtccagg ccgagcggtt ttacaagaaa tatctgttcg actggaccac agataaggcc    480

tttggccacc tggagaaact ggaactccct tcagatcacc atggcgtgtt cggatgtctg    540
```

```
gtcgactcct acgcctatat gcgcaacggc tgggatgtgg aagtctccgc cgtgggaaac    600
cagtttaatg gaggatgcct gctcgtggct atggtcccag agtggaagga attcgacacc    660
agggagaaat accagctgac actctttcct caccagttca tctcccccag aacaaacatg    720
accgcccata ttaccgtgcc atacctgggc gtcaatcgct acgaccagta taagaaacac    780
aagccttgga ccctggtggt catggtggtc tcacccctca cagtgaacaa tacctccgcc    840
gctcagatca aagtctacgc caacattgct cccacctatg tgcacgtcgc cggggaactg    900
ccatccaagg agggcatctt ccctgtggcc tgtgctgacg ggtacggagg gctggtcacc    960
acagacccca agaccgccga tccagcttac ggcaaagtgt ataacccccc aaggaccaat   1020
taccccggaa gattcacaaa cctgctcgat gtggccgagg cttgcccaac ctttctgtgt   1080
ttcgacgatg gaaagcctta cgtgaccaca agaacagacg atacccgact gctcgccaag   1140
ttcgacctga gcctcgccgc taaacacatg tctaacacct acctgtcagg gatcgcccag   1200
tactataccc agtattccgg cacaattaat ctgcatttta tgttcacagg atctaccgac   1260
tcaaaggcca gatacatggt ggcttatatc cctcccggag tcgaaacacc acctgacacc   1320
cctgagcgag ctgctcactg catccatgcc gaatgggata ccgggctgaa ctccaagttt   1380
acattcagca ttccctacgt gtctgccgct gactacgcct ataccgctag cgatacagcc   1440
gagaccatca acgtgcaggg gtgggtctgt atctaccaga ttacccacgg caaagccgaa   1500
aatgacacac tggtggtctc tgtgtcagcc gggaaggact tcgagctgcg actccccatc   1560
gatccacgac agcagaccac agctaccgga gagtccgctg accctgtgac cacaaccgtc   1620
gaaaactacg gcggagagac ccagattcag cgccggcacc atacagacat cggctttatt   1680
atggatcgct tcgtgaagat ccagtccctg agccccaccc acgtgattga cctcatgcag   1740
gctcaccagc atggactggt gggagctctg ctccgagctg ctacctacta tttctccgat   1800
ctggaaatcg tggtccggca tgagggaaac ctgacctggg tgcctaatgg ggcccccgag   1860
tcagctctgc tcaacacatc caatcccacc gcctacaaca aagctccatt caccagactg   1920
gccctcccat atacagctcc tcaccgagtg ctggctaccg tctacaatgg cacaagcaag   1980
tatgctgtgg gaggctctgg aaggagaggg gacatgggca gcctcgctgc tcgagtggtc   2040
aagcagctgc cagcttcttt caactacgga gccatcaaag ccgatgctat tcacgaactg   2100
ctcgtgcgaa tgaagcgcgc cgagctgtat tgccccaggc cactgctcgc catcgaggtg   2160
tccagccagg acagacataa gcagaaaatc attgccccag ctaagcagct gctcaacttt   2220
gacctgctca aactggccgg agatgtggaa agcaatcctg ggcccttctt tttcgccgac   2280
gtgaggtcca acttcagcaa actggtcgac accatcaatc agatgcagga ggatatgtca   2340
accaagcacg gccccgactt taaccggctg gtgtccgcct tcgaggaact cgctaccggc   2400
gtgaaggcca tcaggacagg actggacgag gccaaaccat ggtacaagct gatcaagctg   2460
ctctctcgcc tctcatgtat ggctgctgtg gctgctcgga gcaaggaccc cgtgctggtc   2520
gccatcatgc tcgctgacac cggcctggag attctcgatt ctacatttgt ggtcaagaaa   2580
atctctgact cactgtcttc actcttccac gtgccagccc ctgtcttttc cttcggagct   2640
ccaattctgc tcgctggact ggtgaaagtc gcctccagct tttccggtc caccccagag    2700
gacctggaaa gggccgagaa gcagcgtcag agacctctga aagtgagagc taagctccca   2760
cagcaggaag gaccttacgc tggcccgttg gagagacaga aaccgctgaa agtgaaagca   2820
aaagccccgg tcgtcaagga aggaccttac gagggaccgg tgaagaagcc tgtcgctttg   2880
```

```
aaagtgaaag ctaagaactt gatagtcact gagagtggtg ccccaccgac cgacttgcaa   2940

aagatggtca tgggcaacac aaagcctgtt gagctcatcc ttgacgggaa gacagtagcc   3000

atctgttgtg ctactggagt gtttggcact gcttacctcg tgcctcgtca tcttttcgca   3060

gagaagtatg acaagatcat gctggatggc agagccatga cagacagtga ctacagagtg   3120

tttgagtttg agattaaagt aaaaggacag gacatgctct cagacgctgc gctcatggtg   3180

ctccaccgtg ggaaccgcgt gagagatatc acgaaacact ttcgtgatac agcaagaatg   3240

aagaaaggca cccccgtcgt cggtgtggtc aacaacgccg acgttgggag actgattttc   3300

tctggtgagg ccctcaccta caaggatatt gtagtgacca tggacggaga caccatgcct   3360

ggcctctttg cctacaaagc cgccaccaag gcaggctact gtggaggagc cgttctcgcc   3420

aaggacgggg ccgacacttt catcgtcggc actcactccg caggaggcaa tggagttgga   3480

tactgctcat gcgtttccag gtccatgctt ctcagaatga aggcacacgt tgaccctgaa   3540

ccacaacacg ag                                                       3552
```

<210> SEQ ID NO 18
<211> LENGTH: 745
<212> TYPE: DNA
<213> ORGANISM: artificial sequence
<220> FEATURE:
<223> OTHER INFORMATION: CMV promoter

<400> SEQUENCE: 18

```
tttattaata gtaatcaatt acggggtcat tagttcatag cccatatatg gagttccgcg     60

ttacataact tacggtaaat ggcccgcctg gctgaccgcc caacgacccc cgcccattga    120

cgtcaataat gacgtatgtt cccatagtaa cgccaatagg gactttccat tgacgtcaat    180

gggtggagta tttacggtaa actgcccact tggcagtaca tcaagtgtat catatgccaa    240

gtacgccccc tattgacgtc aatgacggta aatggcccgc ctggcattat gcccagtaca    300

tgaccttatg ggactttcct acttggcagt acatctacgt attagtcatc gctattacca    360

tggtgatgcg gttttggcag tacatcaatg ggcgtggata gcggtttgac tcacggggat    420

ttccaagtct ccaccccatt gacgtcaatg ggagtttgtt ttggcaccaa aatcaacggg    480

actttccaaa atgtcgtaac aactccgccc cattgacgca aatgggcggt aggcgtgtac    540

ggtgggaggt ctatataagc agagctcgtt tagtgaaccg tcagatcgcc tggagacgcc    600

atccacgctg ttttgacctc catagaagac accgggaccg atccagcctc cgcggccggg    660

aacggtgcat tggaacgcgg attccccgtg ccaagagtga cgtaagtacc gcctatagag    720

tctataggcc cacccccttg gcttc                                          745
```

<210> SEQ ID NO 19
<211> LENGTH: 104
<212> TYPE: DNA
<213> ORGANISM: artificial sequence
<220> FEATURE:
<223> OTHER INFORMATION: Synthetic enhancer

<400> SEQUENCE: 19

```
cttgaggtgt ggcaggcttg agatctggcc atacacttga gtgacaatga catccacttt     60

gcctttctct ccacaggtgt ccactcccag gtccaactgc agcc                     104
```

<210> SEQ ID NO 20
<211> LENGTH: 4579
<212> TYPE: DNA
<213> ORGANISM: artificial sequence
<220> FEATURE:
<223> OTHER INFORMATION: CMV promoter -synthetic enhancer- codon optimized FMDV capsid gene - SV40 PolyA in vAD3027

<400> SEQUENCE: 20

```
tttattaata gtaatcaatt acggggtcat tagttcatag cccatatatg gagttccgcg     60
ttacataact tacggtaaat ggcccgcctg gctgaccgcc caacgacccc cgcccattga    120
cgtcaataat gacgtatgtt cccatagtaa cgccaatagg gactttccat tgacgtcaat    180
gggtggagta tttacggtaa actgcccact tggcagtaca tcaagtgtat catatgccaa    240
gtacgccccc tattgacgtc aatgacggta aatggcccgc ctggcattat gcccagtaca    300
tgaccttatg ggactttcct acttggcagt acatctacgt attagtcatc gctattacca    360
tggtgatgcg gttttggcag tacatcaatg ggcgtggata gcggtttgac tcacggggat    420
ttccaagtct ccaccccatt gacgtcaatg ggagtttgtt ttggcaccaa aatcaacggg    480
actttccaaa atgtcgtaac aactccgccc cattgacgca aatgggcggt aggcgtgtac    540
ggtgggaggt ctatataagc agagctcgtt tagtgaaccg tcagatcgcc tggagacgcc    600
atccacgctg ttttgacctc catagaagac accgggaccg atccagcctc cgcggccggg    660
aacggtgcat tggaacgcgg attccccgtg ccaagagtga cgtaagtacc gcctatagag    720
tctataggcc cacccccttg gcttccttga ggtgtggcag gcttgagatc tggccataca    780
cttgagtgac aatgacatcc actttgcctt tctctccaca ggtgtccact cccaggtcca    840
actgcagccg cggccgcatg gggctgggc agtcctctcc cgccacaggc tcacagaatc    900
agtcaggcaa cacagggtct attatcaaca attattatat gcagcagtac cagaactcca    960
tggacaccca gctgggagat aacgccatct ccggcggaag caatgagggg tccacagaca   1020
ccacaagcac ccacaccaca aacacacaga acaatgattg gttcagcaag ctggcctcca   1080
gcgcttttac cggactcttc ggggccctgc tcgctgacaa gaaaaccgag gaaaccacac   1140
tgctcgagga tcgcatcctg accacaagga acggccacac cacatccacc acacagtctt   1200
cagtgggagt cacccacggg tacagcacag aggaagacca tgtggccggc ccaaatacct   1260
ctggactgga aacacgcgtg gtccaggccg agcggtttta caagaaatat ctgttcgact   1320
ggaccacaga taaggccttt ggccacctgg agaaactgga actcccttca gatcaccatg   1380
gcgtgttcgg atgtctggtc gactcctacg cctatatgcg caacggctgg gatgtggaag   1440
tctccgccgt gggaaaccag tttaatggag gatgcctgct cgtggctatg gtcccagagt   1500
ggaaggaatt cgacaccagg gagaaatacc agctgacact ctttcctcac cagttcatct   1560
cccccagaac aaacatgacc gcccatatta ccgtgccata cctgggcgtc aatcgctacg   1620
accagtataa gaaacacaag ccttggaccc tggtggtcat ggtggtctca cccctcacag   1680
tgaacaatac ctccgccgct cagatcaaag tctacgccaa cattgctccc acctatgtgc   1740
acgtcgccgg ggaactgcca tccaaggagg gcatcttccc tgtggcctgt gctgacgggt   1800
acggagggct ggtcaccaca gaccccaaga ccgccgatcc agcttacggc aaagtgtata   1860
accccccaag gaccaattac cccggaagat tcacaaacct gctcgatgtg gccgaggctt   1920
gcccaacctt tctgtgtttc gacgatggaa agccttacgt gaccacaaga acagacgata   1980
cccgactgct cgccaagttc gacctgagcc tcgccgctaa acacatgtct aacacctacc   2040
tgtcagggat cgcccagtac tatacccagt attccggcac aattaatctg cattttatgt   2100
tcacaggatc taccgactca aaggccagat acatggtggc ttatatccct cccggagtcg   2160
aaacaccacc tgacacccct gagcgagctg ctcactgcat ccatgccgaa tgggataccg   2220
```

-continued

```
ggctgaactc caagtttaca ttcagcattc cctacgtgtc tgccgctgac tacgcctata   2280
ccgctagcga tacagccgag accatcaacg tgcaggggtg ggtctgtatc taccagatta   2340
cccacggcaa agccgaaaat gacacactgg tggtctctgt gtcagccggg aaggacttcg   2400
agctgcgact ccccatcgat ccacgacagc agaccacagc taccggagag tccgctgacc   2460
ctgtgaccac aaccgtcgaa aactacggcg gagagaccca gattcagcgc cggcaccata   2520
cagacatcgg ctttattatg gatcgcttcg tgaagatcca gtccctgagc cccacccacg   2580
tgattgacct catgcaggct caccagcatg gactggtggg agctctgctc cgagctgcta   2640
cctactattt ctccgatctg gaaatcgtgg tccggcatga gggaaacctg acctgggtgc   2700
ctaatggggc ccccgagtca gctctgctca acacatccaa tcccaccgcc tacaacaaag   2760
ctccattcac cagactggcc ctcccatata cagctcctca ccgagtgctg gctaccgtct   2820
acaatggcac aagcaagtat gctgtgggag gctctggaag gagaggggac atgggcagcc   2880
tcgctgctcg agtggtcaag cagctgccag cttctttcaa ctacggagcc atcaaagccg   2940
atgctattca cgaactgctc gtgcgaatga agcgcgccga gctgtattgc cccaggccac   3000
tgctcgccat cgaggtgtcc agccaggaca gacataagca gaaaatcatt gccccagcta   3060
agcagctgct caactttgac ctgctcaaac tggccggaga tgtggaaagc aatcctgggc   3120
ccttcttttt cgccgacgtg aggtccaact tcagcaaact ggtcgacacc atcaatcaga   3180
tgcaggagga tatgtcaacc aagcacggcc ccgactttaa ccggctggtg tccgccttcg   3240
aggaactcgc taccggcgtg aaggccatca ggacaggact ggacgaggcc aaaccatggt   3300
acaagctgat caagctgctc tctcgcctct catgtatggc tgctgtggct gctcggagca   3360
aggaccccgt gctggtcgcc atcatgctcg ctgacaccgg cctggagatt ctcgattcta   3420
catttgtggt caagaaaatc tctgactcac tgtcttcact cttccacgtg ccagcccctg   3480
tcttttcctt cggagctcca attctgctcg ctggactggt gaaagtcgcc tccagctttt   3540
tccggtccac cccagaggac ctggaaaggg ccgagaagca gcgtcagaga cctctgaaag   3600
tgagagctaa gctcccacag caggaaggac cttacgctgg cccgttggag agacagaaac   3660
cgctgaaagt gaaagcaaaa gccccggtcg tcaaggaagg accttacgag ggaccggtga   3720
agaagcctgt cgctttgaaa gtgaaagcta agaacttgat agtcactgag agtggtgccc   3780
caccgaccga cttgcaaaag atggtcatgg gcaacacaaa gcctgttgag ctcatccttg   3840
acgggaagac agtagccatc tgttgtgcta ctggagtgtt tggcactgct tacctcgtgc   3900
ctcgtcatct tttcgcagag aagtatgaca agatcatgct ggatggcaga gccatgacag   3960
acagtgacta cagagtgttt gagtttgaga ttaaagtaaa aggacaggac atgctctcag   4020
acgctgcgct catggtgctc caccgtggga accgcgtgag agatatcacg aaacactttc   4080
gtgatacagc aagaatgaag aaaggcaccc ccgtcgtcgg tgtggtcaac aacgccgacg   4140
ttgggagact gattttctct ggtgaggccc tcacctacaa ggatattgta gtgaccatgg   4200
acggagacac catgcctggc ctctttgcct acaaagccgc caccaaggca ggctactgtg   4260
gaggagccgt tctcgccaag gacggggccg acactttcat cgtcggcact cactccgcag   4320
gaggcaatgg agttggatac tgctcatgcg tttccaggtc catgcttctc agaatgaagg   4380
cacacgttga ccctgaacca caacacgagt agtaggcggc cgctctagac tagctagaaa   4440
gatccgggaa cttgtttatt gcagcttata atggttacaa ataaagcaat agcatcacaa   4500
```

-continued

```
atttcacaaa taaagcattt ttttcactgc attctagttg tggtttgtcc aaactcatca   4560

atgtatctta tcatgtctg                                                4579
```

FMDV RECOMBINANT VACCINES AND USES THEREOF

CROSS-REFERENCE TO RELATED APPLICATIONS

This application claims priority to U.S. provisional application 62/054,073 filed on Sep. 23, 2014.

FIELD OF THE INVENTION

The present invention relates to compositions for combating Foot and Mouth Disease Virus (FMDV) infection in animals. The present invention provides pharmaceutical compositions comprising an FMDV antigen, methods of vaccination against FMDV, and kits for use with such methods and compositions.

BACKGROUND OF THE INVENTION

Foot-and-mouth disease (FMD) is one of the most virulent and contagious diseases affecting farm animals. This disease is endemic in numerous countries in the world, especially in Africa, Asia and South America. In addition, epidemic outbreaks can occur periodically. The presence of this disease in a country may have very severe economic consequences resulting from loss of productivity, loss of weight and milk production in infected herds, and from trade embargoes imposed on these countries. The measures taken against this disease consist of strict application of import restrictions, hygiene controls and quarantine, slaughtering sick animals and vaccination programs using inactivated vaccines, either as a preventive measure at the national or regional level, or periodically when an epidemic outbreak occurs.

FMD is characterized by its short incubation period, its highly contagious nature, the formation of ulcers in the mouth and on the feet and sometimes, the death of young animals. FMD affects a number of animal species, in particular cattle, pigs, sheep and goats. The agent responsible for this disease is a ribonucleic acid (RNA) virus belonging to the Aphthovirus genus of the Picornaviridae family (Cooper et al., Intervirology, 1978, 10, 165-180). At present, at least seven types of foot-and-mouth disease virus (FMDV) are known: the European types (A, O and C), the African types (SAT1, SAT2 and SAT3) and an Asiatic type (Asia 1). Numerous sub-types have also been distinguished (Kleid et al. Science (1981), 214, 1125-1129).

FMDV is a naked icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. Protein P1 is myristylated at its amino-terminal end. During the maturation process, protein P1 is cleaved by protease 3C into three proteins known as VP0, VP1 and VP3 (or 1AB, 1D and 1C respectively; Belsham G. J., Progress in Biophysics and Molecular Biology, 1993, 60, 241-261). In the virion, protein VP0 is then cleaved into two proteins, VP4 and VP2 (or 1A and 1B respectively). The mechanism for the conversion of proteins VP0 into VP4 and VP2, and for the formation of mature virions is not known. Proteins VP1, VP2 and VP3 have a molecular weight of about 26,000 Da, while protein VP4 is smaller at about 8,000 Da.

The simple combination of the capsid proteins forms the protomer or 5S molecule, which is the elementary constituent of the FMDV capsid. This protomer is then complexed into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 70S. The formation of empty capsids may occur naturally during viral replication or may be produced artificially by chemical treatment.

Some studies have been done on natural empty capsids. In particular, Rowlands et al. (Rowlands et al., J. Gen. Virol., 1975, 26, 227-238) have shown that the virions of A10 foot-and-mouth disease comprise mainly the four proteins VP1, VP2, VP3 and VP4. By comparison, the natural empty capsids (not obtained by recombination but purified from cultures of A10 foot-and-mouth virus) essentially contain the uncleaved protein VP0; identical results with the A-Pando foot-and-mouth virus are described by Rweyemamu (Rweyemamu et al., Archives of Virology, 1979, 59, 69-79). The artificial empty capsids, obtained after dialysis in the presence of Tris-EDTA and after centrifuging, contain no protein VP4. These artificial capsids are slightly immunogenic according to Rowlands et al., and the natural empty capsids are only immunogenic after treatment with formaldehyde to stabilize them, while the antibody response induced by the natural empty capsids in the guinea-pig is nevertheless inconstant, as noted by the author. Moreover, Rowlands et al. and Rweyemamu et al. do not agree on the need to stabilize the natural empty capsids. For Rweyemamu et al., the absence of treatment with formaldehyde is not prejudicial to the level of antigenicity of the natural empty capsids. The immunogenicity is only tested by the induction of neutralizing antibodies in the guinea-pig.

The expression of the gene coding for the precursor P1 of the capsid proteins by means of a recombinant baculovirus in insect cells is compared with the expression of the gene coding for P1 associated with the protease 3C in *E. coli* (Grubman et al., Vaccine, 1993, 11, 825-829; Lewis et al., J. Virol., 1991, 65, 6572-6580). The co-expression of P1 and 3C in *E. coli* results in the assembling of empty capsids 70S. The expression product of these two constructions produces neutralizing antibodies in guinea-pigs and pigs. The titers obtained with the P1/baculovirus construction are low. These same expression products induce partial protection in pigs. However, some pigs protected against the disease are not protected against the replication of the challenge virus. However, the *E. coli* expression system does not myristylate the proteins and the protease 3C is toxic to this cell. Lewis et al. conclude that fundamental questions relating to the make-up of the virus and the structure of the capsid needed to obtain maximum protection in the animal have not been answered. Furthermore, Grubman et al. state that it would be necessary to stabilize the empty capsids before formulating the vaccine; on this point they agree about the problems encountered with the empty capsids obtained by extraction from viral cultures (see above).

Fusion proteins containing some or all of protein P1 have also been obtained by the use of viral vectors, namely a herpes virus or vaccinia virus. CA-A-2,047,585 in particular describes a bovine herpes virus used to produce fusion proteins containing a peptide sequence of the foot-and-mouth virus (amino acids 141 to 158 of P1 bound to amino acids 200 to 213 of P1) fused with the glycoprotein gpIII of this bovine herpes virus. Viral vectors have also been used to express stabilized FMDV empty capsid (U.S. Pat. No.

7,531,182). Recently, plants have been investigated as a source for the production of FMDV antigens (US 2011/0236416).

Many hypotheses, research routes, and proposals have been developed in an attempt to design effective vaccines against FMD. Currently, the only vaccines on the market contain inactivated virus. Concerns about safety of the FMDV vaccine exist, as outbreaks of FMD in Europe have been associated with shortcomings in vaccine manufacture (King, A. M. Q. et al., 1981, Nature 293: 479-480). The inactivated vaccines do not confer long-term immunity, thus requiring booster injections given every year, or more often in the event of epidemic outbreaks. In addition, there are risks linked to incomplete inactivation and/or to the escape of virus during the production of inactivated vaccines (King, A. M. Q., ibid). A goal in the art has been to construct conformationally correct immunogens lacking the infective FMDV genome to make effective and safe vaccines.

It has been reported that maternally derived antibodies (MDA) are able to inhibit calves' (under 2 years of age cattle) response to vaccination against FMD (Graves, 1963, Journal of Immunology 91:251-256; Brun et al., 1977, Developments in Biological Standardisation, 25:117-122).

Considering the susceptibility of animals (including humans, albeit rarely), to FMDV, a method of preventing FMDV infection and protecting animals is essential. Accordingly, there is a need for more effective and stable vaccines against FMDV.

SUMMARY OF THE INVENTION

Compositions or vaccines comprising an antigenic FMDV polypeptide and fragments and variants thereof and compositions or vaccines comprising recombinant viral vectors expressing FMDV polypeptide and fragments and variants thereof are provided. The FMDV antigens and fragments and variants thereof possess immunogenic and protective properties. The FMDV antigens may be produced by a baculovirus expression vector in insect cells. The FMDV antigens may be modified to enhance the stability of FMDV empty capsids or FMDV VLPs (virus-like particles). The recombinant viral vectors may be adenovirus vectors expressing FMDV antigens.

The antigenic polypeptides and fragments and variants thereof or recombinant viral vectors can be formulated into vaccines and/or pharmaceutical compositions. Such vaccines or compositions can be used to vaccinate an animal and provide protection against homologous and heterologous FMDV strains.

Methods for enhanced protection in conventional animals and maternally derived antibody-positive (MDA-positive) animals against FMDV infections are provided. Kits comprising at least one antigenic polypeptide or fragment or variant thereof and instructions for use are also provided.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts a table summarizing the DNA and Protein sequences.

FIG. 4 depicts the result of electronic microscopy of MacMEB097.

FIGS. 6, 6A and 6B depict the electronic microscopy and specific ELISA of BacMEB099.

FIGS. 7A, 7B, 7C and 7D depict the sequence alignments of the protein sequences.

FIG. 10 depicts the FMDV A24 Cruzeiro neutralizing antibody titers.

FIGS. 12A, 12B and 12C depict the evolution of mean rectal temperature after challenge.

FIG. 13 depicts the EM analysis of A24 Cruzeiro VLPs with or without covalent cage mutation in the presence or absence of heat or acid.

FIG. 14 depicts the ELISA analysis of VLPs with or without the covalent cage mutation for the A24 Cruzeiro serotype after heating.

FIG. 17 depicts the ELISA results showing O1 Manisa covalent cage VLP stability in acid (above) and heat (below).

FIG. 19B depicts the Asia Shamir covalent cage & Iraq A22 covalent cage VLP serology data.

DETAILED DESCRIPTION

Figure 2:
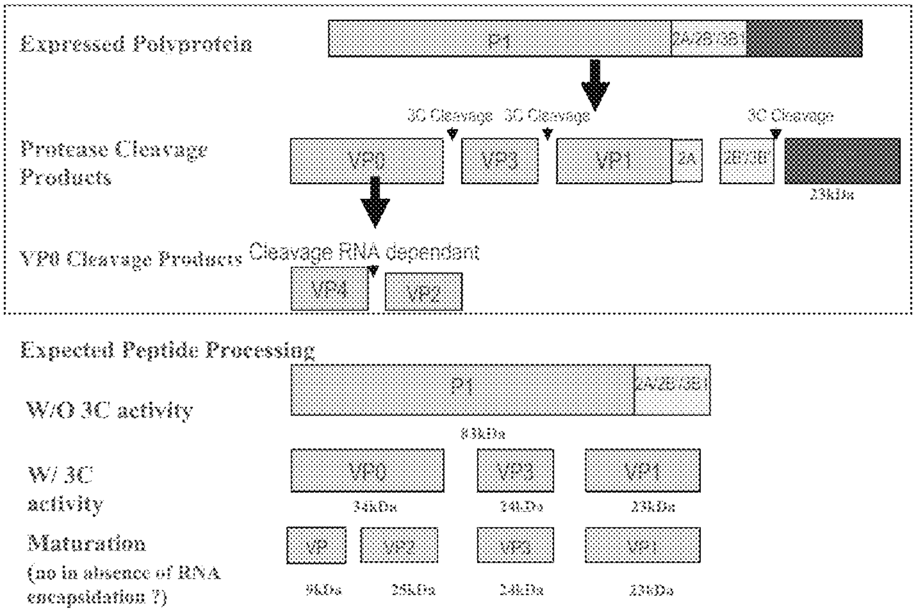
FIG. 2 represents the expressed FMDV polyprotein and the process by 3C.

Compositions comprising an FMDV polypeptide, antigen and fragments and variants thereof and compositions comprising recombinant viral vectors expressing FMDV antigens that elicit an immunogenic response in an animal are provided. The antigenic polypeptides or fragments or variants thereof are produced by a baculovirus expression vector in insect cells. The recombinant viral vectors may be adenovirus vectors expressing FMDV antigens. The antigenic polypeptides or fragments or variants or recombinant viral vectors expressing the antigens may be formulated into vaccines or pharmaceutical compositions and used to elicit or stimulate a protective response in an animal. In one embodiment the polypeptide antigen is an FMDV P1, VP2 or 3C polypeptide or active fragment or variant thereof. The FMDV antigens may be modified to enhance the stability of FMDV empty capsids or FMDV VLPs (virus-like particles).

It is recognized that the antigenic polypeptides of the invention may be full length polypeptides or active fragments or variants thereof. By "active fragments" or "active variants" is intended that the fragments or variants retain the antigenic nature of the polypeptide. Thus, the present invention encompasses any FMDV polypeptide, antigen, epitope or immunogen that elicits an immunogenic response in an animal. The FMDV polypeptide, antigen, epitope or immunogen may be any FMDV polypeptide, antigen, epitope or immunogen, such as, but not limited to, a protein, peptide or fragment or variant thereof, that elicits, induces or stimulates a response in an animal, such as an ovine, bovine, caprine or porcine.

Particular FMDV antigenic polypeptides include P1, VP2 and 3C. FMDV is a non-enveloped icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. Protein Pis myristylated at its amino-terminal end. During the maturation process, protein P1 is cleaved by the protease 3C into three proteins known as VP0, VP1 and VP3 (or 1AB, 1D and 1C respectively; Belsham G. J., Progress in Biophysics and Molecular Biology, 1993, 60, 241-261). In the virion, protein VP0 is then cleaved into two proteins, VP4 and VP2 (or 1A and 1B respectively). Proteins VP1, VP2 and VP3 have a molecular weight of about 26,000 Da, while protein VP4 is smaller at about 8,000 Da. FMDV sequences are also described in U.S. Pat. Nos. 7,527,960 and 7,531,182, which documents are herein incorporated in their entirety.

The simple combination of the capsid proteins forms the protomer or 5S molecule, which is the elementary constituent of the FMDV capsid. This protomer is then complexed into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 70S. The formation of empty capsids may occur naturally during viral replication or may be produced artificially by chemical treatment.

The present invention relates to bovine, ovine, caprine, or swine vaccines or compositions which may comprise an effective amount of a recombinant FMDV antigen or a recombinant viral vector expressing FMDV antigen, and a pharmaceutically or veterinarily acceptable carrier, excipient, adjuvant, or vehicle.

In some embodiments, the vaccines further comprise adjuvants, such as the oil-in-water (O/W) emulsions described in U.S. Pat. No. 7,371,395.

In still other embodiments, the adjuvants include EMULSIGEN, Aluminum Hydroxide, Saponin, and CpG, or combinations thereof.

In some embodiments, the response in the animal is a protective immune response.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle, cow), swine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The antigenic polypeptides of the invention are capable of protecting against FMDV. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein, polypeptide, or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984, PNAS USA, 81(13): 3998-400; Geysen et al., 1985, PNAS USA, 82(1): 178-82. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed the invention encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of an FMDV polypeptide. A polynucleotide encoding a fragment of an FMDV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding an FMDV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. That is the polypeptide is separated from cellular components. By "substantially purified" it is intended that such that the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are FMDV antigenic polypeptides that are produced by a baculovirus expression vector in insect cells in vitro or by a viral vector in vivo. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

In one aspect, the present invention provides FMDV polypeptides from ovine, bovine, caprine, or swine FMDV isolates. In another aspect, the present invention provides a polypeptide having a sequence as set forth in SEQ ID NOs: 1, 2, 4, 5, 6, 8, 10, 12, 13 or 16 and variant or fragment thereof.

In another aspect, the invention relates to improving the temperature and/or acid stability of FMDV empty capsids or FMDV VLPs (virus-like particles). The temperature and/or acid stability of the empty capsids is advantageously ensured by the formation of disulfide bridges.

In particular, this improvement is obtained by replacing an amino acid of the original sequence with cysteine in the polypeptide sequence of a structural protein of the capsid, protein VP2 (derived from P1), for example, at position 179 of the amino acid sequence SEQ ID NO: 2, 4, 6, 8, 10, or 16 (P1 of FMDV A24 strain, FMDV O1 manisa strain, FMDV Iraq strain, or FMDV Asia strain). As a general rule, the position of this amino acid is identical in VP2 protein derived from other foot-and-mouth viruses (as is the case particularly with the strains described in the examples). The region containing this amino acid corresponds to an alpha helix. To identify or confirm the amino acid which is to be mutated, the amino acid sequences of this region are aligned with the corresponding region (for example of the order of about ten or slightly more—e.g. 10 to 20-amino acids) on the sequence SEQ ID NO: 2, 4, 6, 8, 10, or 16 taking into account of the fact that the sequences are well conserved in structure among the different FMDV. The amino acid to mutate is located at position 179 of the FMDV P1 (SEQ ID NO: 2, 4, 6, 8, 10, or 16). By convention, the methionine corresponding to the initiation codon (which is not present in the natural sequence and is therefore added) is numbered 1.

Moreover, homologs of FMDV polypeptides from ovine, bovine, caprine, or swine are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type FMDV polypeptide can differ from the wild-type FMDV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type FMDV polypepetide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the FMDV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for FMDV polypeptides, the DNA sequence of the FMDV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of FMDV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the FMDV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm. The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the FMDV polynucleotides contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to ovine, bovine, caprine and swine vaccines or pharmaceutical or immunological compositions which may comprise an effective amount of a recombinant FMDV antigens and a pharmaceutically or veterinarily acceptable carrier, adjuvant, excipient, or vehicle.

The subject matter described herein is directed in part, to compositions and methods related to the FMDV antigen prepared in a baculovirus/insect cell expression system that is highly immunogenic and protects animals against challenge from homologous and heterologous FMDV strains.

Compositions

The present invention relates to an FMDV vaccine or composition which may comprise an effective amount of a recombinant FMDV antigen and a pharmaceutically or veterinarily acceptable carrier, excipient, adjuvant, or vehicle. In one embodiment, the recombinant FMDV antigen is expressed by a baculovirus expression vector in insect cells. In another embodiment, the FMDV vaccine or composition comprises a recombinant viral vector expressing FMDV antigens.

One embodiment of the invention relates to a vaccine or composition comprising FMDV empty capsids. In another embodiment, the invention relates to a vaccine or composition comprising a viral vector expressing FMDV empty capsids. The FMDV empty capsids are obtained by expression of the cDNA of regions P1, 2A/2B'/3B' and 3C. The FMDV empty capsids or FMDV VLPs (virus-like particles) may be modified with enhanced heat and/or acid (low PH) stability.

The present invention relates to vaccines against foot-and-mouth disease and in particular to improving their heat and/or acid (low PH) stability. It also relates to processes for preparing these vaccines, the use of antigens for producing these vaccines and vaccination methods using them.

The present invention also relates to nucleotide sequences, in particular cDNA, and to amino acid sequences, modified compared with natural sequences of the virus. The invention also relates to the expression products of the modified nucleotide sequences and to the FMDV antigens and virus incorporating these modifications.

The present invention encompasses any FMDV polypeptide, antigen, epitope or immunogen that elicits an immunogenic response in an animal, such as an ovine, bovine, caprine or swine. The FMDV polypeptide, antigen, epitope or immunogen may be any FMDV polypeptide, antigen, epitope or immunogen, such as, but not limited to, a protein, peptide or fragment thereof, that elicits, induces or stimulates a response in an animal, such as an ovine, bovine, caprine or swine.

In an embodiment wherein the FMDV immunological composition or vaccine is a recombinant immunological composition or vaccine, the composition or vaccine comprises a recombinant vector and a pharmaceutical or veterinary acceptable excipient, carrier, adjuvant or vehicle; the recombinant vector is a baculovirus expression vector which may comprise a polynucleotide encoding an FMDV polypeptide, antigen, epitope or immunogen. The FMDV polypeptide, antigen, epitope or immunogen, may be VP1, VP2, VP3, VP4, VP5, NS1, VP7, NS2, VP6, NS3, NS3a, P1, VP0, 3C, or any fragment thereof.

In another embodiment, the FMDV antigen is P1, VP0, VP3, VP1, VP2, VP4, 2A, 2B, or 3C.

In one embodiment, the nucleic acid molecule encoding one or more FMDV antigen(s) is a cDNA encoding FMDV P1 region and a cDNA encoding FMDV 3C protease of FMDV.

In one embodiment, the FMDV antigen may be a P1-3C polypeptide. In another embodiment, the FMDV antigen may be P1 alone, or P1-2A/2B1. In yet another embodiment, the FMDV antigen may be VP0-VP3. In another embodiment, the FMDV antigen may be VP4-VP2. In still another embodiment, the FMDV antigen may be 3C, or may be 3C with a 5'UTR optimized for expression in insect cells. In one embodiment, both P1-2A/2B1 and 3C polypeptides may be expressed in insect cells using a single construct and the expression may be regulated by one or more promoter sequences. In another embodiment, the FMDV antigen is a modified P1 or VP2.

In another embodiment, the FMDV antigen may be derived from FMDV O1 Manisa, O1 BFS or Campos, A24 Cruzeiro, Asia 1 Shamir, A Iran '96, A22 Iraq, SAT2 Saudi Arabia.

The present invention relates to an FMDV vaccine which may comprise an effective amount of a recombinant FMDV antigen or a recombinant viral vector expressing an FMDV antigen, and a pharmaceutically or veterinarily acceptable carrier, excipient, adjuvant, or vehicle.

In another embodiment, pharmaceutically or veterinarily acceptable carrier, excipient, adjuvant, or vehicle may be a water-in-oil emulsion. In yet another embodiment, the water-in-oil emulsion may be an oil-in-water emulsion.

The invention further encompasses the FMDV polynucleotides contained in a vector molecule or an expression vector and operably linked to a promoter element and optionally to an enhancer.

In one aspect, the present invention provides FMDV polypeptides, particularly ovine, bovine, caprine or swine polypeptides having a sequence as set forth in SEQ ID NO:1, 2, 4, 5, 6, 8, 10, 12, 13, or 16 and variants or fragments thereof.

In another aspect, the present invention provides a polypeptide having at least 70%, at least 75%, at least 80%, at least 85%, at least 90%, at least 95%, 96%, 97%, 98% or 99% sequence identity to an antigenic polypeptide of the invention, particularly to the polypeptides having a sequence as set forth in SEQ ID NO: 1, 2, 4, 5, 6, 8, 10, 12, 13, or 16.

In yet another aspect, the present invention provides fragments and variants of the FMDV polypeptides identified above (SEQ ID NO: 1, 2, 4, 5, 6, 8, 10, 12, 13, or 16) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 1, 2, 4, 5, 6, 8, 10, 12, 13, or 16.

An immunogenic fragment of an FMDV polypeptide includes at least 8, 10, 15, or 20 consecutive amino acids, at least 21 amino acids, at least 23 amino acids, at least 25 amino acids, or at least 30 amino acids of an FMDV polypeptide having a sequence as set forth in SEQ ID NO: 1, 2, 4, 5, 6, 8, 10, 12, 13, or 16, or variants thereof. In another embodiment, a fragment of an FMDV polypeptide includes a specific antigenic epitope found on a full-length FMDV polypeptide.

In another aspect, the present invention provides a polynucleotide encoding an FMDV polypeptide, such as a polynucleotide encoding a polypeptide having a sequence as set forth in SEQ ID NO: 1, 2, 4, 5, 6, 8, 10, 12, 13, or 16. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 2, 4, 5, 6, 8, 10, 12, 13, or 16, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO:3, 7, 9, 11, 14, 15, 17, 18, 19, or 20, or a variant thereof. In yet another aspect, the present invention provides a polynucleotide having at least 70%, at least 75%, at least 80%, at least 85%, at least 90%, at least 95%, at least 95%, 96%, 97%, 98%, or 99% sequence identity to one of a polynucleotide having a sequence as set forth in SEQ ID NO: 3, 7, 9, 11, 14, 15, 17, 18, 19, or 20, or a variant thereof.

The polynucleotides of the invention may comprise additional sequences, such as additional encoding sequences within the same transcription unit, controlling elements such as promoters, ribosome binding sites, enhancer, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an FMDV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an FMDV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more FMDV polypeptides, antigens, epitopes or immunogens. In one embodiment, the vector contains and expresses a polynucleotide that comprises, consists essentially of, or consists of a polynucleotide coding for (and advantageously expressing) an FMDV antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an FMDV polypeptide, antigen, epitope or immunogen, or a fragment thereof.

According to another embodiment, the vector or vectors in the preparation comprise, or consist essentially of, or consist of polynucleotide(s) encoding one or more proteins or fragment(s) thereof of an FMDV polypeptide, antigen, epitope or immunogen, the vector or vectors expressing the polynucleotide(s). In another embodiment, the preparation comprises one, two, or more vectors comprising polynucleotides encoding and expressing, advantageously in vivo, an FMDV polypeptide, antigen, fusion protein or an epitope thereof. The invention is also directed at mixtures of vectors that comprise polynucleotides encoding and expressing different FMDV polypeptides, antigens, epitopes or immunogens, e.g., an FMDV polypeptide, antigen, epitope or immunogen from different animal species such as, but not limited to, ovine, bovine, caprine or swine.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke et al., 1997; Hartikka et al., 1996, Hum Gene Ther, 7(10): 1205-17; see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF 1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an FMDV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995.). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985, Cell, 41(2): 521-30) or murine CMV-IE.

In more general terms, the promoter has either a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000, Vaccine, 18(22): 2337-44), or the actin promoter (Miyazaki et al., 1989, Gene, 79(2): 269-77).

The plasmids may comprise other expression control elements. It is particularly advantageous to incorporate stabilizing sequence(s), e.g., intron sequence(s), for example, maize alcohol dehydrogenase intron (Callis et al. Genes & Dev.1(10):1183-1200, December 1987), the first intron of the hCMV-IE (PCT Application No. WO1989/01036), the intron II of the rabbit β-globin gene (van Ooyen et al., 1979, Science, 206(4416): 337-44). In another embodiment, the plasmids may comprise 3' UTR. The 3' UTR may be, but not limited to, *agrobacterium* nopaline synthase (Nos) 3' UTR (Nopaline synthase: transcript mapping and DNA sequence. Depicker, A. et al. J. Mol. Appl. Genet., 1982; Bevan, N A R, 1984, 12(22): 8711-8721).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. In one embodiment, the recombinant FMDV antigen is expressed in insect cells.

Methods of Use

In an embodiment, the subject matter disclosed herein is directed to a method of vaccinating an ovine, bovine, caprine, or swine comprising administering to the ovine, bovine, caprine, or swine an effective amount of a vaccine which may comprise an effective amount of a recombinant FMDV antigen or a recombinant viral vector expressing an FMDV antigen, and a pharmaceutically or veterinarily acceptable carrier, excipient, adjuvant, or vehicle.

In one embodiment of the present invention, the method comprises a single administration of a vaccine composition formulated with an emulsion according to the invention. For example, in one embodiment, the immunological or vaccine composition comprises baculovirus expressed FMDV antigens, including polypeptides and VLPs (virus-like particles) or empty capsids, or a recombinant viral vector expressing an FMDV antigen. Electron microscopy indicates the insect cells transformed with baculovirus expression vectors produce FMDV VLPs or FMDV empty capsids, and so immunological or vaccine compositions according to the instant invention encompass those comprising FMDV VLPs or FMDV empty capsids.

In another embodiment of the present invention, the method comprises a single administration of two heterologous vaccine compositions. The heterologous vaccines or compositions may be different types of vaccines, such as FMDV VLPs vaccine or FMDV viral vector vaccines. The heterologous vaccines may also be the same type of vaccines expressing the capsids of different FMDV serotypes, such as A24, O1 Manisa, Asia or Iraq strains.

In an embodiment, the subject matter disclosed herein is directed to a method of vaccinating an ovine, bovine, caprine, or swine comprising administering to the ovine, bovine, caprine, or swine the FMDV antigen produced by a baculovirus vector in insect cells or a recombinant viral vector expressing an FMDV antigen In an embodiment, the subject matter disclosed herein is directed to a method of eliciting an immune response comprising administering to the ovine, bovine, caprine, or swine a vaccine comprising the FMDV antigen produced by a baculovirus vector in insect cells or a recombinant viral vector expressing an FMDV antigen.

In an embodiment, the subject matter disclosed herein is directed to a method of preparing a vaccine or composition comprising isolating an FMDV antigen produced by a baculovirus vector in insect cells or a recombinant viral vector expressing an FMDV antigen and optionally combining with a pharmaceutically or veterinarily acceptable carrier, excipient, adjuvant, or vehicle.

Both homologous and heterologous FMDV strains are used for challenge to test the efficacy of the vaccine. The administering may be subcutaneously or intramuscularly. The administering may be needle free (for example Pigjet or Bioject).

In one embodiment of the invention, a prime-boost regimen can be employed, which is comprised of at least one primary administration and at least one booster administration using at least one common polypeptide, antigen, epitope or immunogen. The immunological composition or vaccine used in primary administration is different in nature from those used as a booster. However, it is noted that the same composition can be used as the primary administration and the boost. This administration protocol is called "prime-boost".

A prime-boost according to the present invention can include a recombinant viral vector that is used to express an FMDV coding sequence or fragments thereof encoding an antigenic polypeptide or fragment or variant thereof. Specifically, the viral vector can express an FMDV gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. Nos. 5,505,941, 5,494,8070), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The FMDV antigen of the invention to be expressed is inserted under the control of a specific poxvirus promoter, e.g., the entomopoxvirus *Amsacta moorei* 42K promoter (Barcena, Lorenzo et al., 2000, J Gen Virol., 81(4): 1073-85), the vaccinia promoter 7.5 kDa (Cochran et al., 1985, J Virol, 54(1): 30-7), the vaccinia promoter I3L (Riviere et al., 1992, J Virol, 66(6): 3424-34), the vaccinia promoter HA (Shida, 1986, Virology, 150(2): 451-62), the cowpox promoter ATI (Funahashi et al., 1988, J Gen Virol, 69 (1): 35-47), the vaccinia promoter H6 (Taylor et al., 1988, Vaccine, 6(6): 504-8; Guo et al., 1989, J Virol, 63(10): 4189-98; Perkus et al., 1989, J Virol, 63(9): 3829-36.), inter alia.

In another embodiment, the avipox expression vector may be a canarypox vector, such as, ALVAC. The FMDV antigen, epitope or immunogen may be FMDV P1-3C. The FMDV viral vector may be a canarypox virus such as vCP2186, vCP2181, or vCP2176, or a fowlpox virus such as vFP2215 (see U.S. Pat. No. 7,527,960). In yet another embodiment, the FMDV antigen, epitope or immunogen may be produced in duckweed (US 2011/0236416).

In another aspect of the prime-boost protocol of the invention, a composition comprising the FMDV antigen of the invention is administered followed by the administration of vaccine or composition comprising a recombinant viral vector that contains and expresses the FMDV antigen in vivo, or an inactivated viral vaccine or composition comprising the FMDV antigen, or a DNA plasmid vaccine or composition that contains or expresses the FMDV antigen. Likewise, a prime-boost protocol may comprise the administration of vaccine or composition comprising a recombinant viral vector that contains and expresses an FMDV antigen in vivo, or an inactivated viral vaccine or composition comprising an FMDV antigen, or a DNA plasmid vaccine or composition that contains or expresses an FMDV antigen, followed by the administration of a composition comprising the FMDV antigen of the invention. It is further noted that both the primary and the secondary administrations may comprise the composition comprising the FMDV antigen of the invention.

A prime-boost protocol comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of ovine, bovine, caprine or swine compositions, based on viral vectors, e.g., non-poxvirus-viral-vector-based compositions, is generally between about 0.1 to about 5.0 ml, between about 0.1 to about 3.0 ml, and between about 0.5 ml to about 2.5 ml.

The efficacy of the vaccines may be tested about 2 to 4 weeks after the last immunization by challenging animals, such as ovine, bovine, caprine or swine, with a virulent strain of FMDV, advantageously the FMDV O1 Manisa, O1 BFS or Campos, A24 Cruzeiro, Asia 1 Shamir, A Iran '96, A22 Iraq, SAT2 Saudi Arabia strains.

Still other strains may include FMDV strains A10-61, A5, A12, A24/Cruzeiro, C3/Indaial, O1, C1-Santa Pau, C1-C5, A22/550/Azerbaijan/65, SAT1-SAT3, A, A/TNC/71/94, A/IND/2/68, A/IND/3/77, A/IND/5/68, A/IND/7/82, A/IND/16/82, A/IND/17/77, A/IND/17/82, A/IND/19/76, A/IND/20/82, A/IND/22/82, A/IND/25/81, A/IND/26/82, A/IND/54/79, A/IND/57/79, A/IND/73/79, A/IND/85/79, A/IND/86/79, A/APA/25/84, A/APN/41/84, A/APS/44/05, A/APS/50/05, A/APS/55/05, A/APS/66/05, A/APS/68/05, A/BIM/46/95, A/GUM/33/84, A/ORS/66/84, A/ORS/75/88, A/TNAn/60/947/Asia/1, A/IRN/05, Asia/IRN/05, 0/HK/2001, 0/UKG/3952/2001, O/UKG/4141/2001, Asia 1/HNK/CHA/05 (GenBank accession number EF149010, herein incorporated by reference), Asia I/XJ (Li, ZhiYong et al. Chin Sci Bull, 2007), HK/70 (Chin Sci Bull, 2006, 51(17): 2072-2078), 0/UKG/7039/2001, 0/UKG/9161/2001, O/UKG/7299/2001, 0/UKG/4014/2001, 0/UKG/4998/2001, 0/UKG/9443/2001, 0/UKG/5470/2001, 0/UKG/5681/2001, 0/ES/2001, HKN/2002, O5India, 0/BKF/2/92, K/37/84/A, KEN/1/76/A, GAM/51/98/A, A10/Holland, O/KEN/1/91, O/IND49/97, O/IND65/98, O/IND64/98, O/IND48/98, O/IND47/98, O/IND82/97, O/IND81/99, O/IND81/98, O/IND79/97, O/IND78/97, O/IND75/97, O/IND74/97, O/IND70/97, O/IND66/98, O/IND63/97, O/IND61/97, O/IND57/98, O/IND56/98, O/IND55/98, O/IND54/98, O/IND469/98, O/IND465/97, O/IND464/97, O/IND424/97, O/IND423/97, O/IND420/97, O/IND414/97, O/IND411/97, O/IND410/97, O/IND409/97, O/IND407/97, O/IND399/97, O/IND39/97, O/IND391/97, O/IND38/97, O/IND384/97, O/IND380/97, O/IND37/97, O/IND352/97, O/IND33/97, O/IND31/97, O/IND296/97, O/IND23/99, O/IND463/97, O/IND461/97, O/IND427/98, O/IND28/97, O/IND287/99, O/IND285/99, O/IND282/99, O/IND281/97, O/IND27/97, O/IND278/97, O/IND256/99, O/IND249/99, O/IND210/99, O/IND208/99, O/IND207/99, O/IND205/99, O/IND185/99, O/IND175/99, O/IND170/97, O/IND164/99, O/IND160/99, O/IND153/99, O/IND148/99, O/IND146/99, O/SKR/2000, A22/India/17/77.

Further details of these FMDV strains may be found on the European Bioinformatics Information (EMBL-EBI) web pages, and all of the associated nucleotide sequences are herein incorporated by reference. The inventors contemplate that all FMDV strains, both herein listed, and those yet to be identified, could be expressed according to the teachings of the present disclosure to produce, for example, effective vaccine compositions. Both homologous and heterologous strains are used for challenge to test the efficacy of the vaccines. The animal may be challenged intradermally, subcutaneously, spray, intra-nasally, intra-ocularly, intra-tracheally, and/or orally.

The prime-boost administrations may be advantageously carried out 1 to 6 weeks apart, for example, about 3 weeks apart. According to one embodiment, a semi-annual booster or an annual booster, advantageously using the viral vector-based vaccine, is also envisaged. The animals are advantageously at least 6 to 8 weeks old at the time of the first administration.

The compositions comprising the recombinant antigenic polypeptides of the invention used in the prime-boost protocols are contained in a pharmaceutically or veterinary acceptable vehicle, diluent, adjuvant, or excipient. The protocols of the invention protect the animal from ovine, bovine, caprine or porcine FMDV and/or prevent disease progression in an infected animal.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetj et or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

In one embodiment, the invention provides for the administration of a therapeutically effective amount of a formulation for the delivery and expression of an FMDV antigen or epitope in a target cell. Determination of the therapeutically effective amount is routine experimentation for one of ordinary skill in the art. In one embodiment, the formulation comprises an expression vector comprising a polynucleotide that expresses an FMDV antigen or epitope and a pharmaceutically or veterinarily acceptable carrier, vehicle or excipient. In another embodiment, the pharmaceutically or veterinarily acceptable carrier, vehicle or excipient facilitates transfection or other means of transfer of polynucleotides to a host animal and/or improves preservation of the vector or protein in a host.

In one embodiment, the subject matter disclosed herein provides a detection method for differentiation between infected and vaccinated animals (DIVA).

It is disclosed herein that the use of the vaccine or composition of the present invention allows the detection of FMDV infection in an animal. It is disclosed herein that the use of the vaccine or composition of the present invention allows the detection of the infection in animals by differentiating between infected and vaccinated animals (DIVA). A method is disclosed herein for diagnosing the infection of FMDV in an animal using an FMDV non-structural protein (e.g. a FMDV 3ABC or 3D-specific ELISA).

Article of Manufacture

In an embodiment, the subject matter disclosed herein is directed to a kit for performing a method of eliciting or inducing an immune response which may comprise any one of the recombinant FMDV immunological compositions or vaccines, or inactivated FMDV immunological compositions or vaccines, recombinant FMDV viral compositions or vaccines, and instructions for performing the method.

Another embodiment of the invention is a kit for performing a method of inducing an immunological or protective response against FMDV in an animal comprising a composition or vaccine comprising an FMDV antigen of the invention and a recombinant FMDV viral immunological composition or vaccine, and instructions for performing the method of delivery in an effective amount for eliciting an immune response in the animal.

Another embodiment of the invention is a kit for performing a method of inducing an immunological or protective response against FMDV in an animal comprising a composition or vaccine comprising an FMDV antigen of the invention and an inactivated FMDV immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The following embodiments are encompassed by the invention. In an embodiment, a composition comprising an FMDV antigen or fragment or variant thereof and a pharmaceutically or veterinarily acceptable carrier, excipient, adjuvant, or vehicle is disclosed. In another embodiment, a composition comprising a recombinant viral vector expressing FMDV antigens and a pharmaceutically or veterinarily acceptable carrier, excipient, adjuvant, or vehicle is disclosed. In another embodiment, the composition described above wherein the FMDV antigen or fragment or variant thereof comprises an immunogenic fragment comprising at least 15 amino acids of an ovine, bovine, caprine, or swine FMDV antigen is disclosed. In an embodiment, the above compositions wherein the FMDV antigen or fragment or variant thereof is partially purified are disclosed. In an embodiment, the above compositions wherein the FMDV antigen or fragment or variant thereof is substantially purified are disclosed.

In an embodiment, the above compositions wherein the FMDV antigen or fragment or variant thereof is an ovine, bovine, caprine, or swine FMDV polypeptide are disclosed. In an embodiment, the above compositions wherein the FMDV polypeptide is a P1-3C polypeptide, P1 polypeptide, VP0 polypeptide, VP1 polypeptide, VP3 polypeptide, VP2 polypeptide, VP4 polypeptide, 2A polypeptide, 2B1 polypeptide, or 3C polypeptide are disclosed. In an embodiment, the above compositions wherein the FMDV antigen or fragment or variant thereof has at least 80% sequence identity to the sequence as set forth in SEQ ID NO:1, 2, 4, 5, 6, 8, 10, 12, 13 or 16 are disclosed. In one embodiment, the above compositions wherein the FMDV antigen is encoded by a polynucleotide having at least 70% sequence identity to the sequence as set forth in SEQ ID NO:3, 7, 9, 11, 14, 15, 17, 18, 19 or 20 are disclosed. In an embodiment, the above compositions wherein the pharmaceutically or veterinarily acceptable carrier, excipient, adjuvant, or vehicle is a water-in-oil emulsion or an oil-in-water emulsion are disclosed. In another embodiment, a method of vaccinating an animal susceptible to ovine, bovine, caprine, or swine FMDV comprising administering the compositions above to the animal is disclosed. In an embodiment, a method of vaccinating an animal susceptible to ovine, bovine, caprine, or swine FMDV comprising a prime-boost regimen is disclosed. In an embodiment, a substantially purified antigenic polypeptide expressed in insect cells, wherein the polypeptide comprises: an amino acid sequence having at least 80% sequence identity to a polypeptide having the sequence as set forth in SEQ ID NO: 1, 2, 4, 5, 6, 8 10, 12, 13, or 16 is disclosed. In any embodiment the animal is preferably an ovine, a bovine, a swine, or a caprine. In one embodiment, a method of diagnosing FMDV infection in an animal is disclosed. In yet another embodiment, a kit for prime-boost vaccination comprising at least two vials, wherein a first vial containing the composition comprising an FMDV antigen or fragment or variant thereof, and a second vial containing a recombinant viral vector that contains or expresses the FMDV antigen is disclosed.

The pharmaceutically or veterinarily acceptable carriers or vehicles or adjuvants or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or adjuvants or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

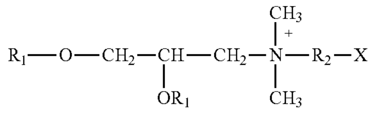

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and about 1:about 1 and about 1:about 2, e.g., 1:1 and 1:2.

In another embodiment, pharmaceutically or veterinarily acceptable carrier, excipient, adjuvant, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084, e.g., Example 8 thereof, incorporated herein by reference. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996, PNAS USA, 93(7): 2879-83; WO98/16247), (3) an oil in water emulsion, such as the SPT emulsion described on page 147 of "Vaccine Design, The Subunit and Adjuvant Approach" published by M. Powell, M. Newman, Plenum Press 1995, 6: 147, 183, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are Preferably formed by basic units having the following formula:

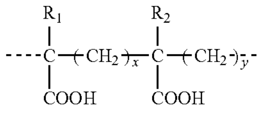

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), polyinosinic and polycytidylic acid, cytidine-phosphate-guanosine oligodeoxynucleotides (CpG ODN), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a bovine cytokine for preparations to be administered to bovines).

In a particular embodiment, the adjuvant may include TS6, TS7, TS8 and TS9 emulsions (U.S. Pat. No. 7,371,395); LR3 and LR4 (U.S. Pat. No. 7,691,368); TSAP (US20110129494); TRIGEN™ (Newport Labs); synthetic dsRNAs (e.g. poly-IC, poly-ICLC [HILTONOL®]); and MONTANIDE™ adjuvants (W/O, W/O/W, O/W, IMS and Gel; all produced by SEPPIC).

In the case of immunological composition and/or vaccine based on a baculovirus/insect cell-expressed polypeptides, a dose may include, about 1 μg to about 2000 μg, about 50 μg to about 1000 μg, and from about 100 μg to about 500 μg of FMDV antigen, epitope or immunogen. The dose may include about $10^2$ to about $10^{20}$, about $10^3$ to about $10^{18}$, about $10^4$ to about $10^{16}$, about $10^5$ to about $10^{12}$ VLPs. In the case of immunological composition and/or vaccine based on a viral vector expressing FMDV antigens, a dose may include, about $10^3$ $TCID_{50}$ to about $10^{15}$ $TCID_{50}$ (50% Tissue Culture Infective Dose), about $10^3$ $TCID_{50}$ to about $10^{14}$ $TCID_{50}$, about $10^3$ $TCID_{50}$ to about $10^{13}$ $TCID_{50}$, about $10^3$ $TCID_{50}$ to about $10^{12}$ $TCID_{50}$. The dose volumes can be between about 0.1 and about 10 ml, advantageously between about 0.2 and about 5 ml.

The invention will now be further described by way of the following non-limiting examples.

EXAMPLES

Construction of DNA inserts, plasmids and recombinant viral or baculovirus vectors was carried out using the standard molecular biology techniques described by J. Sambrook et al. (Molecular Cloning: A Laboratory Manual, 2nd Edition, Cold Spring Harbor Laboratory, Cold Spring Harbor, N. Y., 1989).

Example 1

Construction and Expression of FMDV Antigens in Baculovirus/Insect Cells System The positive strain RNA genome of serotype A FMDV is composed of a single ORF (1662 amino acids) flanked by two non-coding regions. The ORF holds 3 parts. The first part is Polyprotein P1-2A that leads to the expression of 4 capsids components (VP4, VP2, VP3 and VP1) after maturation and cleavage. The second part is P2 containing 2 proteins (2B and 2C) and is involved in RNA synthesis and cell membrane vesicle proliferation. The first part is P3 containing 4 proteins (3A, 3B, 3C and 3D). 3C is the major one involved in the cleavage of the polyprotein. 3D is another protease and 3A/3B are involved in the membrane anchorage, pathogenesis, RNA synthesis and encapsidation. P1-2A and 3C are necessary for expression and cleavage of all the proteins making up the FMDV capsid particles or FMDV VLPs (see FIG. 2). Potential functional domains are shown in table 1 below.

TABLE 1

| Potential functional domains annotated on GenBank Accession No. AAT01711 | | |
|---|---|---|
| Putative domains | From to (or position) | Length |
| Non coding sequence 5' | 1-201 | 201 |
| VP4 | 202-286 | 85 |
| VP2 | 287-504 | 218 |
| VP3 | 505-725 | 221 |
| VP1 | 726-938 | 213 |
| 2A | 939-954 | 16 |
| 2B | 955-1108 | 154 |
| 2C3A + beginning2B | 1109-1587 | 479 |
| 3B' (end) | 1588-1650 | 63 |
| 3C | 1651-1863 | 213 |
| Signal sequence | no | |
| N-glycosylation | 14, 18, 24, 25, 33, 42, 133, 277, 625, 764 | |
| Disulfide bridge | No | |

Example 1.1

Construction of Plasmid pMEB097 Containing Polynucleotide Encoding Polyprotein of FMDV A24 Cruzeiro Strain with a Mutation in VP2 (H93C) for Creation of a Disulfide Bridge (+Optimized Translation Initiation Context) and Generation of Corresponding Recombinant Baculovirus BacMEB097

Generation of Plasmid pMEB097

The plasmid pMEB096 containing wild-type polynucleotide encoding polyprotein of FMDV A24 Cruzeiro strain was mutated to generate plasmid pMEB097. Plasmid pMEB097 contains the polynucleotide (SEQ ID NO:3) encoding a modified polyprotein (SEQ ID NO:2) containing a mutation in VP2 (H93C) or P1 (H179C). The modified polyprotein (SEQ ID NO:2) contains a substitution of Histidine by Cysteine at position 93 of VP2 or position 179 of P1.

Generation of Recombinant Baculovirus BacMEB097

Figure 3:
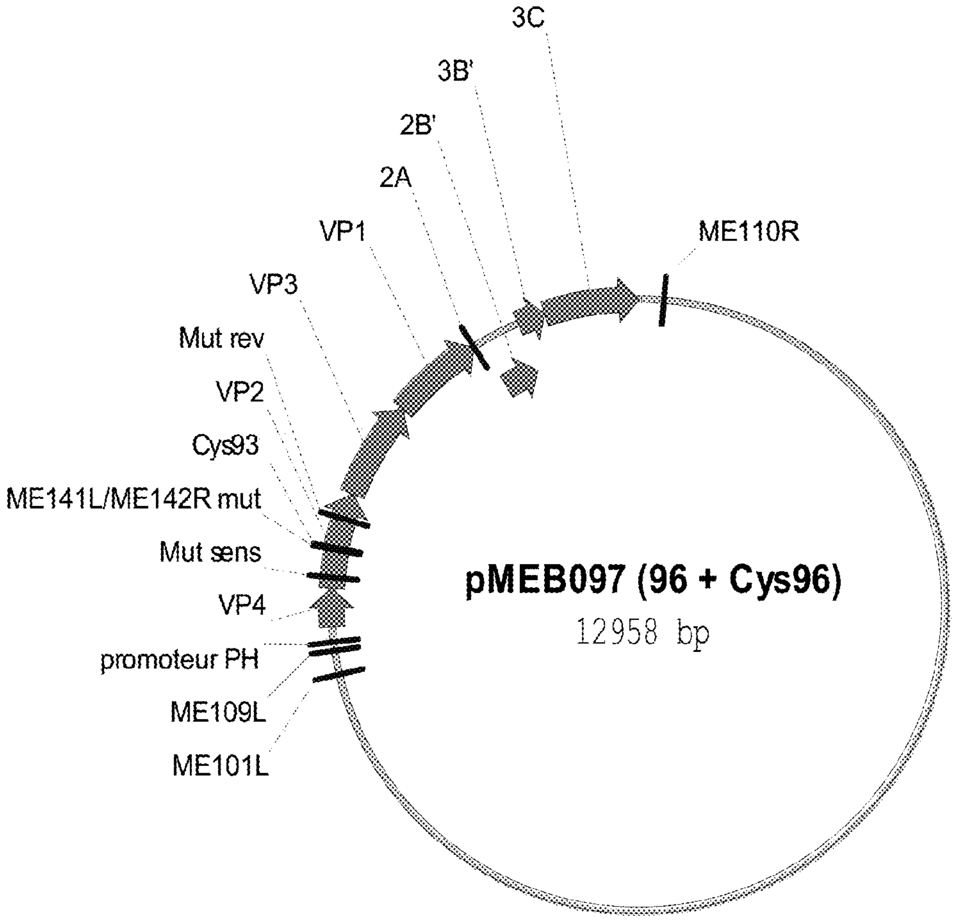
FIG. 3 depicts the plasmid map of pMEB097.

Plasmid pMEB097 (see FIG. 3) was used to generate a recombinant baculovirus, encoding FMDV P1/2A/2B'3B'/3C gene (with cysteine at position 93 of VP2) of FMDV A24 Cruzeiro strain under control of polyhedrin promoter, by homologous recombination. *Spodoptera frugiperda* (Sf) 9 insect cells from ATCC were co-transfected with plasmid pMEB097 and Bsu36I triple-cut linearized AcNPV DNA, according to manufacturer's protocol (Baculogold, Pharmingen). Recombinant baculovirus from co-transfection supernatant were plaque purified twice. Five clones were amplified (passage 1) at 28° C. at a 25 $cm^2$ monolayer flask scale. Five clones were amplified in Sf9 insect cells and recombinant clones were analysed by Western blot using monoclonal antibody which is specific to FMDV A24 serotype. The clone 2 showed a good level of expression. This clone was further amplified (passage 2) at 28° C. at a 50 mL scale in Erlenmeyers (suspension) at 105 rpm. A third passage (passage 3) at a 200 mL scale was performed to obtain virus stock used for protein expression. This virus stock was then titrated by plaque assay. The obtention of the virus stock was performed using SF900III media, supplemented with 2% of FCS. After titration recombinant baculovirus stock (Passage 3) was used for protein production in serum free medium.

Expression Analysis of Baculovirus BacMEB097

Insect cells (Sf9-Invitrogen) were infected by the generated baculovirus BacMEB097 and by BacMEB084 (as reference without mutation) at a Multiplicity Of Infection (MOI) of 1 pfu/ml. Insect cells were grown at 105 rpm in Sf900II medium without FCS during 4 days at 28° C. Supernatants were concentrated around factor 4 and treated as: A=no treatment; B=1 h at 56° C.; C=HCl added to reach a pH below 5.

The correct assembly of the capsid protein into VLPs was assessed by Electronic microscopy (see FIG. 4, column "A"). Particles of 25-30 nm showed very uniform round to eicosahedral morphology, a constant size of 31 nm and was characterised by penetration of stain and hence was interpreted as FMDV-like. The number of particles was estimated at about $10^8$ per ml.

Moreover, the stability of VLPs was clearly increased with the formation of the disulfide bridge brought by the mutation in BacMEB097 as seen after treatment 1 hour at 56° C. (column "B") and by acidification of the medium (column "C").

Figure 5:
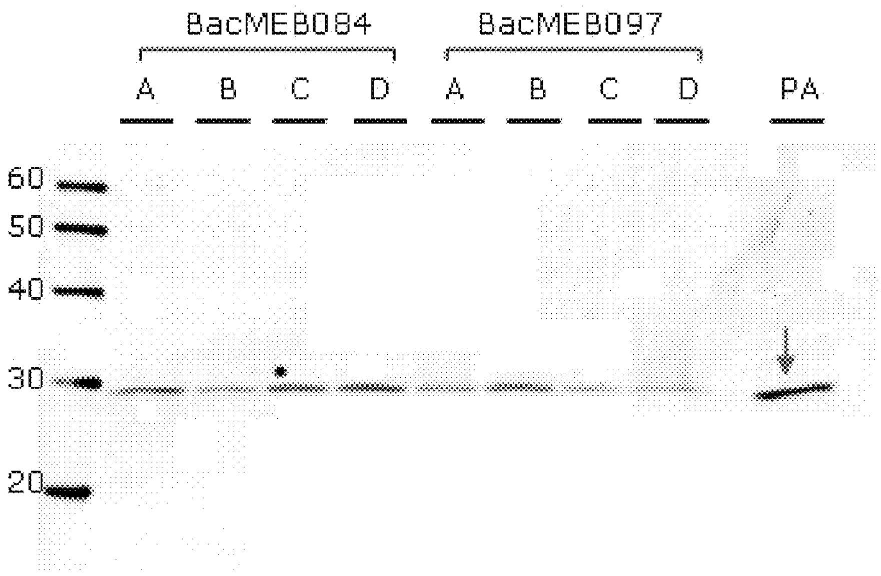
FIG. 5 depicts the western blot results of FMDV capsid protein of A24 strain.
Figure 7A:
Figure 7C:
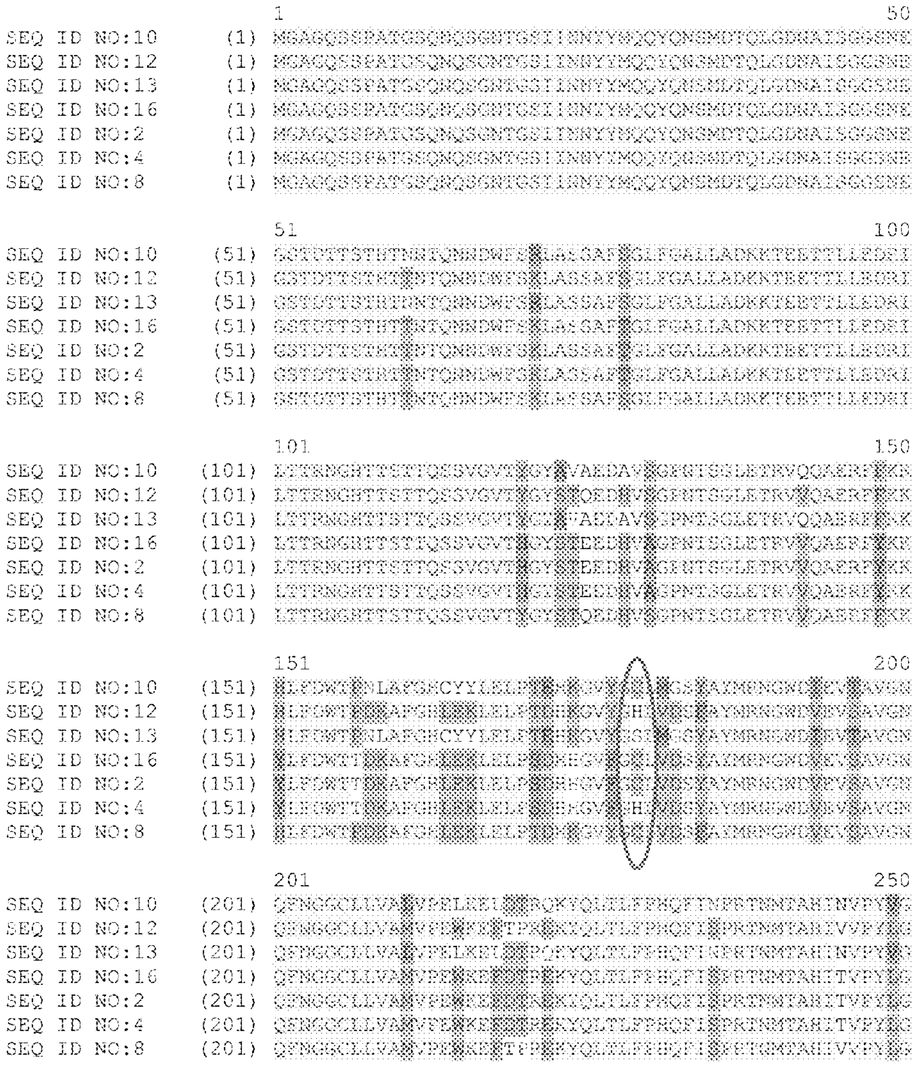

The identity of FMDV protein was confirmed by analysis of the supernatant by Western blot using monoclonal antibody which is specific to FMDV A24 serotype (see FIG. 5).

In conclusion, baculovirus BacMEB097, generated with transfer plasmid pMEB097, induce FMDV capsid expression and processing in Sf9 insect cells. These FMDV expressed capsids auto-assembled into VLPs with characteristic morphology of FMDV like virions. The mutation involving a formation of a disulfide bridge increased the stability of the VLPs (after heat treatment or acidification) compared to VLPs obtained by BacMEB084 (containing plasmid pMEB096 containing wild-type polynucleotide encoding polyprotien of FMDV A24 Cruzeiro strain).

Example 1.2

Construction of Plasmid pMEB099 Containing Polynucleotide Encoding Polyprotein of FMDV O1 Manisa Strain with a Mutation in VP2 (S93C) for Creation of a Disulfide Bridge (+Optimized Translation Initiation Context) and Generation of Recombinant Baculovirus BacMEB099 Expressing FMDV Capsid Proteins The plasmid pMEB095 containing wild-type polynucleotide encoding polyprotien of FMDV O1 manisa strain was mutated to generate plasmid pMEB099. Plasmid pMEB099 contains the polynucleotide (SEQ ID NO:7) encoding a modified polyprotien (SEQ ID NO:6) containing a mutation in VP2 (S93C) or P1 (S179C). The modified polyprotein (SEQ ID NO:6) contains a substitution of Serine by Cysteine at position 93 of VP2 or position 179 of P1.

Generation and expression of recombinant baculovirus BacMEB099 were carried out according to the procedures described in example 1.1 for BacMEB097. Insect cells (Sf9-Inv) were infected by the baculovirus BacMEB099 at a Multiplicity Of Infection (MOI) of 0.5 pfu/ml. Insect cells were grown at 105 rpm in Sf900II medium without FCS during 4 days at 28° C. Protein production was done after treatment of the supernatant: concentration and with or without heating 1 h at 56° C. (to see the effect of the covalent cage mutation). Supernatant treated were analysed directly by electronic microscopy and by specific ELISA (see FIG. 6).

The result (FIGS. 6A and 6B) shows that a significant titer with the ELISA method was obtained. This ELISA is specific for the VLP, suggesting the presence of VLP after infection by BacMEB099.

The correct assembly of the capsid protein into VLPs was assessed by Electronic microscopy (FIG. 6B). Particles of 25-30 nm showed very uniform round to eicosahedral morphology, a constant size of 31 nm and was characterised by penetration of stain and hence was interpreted as FMDV-like. The number of particles was estimated at about $10^8$ per ml.

In conclusion, baculovirus BacMEB099, generated with transfer plasmid pMEB099, induced FMDV capsid expression and processing in Sf9 insect cells. These FMDV expressed capsids auto-assembled into VLPs with characteristic morphology of FMDV like virions.

Example 1.3

Construction of Plasmid pMEB106 Containing Polynucleotide Encoding Polyprotein of FMDV Iraq Strain and Plasmid pMEB104 Containing Polynucleotide Encoding Polyprotein of FMDV Asia Strain with a Mutation in VP2 for Creation of a Disulfide Bridge (+Optimized Translation Initiation Context) and Generation of Recombinant Baculovirus Expressing FMDV Capsid Proteins The plasmids containing the polynucleotide (SEQ ID NO:9) encoding a modified polyprotien (SEQ ID NO:8) containing a mutation in P1 (C at position 179) of FMDV Iraq strain and the polynucleotide (SEQ ID NO:11) encoding a modified polyprotien (SEQ ID NO:10) containing a mutation in P1 (C at position179) of FMDV Asia strain were constructed according to the procedure outlined in example 1.1.

Generation and expression of recombinant baculovirus expressing modified polyprotein (SEQ ID NO:8) of FMDV Iraq strain and polyprotein (SEQ ID NO:10) of FMDV Asia strain were carried out according to the procedures described in example 1.1 for BacMEB097.

The baculovirus BacMEB106 that was generated with transfer plasmid pMEB106 induced FMDV capsid expression and processing in Sf9 insect cells. The baculovirus BacMEB104, generated with transfer plasmid pMEB104, induced FMDV capsid expression and processing in Sf9 insect cells. These FMDV expressed capsids auto-assembled into VLPs with characteristic morphology of FMDV like virions.

Example 2

Stability of Baculovirus-Expressed "Caged" FMDV VLP

Figure 8:
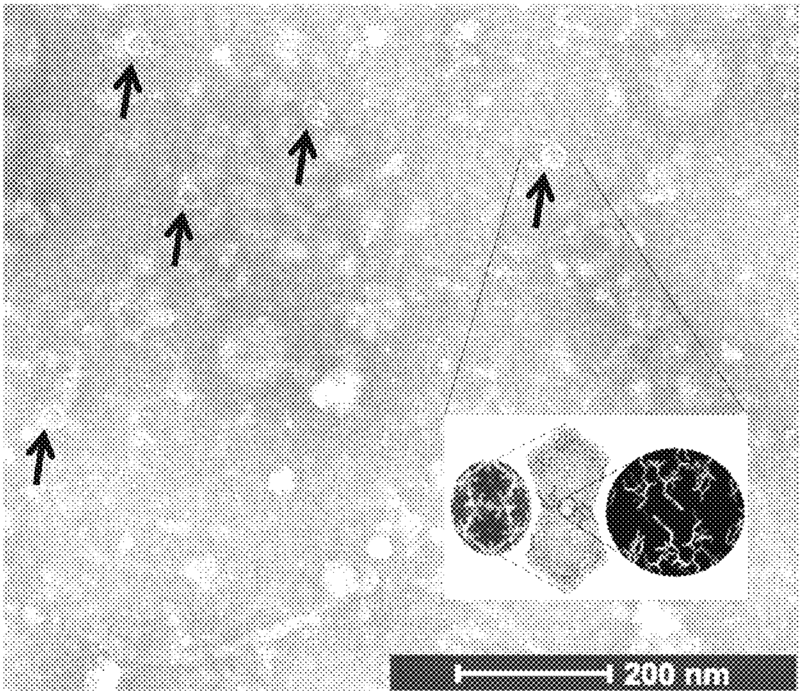
FIG. 8 depicts the FMDV VLPs.

The ability to produce the FMDV VLP in large scale (150 L) was demonstrated. When grown in 150 L batch, manufacturing scale, satisfactory titers of baculovirus-expressed covalent cage and wildtype A24 FMDV-VLPs were obtained (log 10CCID$_{50}$ 7.14/mL) (CCID: cell culture infective dose). Surprisingly, large quantities of stable FMD VLPs were present, even after heating the samples (2.14 log 10 $CCID_{50}$/ml heated against 2.19 log 10 $CCID_{50}$/ml unheated) (see FIG. 8). Moreover, as indicated in FIG. 8, EM counting revealed excellent numbers of VLPs from both the 4 L and 150 L batches.

Example 3

Vaccination of Cattle with Baculovirus, Duckweed and Canarypox Expressed FMDV, and Subsequent Virulent Challenge The purpose of this study was to test, in cattle, the efficacy against an FMD virulent challenge of 3 experimental FMD A24 Cruzeiro antigens, formulated in TS6 adjuvant.

Vaccines containing either Lemna (duckweed, see US2011/0236416), Baculovirus or vCP (canarypox virus) expressed antigens were administered on D0 to bovines (Table 2.1).

Figure 9:
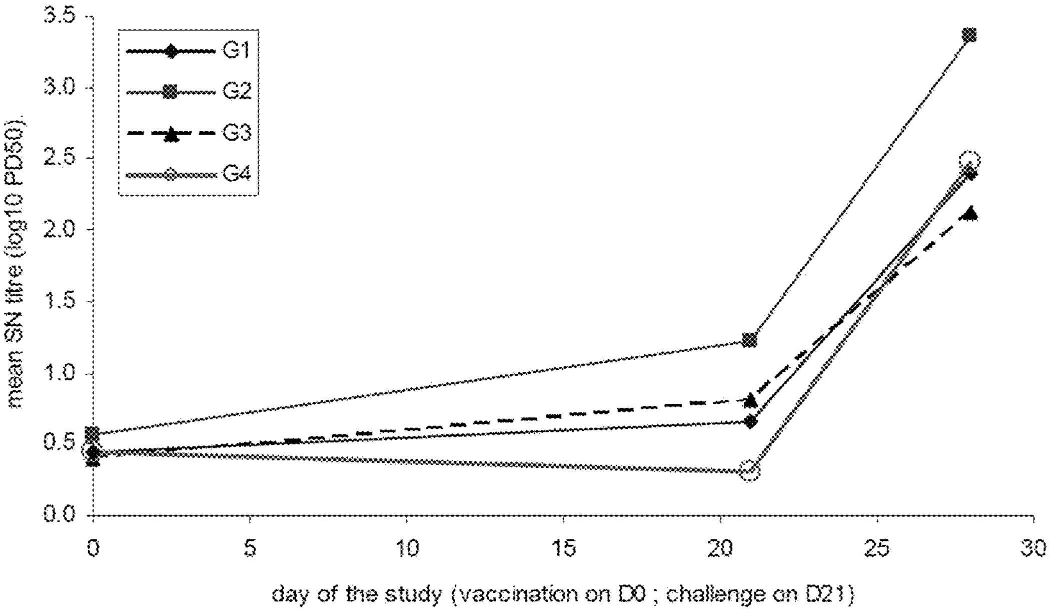
FIG. 9 depicts the evolution of mean FMDV A24 Cruzeiro neutralizing antibody titers.

Vaccine protection was assessed according to the relevant European Pharmacopoeia Monograph, through a virulent FMDV A24 Cruzeiro challenge performed on D21 followed by a clinical monitoring of the bovines (Table 2.2). FMD lesions in the controls validated the challenge. Two animals in the Baculovirus vaccinated group were fully protected from lesions indicating full protection, while the other three presented very limited extension of lesions representing partial protection. The animals in G2 and G3 all presented lesions though the intensity of the lesions varied. Neutralizing titer data are shown in FIG. 9 and FIG. 10. Three weeks after vaccination (D21), a clear sero-conversion was observed in all calves in G2. In G1 and G3, little or no sero-conversion was observed. Controls were negative on that date. All calves strongly sero-converted after challenge (D25 or D28). The sero-response appeared more intense on D28 than D25 and in the vaccinated animals in G2 than in the controls. This observation suggests a priming effect of the vaccination in G2. The results indicate that the Baculovirus FMDV A24 (wildtype A24) vaccine group provided highest SN titers when compared to the other two groups and provided the protection against virulent FMDV A24 Cruzeiro challenge.

TABLE 2.1

Vaccination scheme

| Nature of antigen | Volume of antigen blended | Volume of TS6 adjuvant blended | Volume of vaccine injected per bovine |
|---|---|---|---|
| G1: Lemna FMDV 5x Concentrated (see US 2011/0236416) | 4 mL | 8 mL | 2 mL |
| G2: Baculovirus FMDV (wildy-type) 14.4 × Concentrated | 4 mL | 8 mL | 2 mL |
| G3: vCP2186 (canarypox-vectored FMDV) (see U.S. Pat. No. 7,527,960) | 2.5 mL | 8 mL | 2 mL |

TABLE 2.2

Challenge study design

| Group | # of animals | Vaccine on Do | FMD A24 Cruzeiro challenge on D21 |
|---|---|---|---|
| G1 | 5 | Lemna FMDV + TS6 | Yes |
| G2 | 5 | Baculovirus FMDV + TS6 | Yes |
| G3 | 5 | vCP2186 + TS6 | Yes |
| G4 | 2 | — | Yes |

Example 4

Assessment of Protection in Cattle of Different Experimental FMD A24 Cruzeiro Vaccines (Baculovirus Expressing Wildtype FMDV) in FMDV Challenge Study The goal of the study was to test, in cattle, the efficacy against an FMD virulent challenge of 3 experimental FMD A24 Cruzeiro antigens, formulated in TS6/saponin adjuvant. Vaccines containing FMD A24 Cruzeiro antigen expressed in either, Baculovirus (BacMEB084, filtered or not filtered) or Canarypoxvirus were administered on D0 to bovines. Vaccine protection was assessed (according to the relevant European Pharmacopoeia Monograph), against a virulent FMDV A24 Cruzeiro challenge performed on D21.

TABLE 3.1

Vaccination scheme

| Group | No. Cattle (7-9 months of age on D0) | Vaccine administered on D0 | Volume injected | FMD A24 Cruzeiro challenge on D21 |
|---|---|---|---|---|
| G1 | 5 | A24 (BAC filtered* + TS6/Saponin) | 2 mL | Yes |
| G2 | 5 | A24 (BAC filtered + TS6/Saponin) | 0.5 mL | Yes |
| G3 | 5 | A24 (BAC filtered + TS6/Sap) | 0.125 mL | Yes |
| G4 | 2 | — (Controls) | — | Yes |
| G5 | 5 | A24 (BAC not filtered** + TS6/Sap) | 2 mL | Yes |
| G6 | 5 | A24 (BAC not filtered + TS6/Sap) | 0.5 mL | Yes |
| G7 | 5 | (vCP2166*** + TS6/Sap) | 2 mL | Yes |

A24 BAC filtered*: baculo infectiour titer 8.71 $log_{10}CCID_{50}$/ml
A24 BAC not filtered**: baculo infectiour titer 5.58 $log_{10}CCID_{50}$/ml, $10^8$ VLPs
vCP2166***: baculo infectiour titer 8.8 $log_{10}CCID_{50}$/ml

TABLE 3.2

Summary of the FMD feet lesions observed at necropsy and percentages of protection

| Group | FMD specific lesions Number of animal with feet lesions (number of feet affected per animal) | Percent Protection |
|---|---|---|
| G1 | 0 (0, 0, 0, 0, 0) | 100 |
| G2 | 0 (0, 0, 0, 0, 0) | 100 |
| G3 | 0 (0, 0, 3, 4, 0) | 60 |
| G4 | 2 (4, 4) | 0 |
| G5 | 0 (0, 0, 0, 0, 0) | 100 |

TABLE 3.2-continued

| Summary of the FMD feet lesions observed at necropsy and percentages of protection | | |
|---|---|---|
| Group | FMD specific lesions Number of animal with feet lesions (number of feet affected per animal) | Percent Protection |
| G6 | 1 (0, 0, 1, 0, 0) | 100 |
| G7 | 1 (0, 0, 1, 0, 0) | 80 |

Figure 11A:
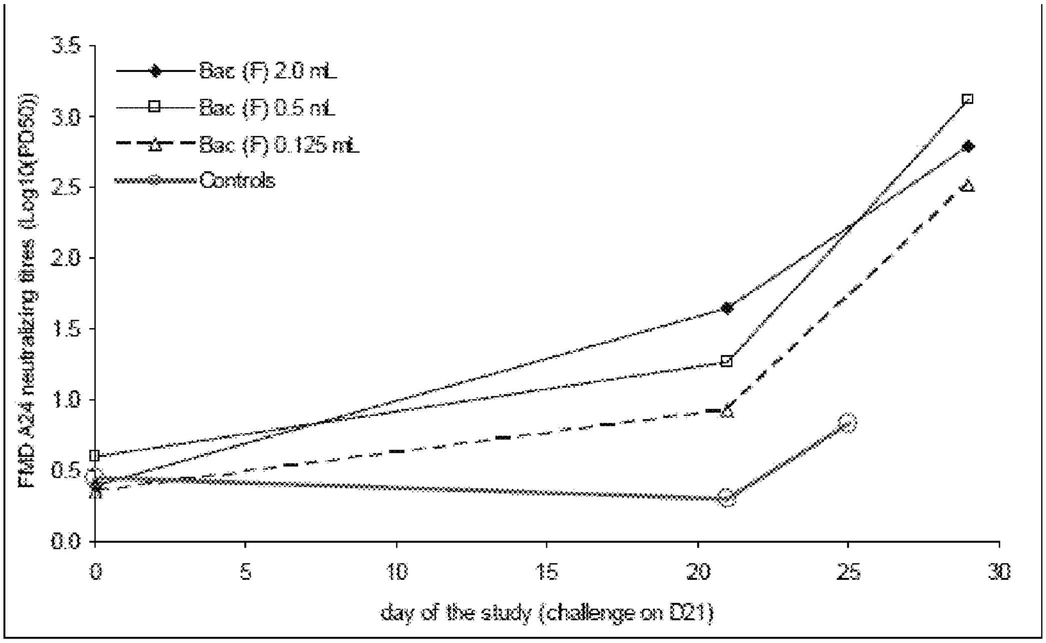
FIGS. 11A and 11B depict the evolution of mean FMDV A24 Cruzeiro neutralizing antibody titers.
Figure 11B:
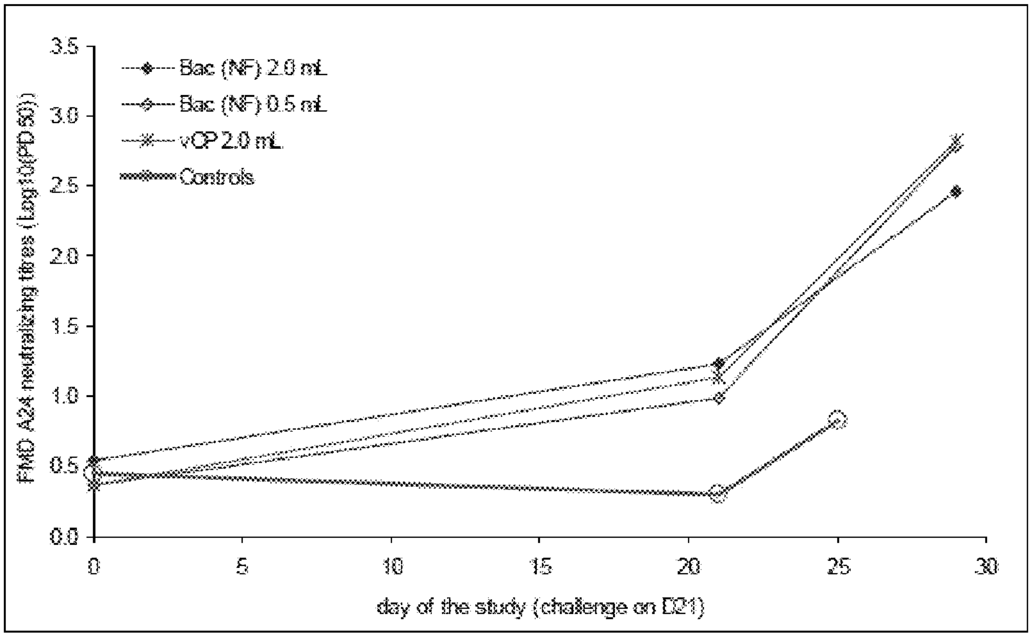
Figure 12A:
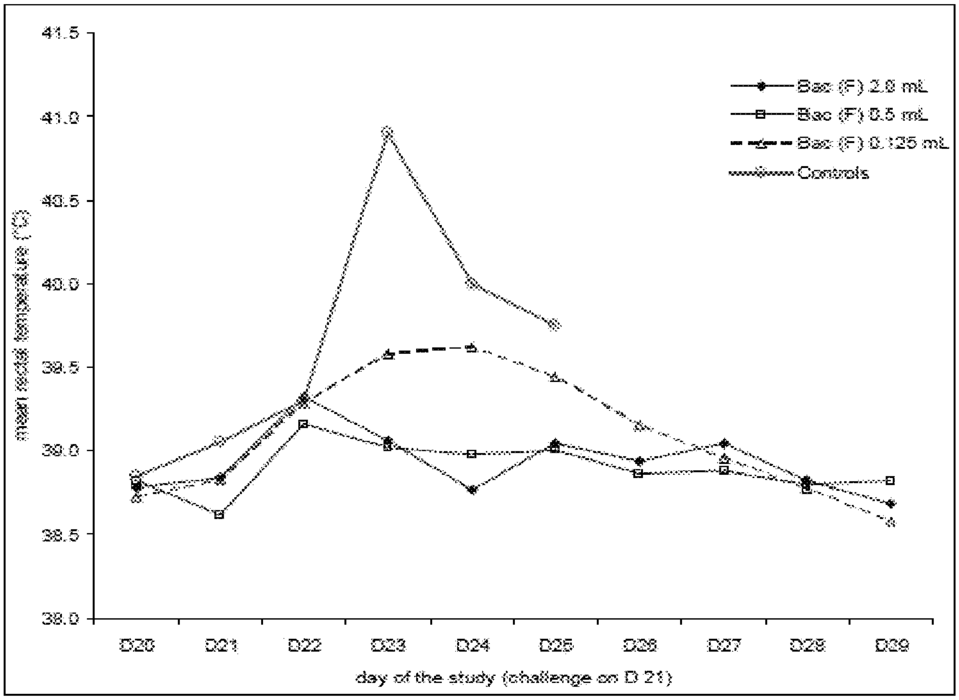
Figure 12B:
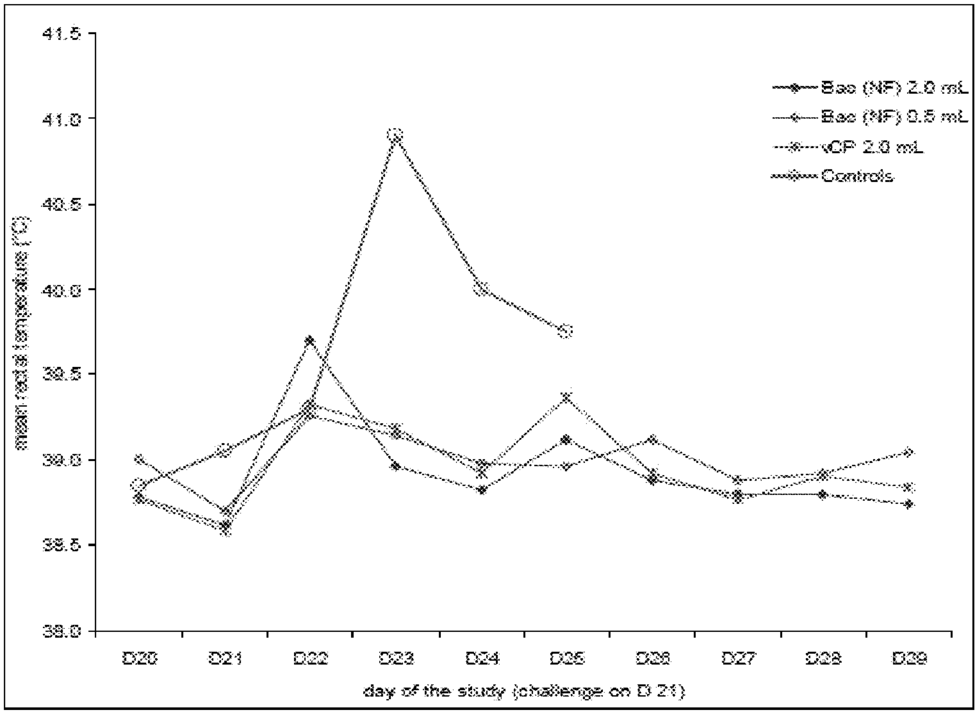

The two Baculovirus vaccines were demonstrated protective in 100% of the animals at full and quarter vaccine dose. The filtered Baculovirus vaccine was still protective in 60% of the animals at a 1/16 vaccine dose. The Canarypoxvirus vaccine was demonstrated protective in 80% of the animals at full dose. FIGS. 11A, 11B and FIG. 12C present graphs and table depicting the FMDV A24 Cruzeiro antibody titers over time. The results show that three weeks after vaccination (D21), a clear sero-conversion was observed in all vaccinated calves. There was a dose/effect relation among the baculo vaccinated groups (G1-G2-G3 and G5-G6). Controls were negative on both dates. All vaccinated calves strongly sero-convereted after challenge (D25 and D28). The sero-response appeared more intense on D28 than D25. Sero-conversion in the controls was rather weak. FIGS. 12A and 12B present the evolution of temperature over time. The results show that only control presented significant temperature increase. The vaccines didn't increase the rectal temperature.

Using these data, the PD50 was calculated using logistic regression and Spearman-Kärber methods. The logistic regression method estimated the strength of vaccine A>16 $PD_{50}$. The Karber method estimated the strength of vaccine A>26$PD_{50}$. While there was a difference between the estimates, both methods suggest a highly significant and substantial efficacy of vaccine A. Given the clinical results, similar estimates for vaccine B also suggested a great efficacy of vaccine B.

Example 5

Immunogenicity in Piglets of Experimental FMDV Formulations Using Baculovirus The objective of this study was to assess the immunogenicity of 4 FMDV antigens expressed in Baculovirus and formulated in TS6 or TS6+Saponin. The vaccines were prepared according to the following proportions (Tables 4.1).

TABLE 4.1

| vaccine formulation | |
|---|---|
| BACMEB097 | FMD A24 modified (covalent cage) antigen (aqueous solution, 656.5 μL), saponin (10 hemaglutinin units), ester of fatty acids and or polyols (12 μL), triester of fatty acids and of ethoxylated polyols (68 μL), light paraffin oil (586.7 μL), ester of fatty acids and of ethoxylated polyols (20% solution, 75 μL), and phosphate buffer (to a 2 mL dose). |
| BACMEB095 | FMD O1 Manisa wild-type antigen (aqueous solution, 656.5 μL), saponin (10 hemaglutinin units), ester of fatty acids and or polyols (12 μL), triester of fatty acids and of ethoxylated polyols (68 μL), light paraffin oil (586.7 μL), ester of fatty acids and of ethoxylated polyols (20% solution, 75 μL), and phosphate buffer (to a 2 mL dose). |
| BACMEB084 | FMD A24 wild-type antigen (aqueous solution, 656.5 μL), saponin (10 hemaglutinin units), ester of fatty acids and or polyols (12 μL), triester of fatty acids and of ethoxylated polyols (68 μL), light paraffin oil (586.7 μL), ester of fatty acids and of ethoxylated polyols (20% solution, 75 μL), and phosphate buffer (to a 2 mL dose). |
| BACMEB084 | FMD A24 wild-type antigen, aqueous solution, 656.5 μL), ester of fatty acids and or polyols (12 μL), triester of fatty acids and of ethoxylated polyols (68 μL), light paraffin oil (586.7 μL), ester of fatty acids and of ethoxylated polyols (20% solution, 75 μL), and phosphate buffer (to a 2 mL dose). |

The antigens studied differed by the serotype (A24 Cruzeiro or O1-Manisa), the method of production (insect cells or silkworm) or the insert (standard or covalent cage). The term "covalent cage" refers the establishment of a non-naturally occurring disulfide bond in the FMDV P1 peptide, which is accomplished by substitution of a cysteine residue. The assessment was performed in young piglets, vaccinated intramuscularly twice, at a 21 days interval. The piglets were monitored for general reactions following each vaccination and were monitored for FMDV-A24 or FMDV-O1M neutralizing antibody titers on D1, D20 and D42.

TABLE 4.2

| vaccination groups | | | | | |
|---|---|---|---|---|---|
| Group | # Pigs | Active Ingredient (AI) | Insert | AI Culture | Adjuvant |
| G1 | 7 | A24 Cruzeiro | Wildtype | SF9 cells | TS6 |
| G2 | 7 | A24 Cruzeiro | Wildtype | SF9 cells | TS6 + Saponin |
| G3 | 7 | A24 Cruzeiro | Covalent cage | SF9 cells | TS6 + Saponin |
| G4 | 7 | A24 Cruzeiro | Wildtype | Silkworm | TS6 + Saponin |
| G5 | 7 | O1-Manisa | Wildtype | SF9 cells | TS6 + Saponin |
| G6 | 7 | — | — | — | — |

The O1-Manisa baculovirus-expressed antigens did not elicit sero-conversion in any of the animals in G5. These data demonstrated, for the first time, that baculovirus-produced FMDV subunits containing the "covalent cage" mutation were immunogenic (see Table 5 below). Moreover, the data here strongly showed that the "caged" FMDV subunits were significantly more productive, effective and stable, when compared to the unmodified wildtype FMDV. Further, the silkworm-based vaccine did not appear to contain significantly more antigen than the other vaccines tested.

TABLE 5

| | FMD-A24 Neutralizing titer ($Log10PD_{50}$) | | | | | | Number exceeding threshold (associated with protective immunity)* | |
|---|---|---|---|---|---|---|---|---|
| | D1 | | D20 | | D42 | | | |
| Group | Mean | sd** | Mean | sd | Mean | sd | D20 | D42 |
| G1 | 0.90 | 0.12 | 1.26 | 0.19 | 1.56 | 0.17 | 1/7 | 6/7 |
| G2 | 1.03 | 0.13 | 1.29 | 0.17 | 1.67 | 0.20 | 2/7 | 7/7 |
| G3 | >0.96 | 0.24 | 1.46 | 0.27 | 2.08 | 0.29 | 3/7 | 6/6 |

TABLE 5-continued

| | FMD-A24 Neutralizing titer (Log10PD$_{50}$) | | | | | | Number exceeding threshold (associated with protective immunity)* | |
|---|---|---|---|---|---|---|---|---|
| | D1 | | D20 | | D42 | | | |
| Group | Mean | sd** | Mean | sd | Mean | sd | D20 | D42 |
| G4 | >1.09 | 0.17 | 1.48 | 0.13 | 1.58 | 0.23 | 4/7 | 4/6 |
| G6 control | 0.92 | 0.18 | 1.07 | 0.13 | 0.94 | 0.17 | 0/7 | 0/7 |

*titer ≥1.35 log10PD$_{50}$;
sd**: standard deviation.

In conclusion, as indicated by the results in Table 5, all SF9 cell-cultured, baculovirus-expressed A24 VLPs (groups G1, G2 and G3) yielded a significant "booster" effect (i.e. second dose significantly increased the number of seroconverting animals.) In contrast, the silkworm cultured A24 VLPs appear to have elicited an initial and persistent serological response, without having elicited an apparent booster effect.

Example 6

Acid and Heat Stability of the Baculovirus-Expressed A24 FMDV VLPs

Figure 15:
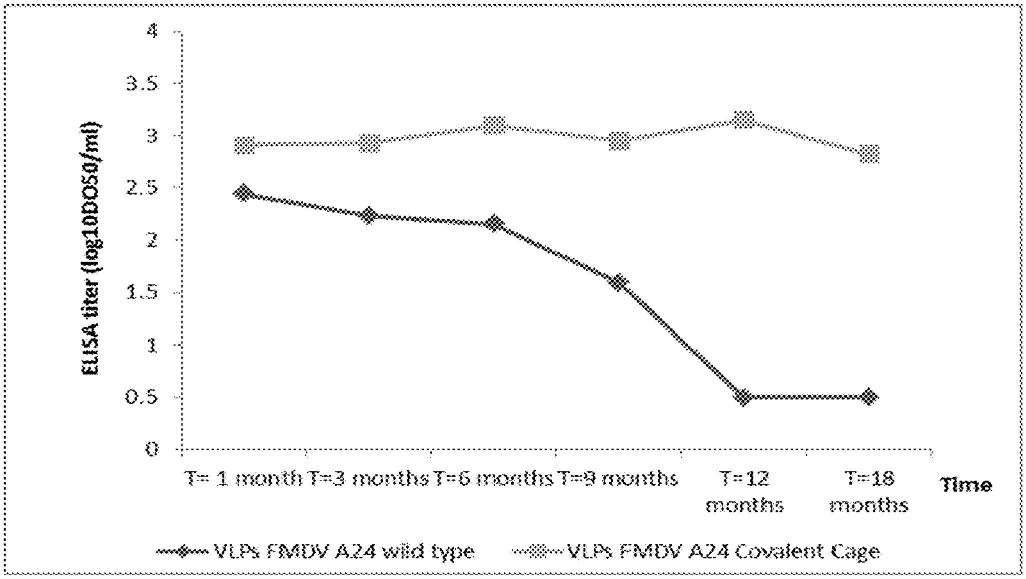
FIG. 15 depicts the ELISA analysis of A24 Cruzeiro VLPs with or without the covalent cage mutation stored at 5° C. over time.

A24 FMDV VLPs were subjected to acid and heat treatments, and their stability was evaluated using EM (FIG. 13) and ELISA analysis (FIG. 14). As indicated in the figures, the covalent cage VLPs, but not the wild type VLPs, were significantly resistant to both low pH and heat. Moreover, as indicated in FIG. 15 and Table 6, the covalent cage VLP were significantly more stable over time when stored at 5° C., relative to their wild type counterparts.

TABLE 6

Stability of A24 VLPs (covalent cage vs. wild type)

| | T0 | T1 month | T6 months | T9 months | T12 months |
|---|---|---|---|---|---|
| VLPs FMDV A24 Covalent cage | 10E9 | 5.10E8 | 3.10E8 | 3.10E9 | 10E8 |
| VLPs FMDV A24 Wild Type | 10E9 | 5.10E8 | 5.10E7 | No VLPs observed | No VLPs observed |

Figure 16:
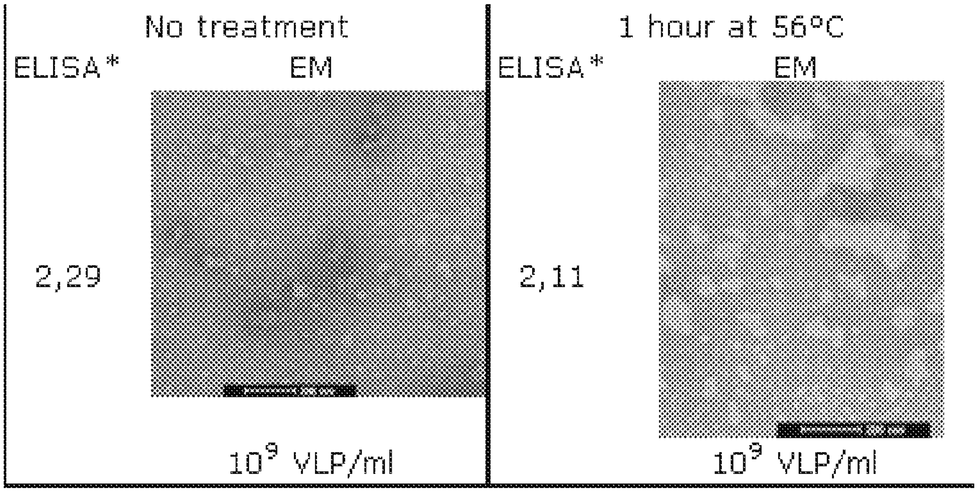
FIG. 16 depicts the ELISA results and EM pictures showing O1 Manisa covalent cage VLPs are resistant to heat.

In conclusion, the stabilization of VLPs from the A24 Cruzeiro serotype with the "covalent cage mutation" was highly effective regarding resistance to heating or acidification treatments. Covalent cage stabilized VLPs after an 18 month storage. Several FMDV serotypes have now been shown to be effectively stabilized by the introduction of the covalent cage mutation, including: A24 Cruzeiro; O1 Manisa (FIG. 16, EM & FIG. 17, ELISA); Asia 1 Shamir; and A22 Iraq. FIG. 17 shows no impact of heating on stabilized VLPs (covalent cage, BacMEB099) whereas no signal was detected for standard FMDV O1-Manisa active ingredient after heating indicating no assembled VLPs for standard FMDV O1 Manisa after heating.

Example 7

Immunogenicity of Vaccines Formulated with Baculovirus FMD O1 Manisa (Modified, Covalent Cage) in Conventional Piglets The objective of the study was to assess the safety and efficacy in conventional pigs, of two Baculovirus FMD O1-Manisa antigens, formulated in TS6 and one Adenoviral-vectored FMDV O1-Manisa. Each formulation was administered in two injections three weeks apart (D0-D21). Pigs were 11-12 weeks of age on D0 and received 2 mL intramuscular infection of the vaccines. Safety was assessed through monitoring of local and general reactions. Efficacy was assessed through serological (Sero-neutralization titers) monitoring (D1, D20, D43) and cell mediated immunity (CMI) assays (D27, D43).

TABLE 7.1

Characteristics of the antigens and vaccines

| Group | vaccine | type | adjuvant |
|---|---|---|---|
| G1 | Bac099 FMDV VLP covalent cage batch 1 | O1-Manisa (covalent cage) | TS6 |
| G2 | Bac099 FMDV VLP covalent cage batch 2 | O1-Manisa (covalent cage) | TS6 |
| G3 | AFTOPOR ™ Classical Inactivated FMDV vaccine (O1 manisa) | O1-Manisa<br>O Thailand<br>O1 BSF | — |
| G4 | Adenoviral-vectored FMDV | O1-Manisa | — |
| G5 | control | — | — |

Blood samples were collected on D27 and D43 for Cell Mediated Immunity (CMI) assays. Samples were assayed after re-stimulation either for γ Interferon (IFNγ) secreting cell quantification, plasma cell quantification or memory B cell quantification (see Table 7.2). All quantifications were performed by ELISpot.

TABLE 7.2

CMI assays

| Quantification assays | Ex vivo re-stimulation with | D27 | D43 |
|---|---|---|---|
| IFNγ secreting cells | VLP FMDV O1 M + irrelevant control<br>Peptide pool O1 M + irrelevant control | +<br>+ | NT<br>NT |
| Specific IgG secreting plasma cell | VLP FMDV O1 M + irrelevant control | + | NT |
| Specific IgG secreting memory B cells | VLP FMDV O1 M + irrelevant control | NT | + |

+: tested;
NT: not tested

The results showed surprisingly that unlike baculovirus expressed wild-type FMDV O1 M (see example 5), the baculovirus expressed modified (covalent cage) FMDV O1 M elicited secoconversion in piglets. As shown in Table 7.3 below, after first vaccination (D0), seroconversion was observed in the 2 baculovirus groups (G1 and G2) on D20. After second vaccination, booster effect was observed in both groups (G1 and G2).

TABLE 7.3

| Serology study of baculovirus FMD O1 Manisa in piglets | | | | |
|---|---|---|---|---|
| Serology Evaluation | # piglets | SN titer (log 10) D1 | SN titer (log 10) D20 | SN titer (log 10) D43 |
| G1 | 7 | 1.19 | 1.65 | 1.91 |
| G2 | 7 | 1.48 | 1.49 | 1.80 |
| G3 | 4 | 1.50 | 2.22 | 2.67 |
| G4 | 5 | 1.32 | 1.74 | 1.77 |
| G5 | 1 | NT | NT | 1.27 |

Figure 20:
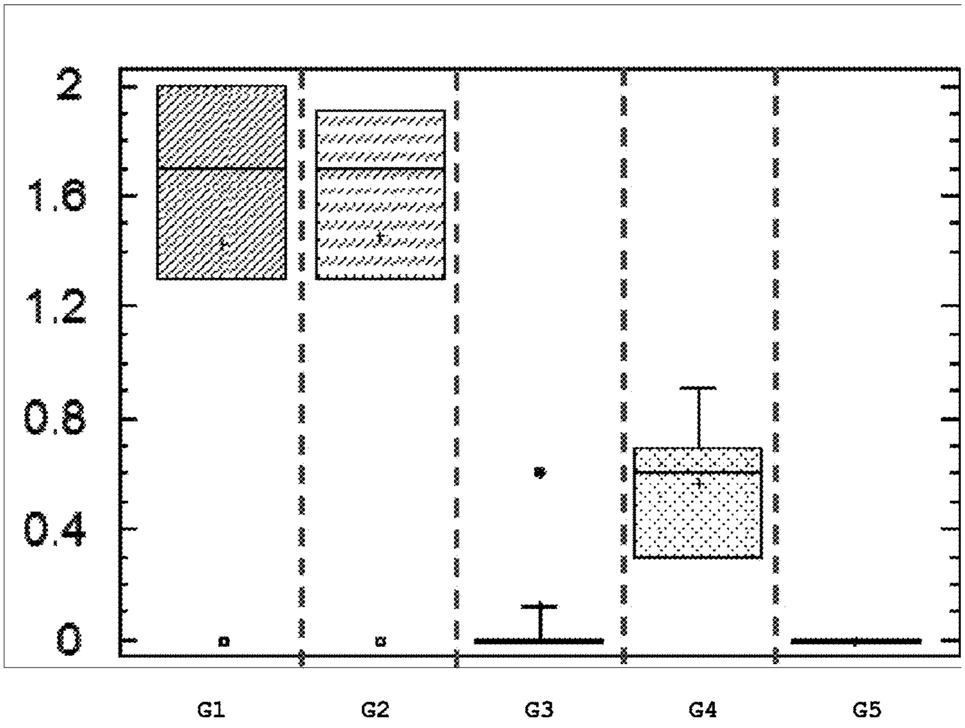
FIG. 20 depicts the B cell ELISPOT assay in the FMDV VLP vaccinated animals on day 27.

As shown in FIG. 20, specific IgG secreting plasma cells were detected in both baculovirus expressed FMDV-VLP (modified, covalent cage)/TS6 vaccinated groups (G1 and G2). The specific IgG secreting plasma cells were significantly higher in G1 and G2 than in G4. No specific IgG secreting plasma cells were detected in G3.

Figure 21:
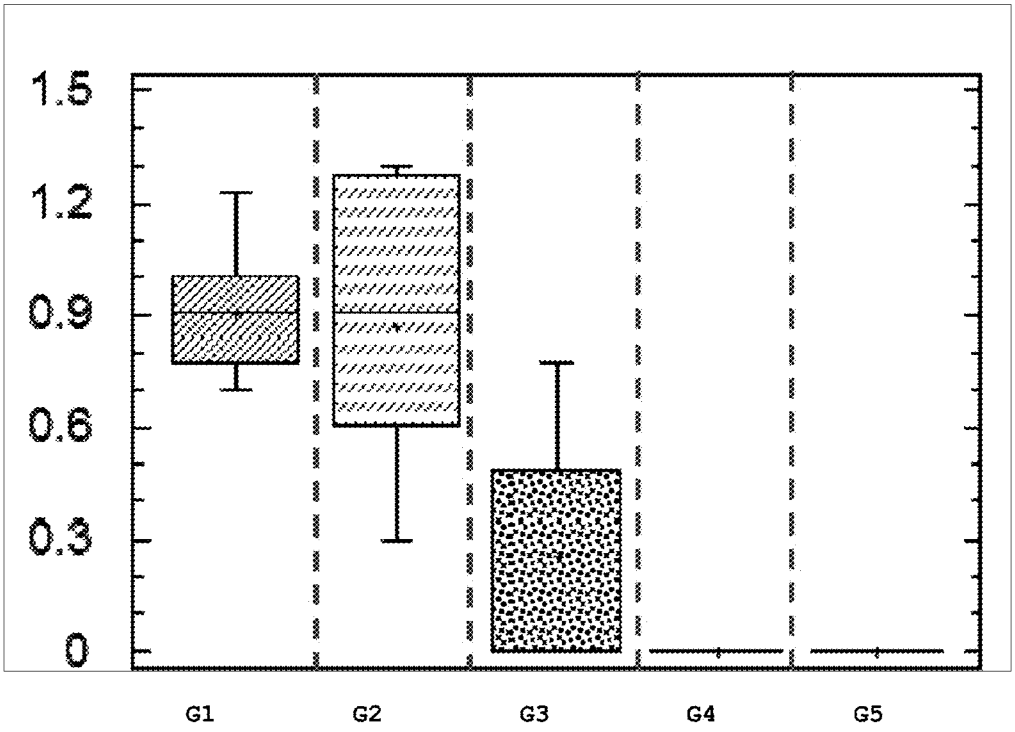
FIG. 21 depicts the B cell ELISPOT assay in the FMDV VLP vaccinated animals on day 43 (measuring B Memory cells).

FIG. 21 shows that high numbers of specific IgG secreting memory B cells were detected in all vaccinated pigs in groups G1 and G2, a weak portion of specific IgG secreting memory B cells were detected in G3, and no specific IgG secreting memory B cells were detected in G4.

Figure 22:
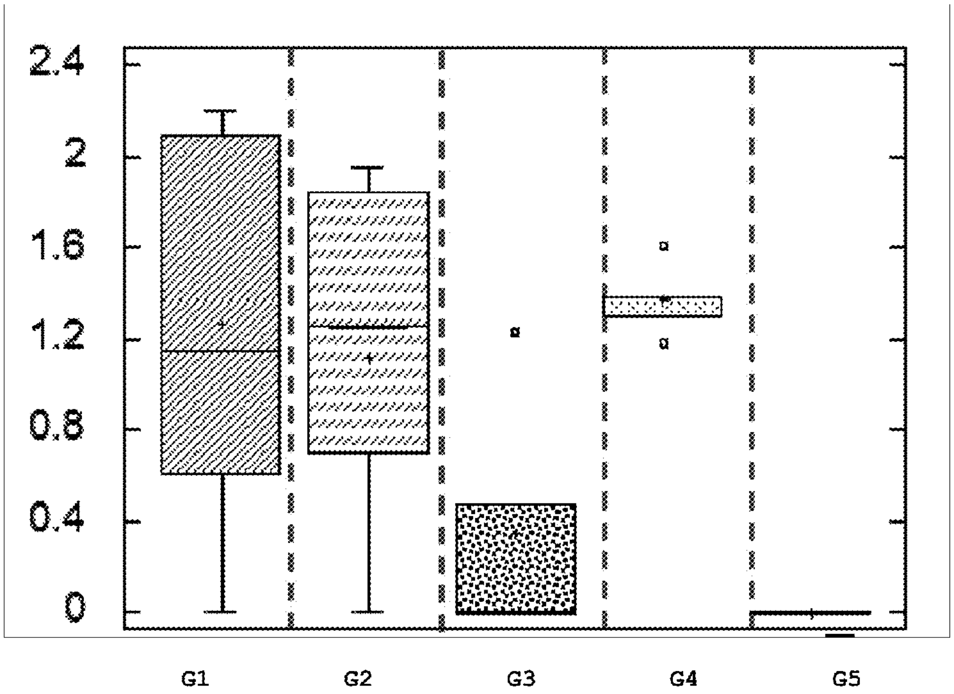
FIG. 22 depicts the specific γ Interferon (IFNγ) secreting cell assay in the FMDV VLP vaccinated animals on day 27.

FIG. 22 shows that specific IFNγ secreting cells were detected in all vaccinated groups in the order of G1 and G2>G4>G3. There is no difference between G1 and G2. The specific IFNγ secreting cells were significantly higher in G1 and G2 than in G3.

The high levels of specific IFNγ secreting cells, specific IgG secreting plasma cells and specific IgG secreting memory B cells in both baculovirus expressed FMDV-VLP (modified, covalent cage)/TS6 vaccinated groups (G1 and G2) indicate good levels of protection against FMDV infections.

Example 8

Asia Shamir BacMEB102 (Wild Type) & BacMEB104 (Covalent Cage)

TABLE 8

| Stability of Asia Shamir VLPs (BacMEB102, wild type and BacMEB104, covalent cage) measured by EM | |
|---|---|
| | EM |
| A Shamir BacMEB102 (WT), P3 D4 pH 7, heated | No VLPs |
| A Shamir BacMEB104 (covalent cage), P3 D4 pH 7, heated | 5.10E7; 1.0E9 (7 month); 2.10E9 (9 month); 10E8 (15 month) |

The results showed that large quantities of stable FMD VLPs for BacMEB104 (covalent cate) were present after heating, and the VLPs were stable up to at least 15 months while the BacMEB102 (WT) didn't form any detectable VLPs after heating.

Example 9

Iraq 22 BacMEB106 (Covalent Cage) Stability

TABLE 9

| Stability of Iraq 22 VLPs (BacMEB105, wild type and BacMEB106, covalent cage) measured by EM after heating | | |
|---|---|---|
| AI | EM | Biacore |
| A22-Iraq BacMEB106 | 3 × 10E9; 5 × 10E8 (3 months) | + |

Compared to covalent cage Iraq22 VLPs, wild type Iraq22 VLPs were not stable after heating at Day 0.

Example 10

Asia Shamir Covalent Cage & Iraq A22 Covalent Cage Serology Study in Pigs

The objective of the study was to assess the immunogenicity in conventional pigs, of FMD Asia1 Shamir and FMD A22 Iraq VLP antigens, produced in Baculovirus. Two batches of Asia1 Shamir antigen and 2 batches of A22 Iraq antigens were tested in TS6 formulations. Each formulation was administered in two injections three weeks apart (D0-D21) to pigs. Pigs were 8-9 weeks of age on D0. Immunogenicity was assessed through serological monitoring (D-1, D20, D42) and cell mediated immunity (CMI) assays (D26, D41).

TABLE 10

| Vaccination scheme of Asia Shamir VLPs (BacMEB104, covalent cage) and A22 IraqVLPs (BacMEB106, covalent cage), two injections at D0 and D21 | | |
|---|---|---|
| Group | Antigen | Adjuvant |
| G1 (n = 5) | Asia1 Shamir VLP CC | TS6 |
| G2 (n = 5) | A22 Iraq VLP CC | TS6 |
| G3 (n = 4) | Asia1 Shamir VLP CC | TS6 |
| G4 (n = 4) | A22 Iraq VLP CC | TS6 |
| G5 (n = 2) | Unvaccinated | — |

Figure 18A:
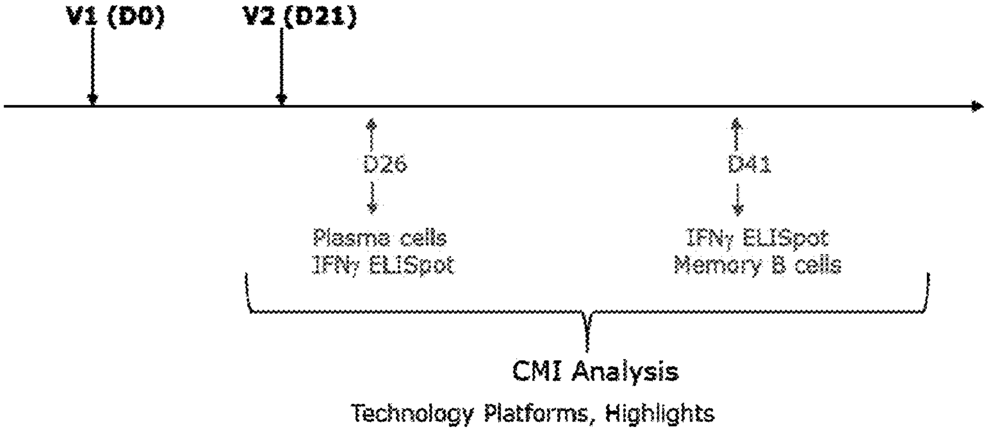
FIG. 18A depicts the vaccination and analysis scheme.
Figure 18B:
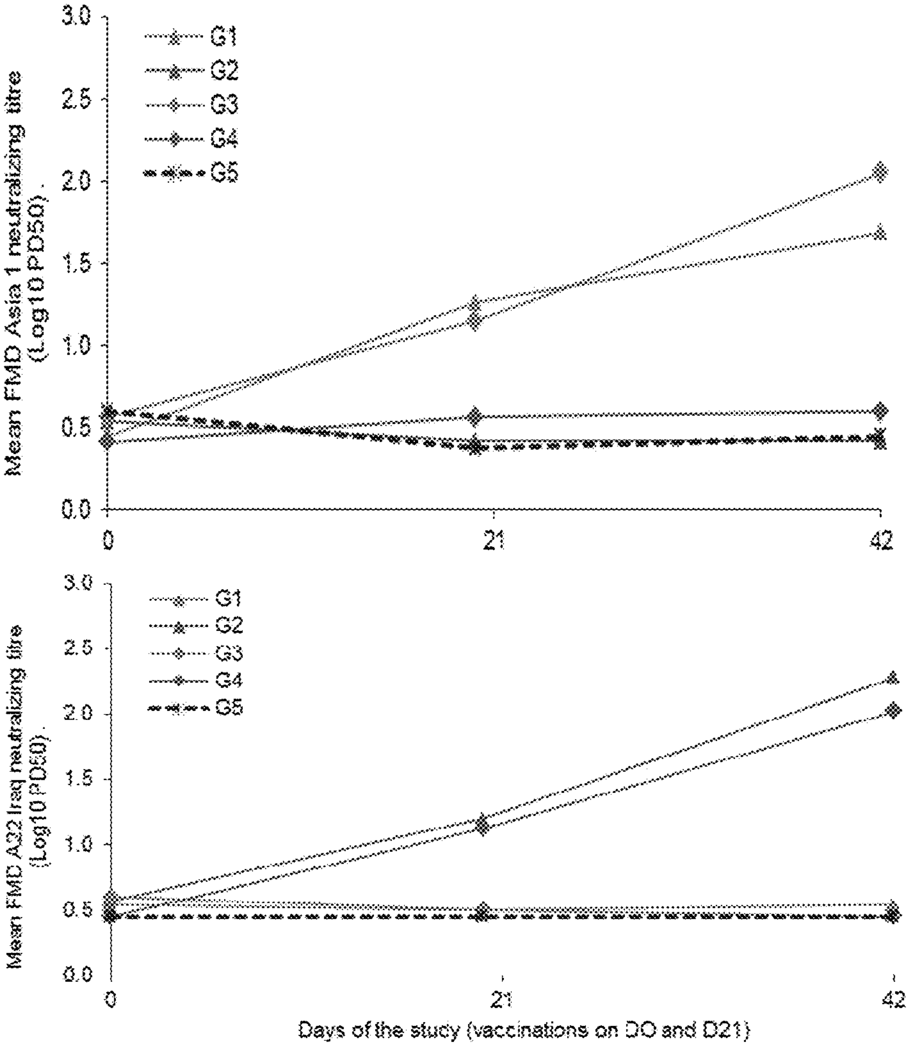
FIG. 18B depicts the evolution of neutralizing antibody titers against FMD Asia1 Shamir and FMD A22 Iraq.

As indicated in FIG. 18, covalent cage VLPs from both strains elicited strong, serotype-specific, serological responses.

All pigs vaccinated with the VLP Asia1 Shamir (G1 & G3) had clearly sero-responded to first vaccination, with an average titer close to 1.20 Log 10 PD50. Further, there was a clear booster effect following second vaccination, with most pigs exceeding a titer of 1.8 Log 10 PD50. The controls (G5) and most of the A22 Iraq vaccinated pig (G2 & G4) did not show any sero-response against Asia1 Shamir, even after a booster vaccination.

All pigs vaccinated with the VLP A22 Iraq (G2 & G4) had sero-responded to first vaccination, with an average titer close to 1.15 Log 10 PD50. Further, there was a strong booster effect following second vaccination, with most pigs exceeding a titer of 2.0 Log 10 PD50. The controls (G5) and most of the Asia1 Shamir vaccinated pig (G1 & G3) did not show any sero-response against A22 Iraq, even after a booster vaccination.

Figure 19A:
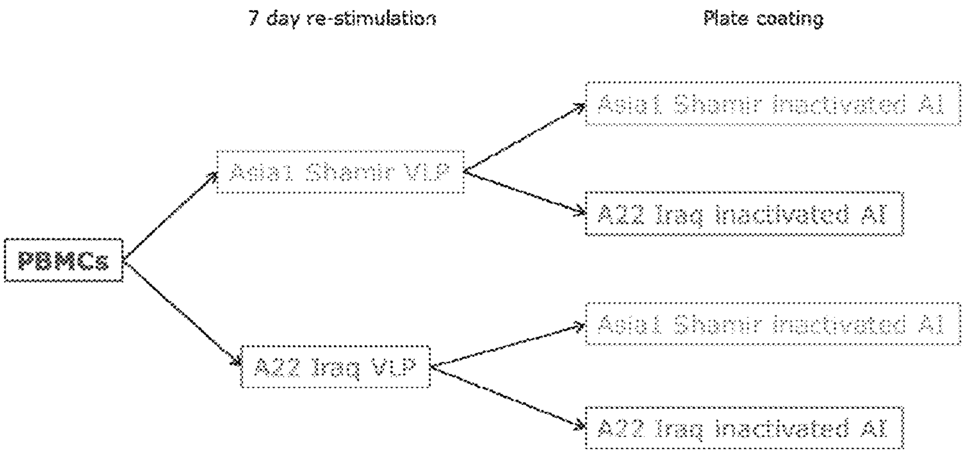
FIG. 19A depicts the humoral response (memory B cells detection) scheme.

Surprisingly, cross-reactivity was observed, as indicated in FIG. 19. The results have shown that specific IFNγ response (cellular response) was detected in both Asia1

Shamir VLP groups when Asia1 Shamir FMDV peptide pool was used, and specific IFNγ response (cellular response) was detected in both A22 Iraq VLP groups when A22 Iraq FMDV peptide pool was used. The Asia1 Shamir VLP group showed cross-immunogenicity when A22 Iraq FMDV peptide pool was used. Specific plasma cells (humoral response) were detected in both Asia1 Shamiar VLP groups and both A22 Iraq VLP groups with Asia1 Shamir inactivated AI coating and A22 Iraq inactivated AI coating, respectively. Cross-immunogenicity (plasma cells) in Asia1 Shamir VLP groups was observed with A22 Iraq inactivated AI coating. Specific memory B cells (humoral response) were detected in both Asia1 Shamiar VLP groups and both A22 Iraq VLP groups with Asia1 Shamir AI coating and A22 Iraq AI coating, respectively. Good cross-immunogenicity (B cells) in Asia1 Shamir VLP groups was observed with A22 Iraq AI coating. Some cross-immunogenicity (B cells) in A22 Iraq VLP groups was also observed with Asia1 Shamir AI coating. Taken together, the results indicate the VLPs could elicit an immune response sufficient to protect against heterologous challenge.

In conclusion, the 4 FMDV serotypes-VLPs antigens (A24, 01 Manisa, Asia1 Shamir and A22 Iraq) adjuvanted in TS6 induced humoral and cellular responses with strong, serotype-specific, neutralizing antibody responses, consistent proportion of specific IFNγ responses, presence of memory B cells (with cross-reactivity between the 2 serotypes), indicating good levels of protection against homologous and heterologous FMDV infections.

Example 11

Construction of Human Adenovirus 5 Vectored Recombinant FMDV

The goal of the study is to generate an adenovirus recombinant expressing the codon optimized FMDV structural proteins and non-optimized 3C protease with a C142T site mutation for serotype A24 Cruzeiro. The FMDV antigen contains FMDV capsid precursor (VP1, VP2 (with H93C site mutation, covalent cage), VP3, VP4, 2A, and full 2B codon optimized) and a non-optimized partial 3B and full length 3C protease with C142T site mutation (SEQ ID NO:16).

HEK 293 cells (ATCC) were maintained in MEM (Gibco #11095) with 10% Fetal Bovine serum (Moregate Batch #81827101) at 37° C. in 5% CO2. These cells were used to rescue the recombinant adenovirus vAD3027 and make virus stocks.

Figure 25:
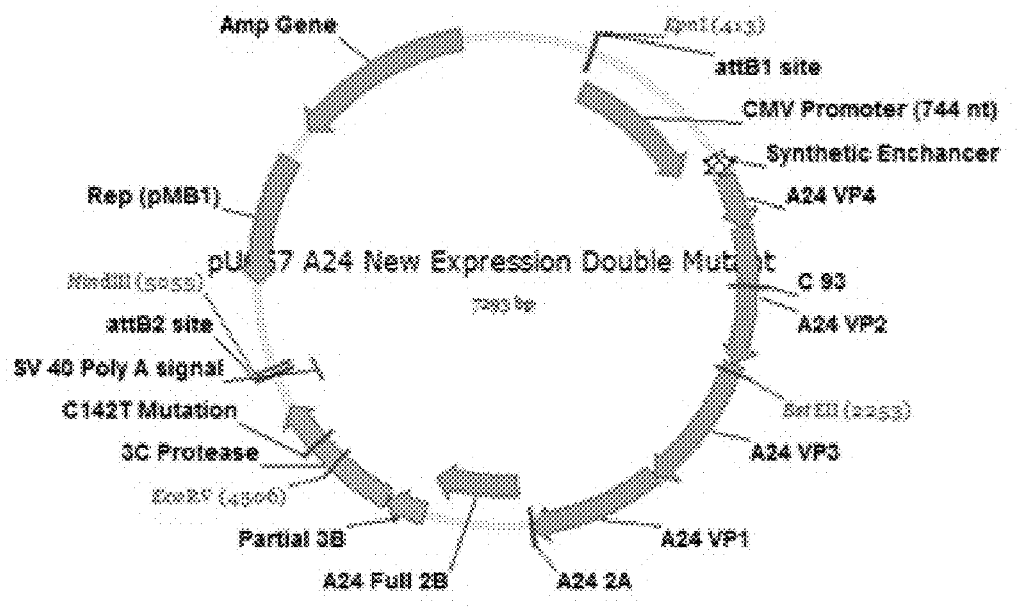
FIG. 25 depicts plasmid pAD3027 map.

The expression plasmid pAD3027 (see FIG. 25) contains codon-optimized polynucleotide (SEQ ID NO:17 encoding FMDV capsid protein SEQ ID NO:16) linked to CMV promoter and SV40 polyA tail. The polynucleotide includes a synthetic intron.

The expression clones were generated by LR recombination of entry vector with destination vector using Gateway technology (Invitrogen). Recombinant adenovirus vAD3027 were generated by transfection of linearized expression clones in HEK 293 cells with transfection reagent. After rescue, each virus was harvested by freeze-thaw cycle and clarification the cell debris by centrifugation. For passage, each virus was inoculated into monolayer of HEK 293 cells and approximately 3-4 days post infection, virus was harvested by freeze-thaw cycle and clarification by centrifugation. Five passages were conducted to make virus stock, which was stored at −80° C.

Figure 26:
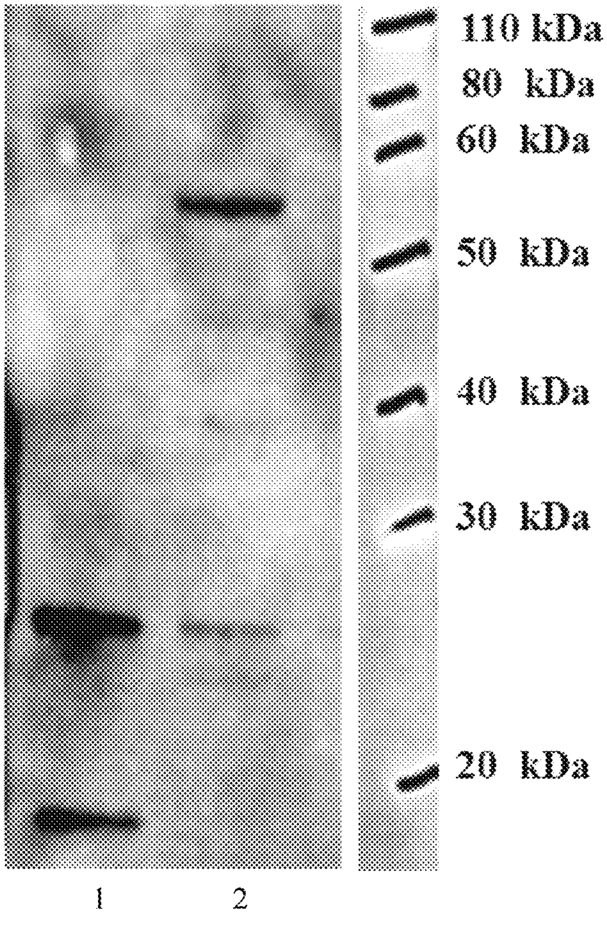
FIG. 26 depicts Western Blot of vAD3027.

Sequence analysis of the recombinant clone has confirmed that sequences from the beginning of the CMV promoter to the end of the SV40 tail were correct (SEQ ID NO:20). The immunofluorescence testing showed that all examined plaques of vAD3027 were found to express FMDV capsid protein. Western Blot using the antibody against VP2 protein detected the liner epitope of VP2 either as VP2 (fully processed ~25 kDA), VP0 (partially processed transgene ~37 kDa) or P1 (unprocessed transgene ~80 kDa) expressed by vAD3027 (see FIG. 26).

The adenovirus recombinants expressing the codon-optimized FMDV modified (covalent cage) capsid protein for O1 Manisa, Asia and Iraq strains were constructed according to the procedures described above.

Example 12

Serology Assessment of Various Foot and Mouth Disease Virus (FMDV) Vaccine Candidates Following Vaccination in Pigs

Example 12.1

Serology Assessment of FMDV A24 Vaccines

The goal of the study is to evaluate the immunogenicity of various FMDV A24 vaccine formulations including human adenovirus 5-vectored FMDV vaccine and Baculovirus expressed FMD A24 recombinant VLP (covalent cage) vaccine in conjunction with different adjuvants (or without) following vaccination in pigs.

Sixty conventionally reared piglets (approximately 1 month of age) were each randomized to one of nine treatment groups each containing 4-7 pigs. The resulting group composition is presented in Table 11 below.

TABLE 11

Vaccination scheme of human adenovirus 5-vectored FMDV vaccine and Baculovirus expressed FMD A24 recombinant VLP vaccine, two injections at D0 and D21

| Group | Vaccine** | Adjuvant (s) | No. of Animals |
|---|---|---|---|
| 1 | BacA24VLP[1] (TV1) | TS6 | 5 |
| 2 | BacA24VLP (TV2) | TS6 + Carbopol | 6 |
| 3 | BacA24VLP (TV3) | TS6 + polymer | 6 |
| 4 | BacA24VLP (TV4) | ISA206 + carbopol | 6 |
| 5 | BacA24VLP (TV5) | ISA206 + polymer | 3 |
| 6 | vAD3027[2] (TV6) | Poly IC | 7 |
| 7 | vAD3027 (TV8) | Poly ICLC | 7 |
| 8* | vAD3027 TV7 (D0); BacA24VLP TV1 (D21) | N/A(D0); TS6 (D21) | 7 |
| 9 | control | N/A | 4 |

TV: Test Vaccine.

BacA24VLP[1]: Baculovirus expressed FMD A24 recombinant VLP (covalent cage) vaccine.

vAD3027[2]: human adenovirus 5-vectored FMDV A24 (covalent cage) vaccine.

*Group 8 received the TV7 at D0 and the TV1 at D21.

**The target dose per piglet was: $10^{3.9}$ VLPs in 0.6 mls of active ingredient for those vaccinated with the BacA24VLP and $10^{10.35}$ $TCID_{50}$ for those vaccinated with the vAD3027 construct.

Each piglet was vaccinated, except those from Group 9 (control), twice at a 21-day interval, with 2 ml of the test vaccine. All injections were given via the intramuscular route (IM) in the neck region, caudal to the ear, alternately on the right and left sides.

Blood samples were collected from all piglets on Days 0 (prior to vaccination), 7, 15, 21 (prior to vaccination), 28, 35 and 42. Day 42 serum samples from all piglets were tested for FMDV antibodies by Serum Virus Neutralization (SVN).

Samples from those vaccinated with the vAD3027 construct and control (Groups 6-9) were subject to SVN assay on all collection days.

All piglets from Groups 1-9 tested negative for FMDV antibodies prior to the start of the study. All piglets in control were negative for FMDV antibodies throughout the study.

Figure 23:
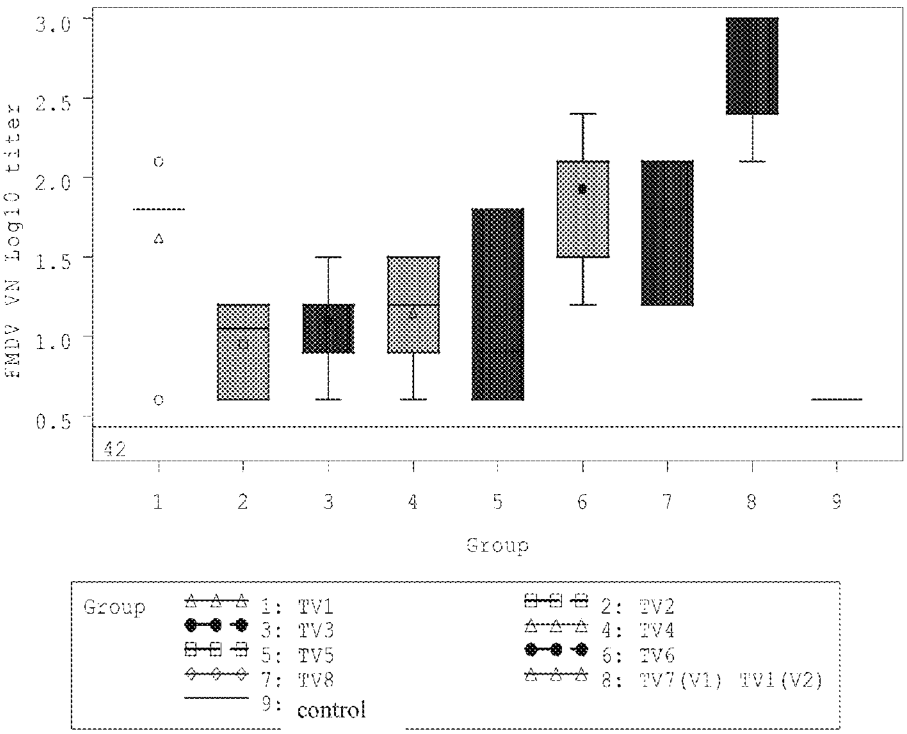
FIG. 23 depicts FMDV SVN log 10 titer by Groups for Day 42.

The FMDV SVN results are shown in FIG. 23. The results demonstrated that both FMD A24 recombinant VLP vaccine and human adenovirus 5-vectored FMDV vaccine induced immune response in animals. At a low dose of $10^{3.9}$ VLPs, FMD A24 recombinant VLP vaccine induced good immune response in the animals. Animals vaccinated with the human adenovirus 5-vectored FMDV vaccine (groups 6-7) had a higher antibody response following a two-dose vaccination regimen than those vaccinated with the low dose FMD A24 recombinant VLP vaccine. Surprisingly, heterologous prime-boost regimen with viral vectored FMDV vaccine and BacA24 VLP vaccine demonstrated stronger immune response than prime-boost with the same vaccines.

Figure 24:
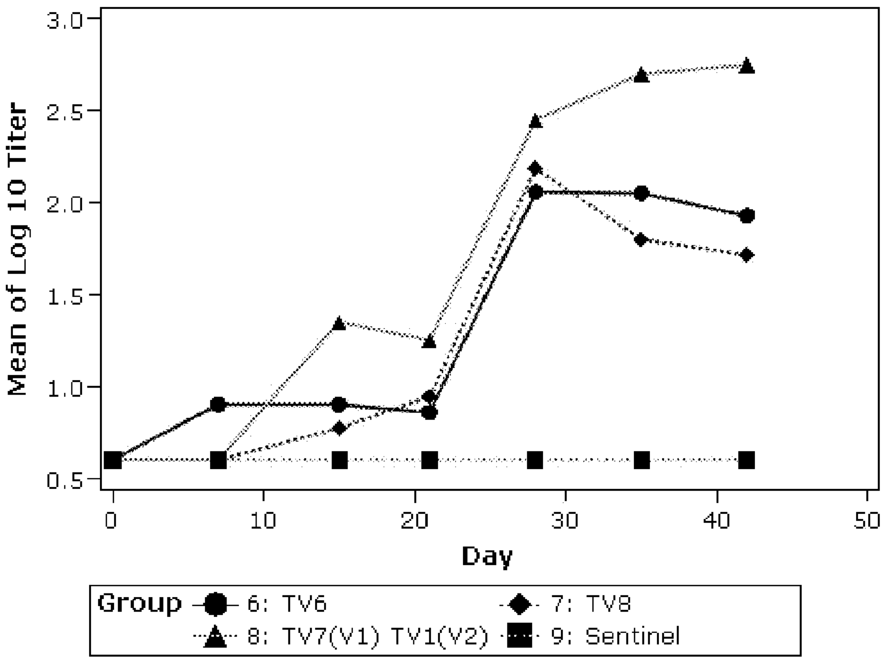
FIG. 24 depicts mean FMDV VN log 10 titer over the course of study (Day 0-day 42).

FIG. 24 shows the FMDV antibody titers in Groups 6-9 over the course of study (day 0-day 42). By Day 15 (2 weeks following the 1st vaccination), all vAD3027 vaccinates from Group 8 seroconverted to FMDV. Those in Groups 6-7 had between 29-57% of the piglets seroconvert. In addition, the mean antibody titer per group was higher in group 8 (heterologous prime-boost regimen with viral vectored FMDV vaccine and BacA24 VLP vaccine) as compared to those in Groups 6-7.

Antibody responses to Adenovirus (SVN) were determined in all animals from all groups in samples collected on Day 42. The results were reported in $Log_{10}$ and a value ≤0.6 $Log_{10}$ was considered negative for serum antibody.

The results showed that all control and piglets vaccinated with the BacA24VLP formulated vaccines were negative to Adenovirus by SN antibody titers on Day 42 (≤0.6 $Log_{10}$). All animals vaccinated with the vAD3027 in groups 6 and 7 seroconverted with titers ranging between 1.8 and 3.0, while 50% of the piglets in group 8 seroconverted. Overall, animals in group 6 had a higher antibody response to adenovirus.

Example 12.2

Serology Assessment of FMDV O1 Manisa, Asia and Iraq Vaccines

The goal of the study is to evaluate the immunogenicity of various FMDV O1 Manisa, Asia and Iraq vaccine formulations including human adenovirus 5-vectored FMDV vaccine and Baculovirus expressed FMD O1 Manisa, Asia and Iraq recombinant VLP (covalent cage) vaccine in conjunction with different adjuvants (or without) following vaccination in pigs.

The study design is as described in Example 12.1. The blood samples from the vaccinated animals are taken at various stages as described in Example 12.1 and tested for serology. The results show that the composition or vaccine of the present invention is immunogenic and provides protection in animals.

Example 14

Serology Assessment and Efficacy of Various Foot and Mouth Disease Virus (FMDV) Vaccine Candidates Following Vaccination in in Conventional Swine and Cattle and MDA-Positive Swine and Cattle The goal of the study is to evaluate the prime-boost administration (two administrations) of two heterologous vaccines or administration at the same time (one administration) of two heterologous vaccines in conventional swine or cattle to increase immune response, and also in MDA-positive pigs and cattle to overcome MDA and increase immune response. The heterologous vaccines may be different types of vaccines, such as FMDV VLPs vaccine or FMDV viral vector vaccine expressing the capsid from the same FMDV serotype. The heterologous vaccines may also be the same type of vaccines expressing the capsid of different FMDV serotypes, such as A24, O1 Manisa, Asia or Iraq strains. The heterologous vaccines may also be different types of vaccines expressing the capsids of different FMDV serotypes, such as A24, 01 Manisa, Asia or Iraq strains. The heterologous vaccines may also be different types of vaccines, i.e. FMDV VLPs vaccine or FMDV viral vector vaccine, expressing the capsids of different FMDV serotypes, such as A24, O1 Manisa, Asia or Iraq strains.

In one group, conventional pigs or cattle are vaccinated twice at an interval of between 3-5 weeks with FMDV VLPs vaccine and followed by recombinant viral FMDV vaccine, or primed with recombinant viral FMDV vaccine and boosted with FMDV VLPs vaccine. In another group, conventional pigs or cattle are vaccinated once with both FMDV VLPs and recombinant viral FMDV vaccines at the same time.

In one group, pigs or cattle which are MDA-positive are vaccinated twice at an interval of between 3-5 weeks with FMDV VLPs vaccine and followed by recombinant viral FMDV vaccine, or primed with recombinant viral FMDV vaccine and boosted with FMDV VLPs vaccine. In another group, pigs or cattle which are MDA-positive are vaccinated once with both FMDV VLPs and recombinant viral FMDV vaccines at the same time.

The animals are challenged with homologous or heterologous FMDV strains after the vaccination.

The protective efficacy induced by the composition or vaccine is evaluated against the FMDV pathogen by vaccination challenge in conventional animals or MDV-positive animals. The protective effect is evaluated by clinical observations and/or viral load of the specific pathogen in tissues and blood. The blood samples from the vaccinated animals are taken at various stages and tested for serology. The results show that the composition or vaccine of the present invention is immunogenic and provides protection in in conventional animals and MDV-positive animals.

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition or vaccine comprising a foot and mouth Disease Virus (FMDV) antigen, wherein the FMDV antigen comprises a polypeptide having the sequence as set forth in SEQ ID NO: 10.

2. A composition or vaccine comprising a foot and mouth Disease Virus (FMDV) antigen, wherein the FMDV antigen is encoded by a polynucleotide having the sequence as set forth in SEQ ID NO: 11.

3. The composition or vaccine of claim 1 or 2, wherein the FMDV antigen is expressed by a baculovirus vector in insect cells.

4. The composition or vaccine of claim 1 or 2, wherein the FMDV antigen is a modified P1 polypeptide comprising a cysteine substitution at amino acid 179 of SEQ ID NO: 10.

5. The composition or vaccine of claim 1 or 2, wherein the composition or vaccine further comprises a pharmaceutically or veterinarily acceptable carrier, excipient, adjuvant, or vehicle.

6. A substantially purified FMDV empty capsid or FMDV VLP expressed in insect cells, wherein the FMDV empty capsid or VLP comprises a polypeptide having the sequence as set forth in SEQ ID NO:10.

7. The FMDV empty capsid or VLP of claim 6, wherein the polypeptide is a modified FMDV P1 that comprises a cysteine substitution amino acid 179 of SEQ ID NO: 10.

8. A method of vaccinating an animal susceptible to FMDV infection or eliciting an immune response in the animal against FMDV comprising at least one administration of the composition of any one of claims 1,2,3,4,5, or the FMDV empty capsids or VLPs of any one of claims 6-7.

9. The method of claim 8, wherein the method comprises a prime-boost administration regimen.

10. The method of claim 8, wherein the method comprises one or more administrations of same or different FMDV compositions or vaccines.

11. The composition or vaccine of claim 1, wherein the FMDV antigen forms FMDV VLPs.

12. The composition or vaccine of claim 11, wherein the FMDV VLPs are encoded by a polynucleotide having the sequence as set forth in SEQ ID NO:11.

* * * * *